(12) United States Patent
Billen et al.

(10) Patent No.: US 12,391,640 B2
(45) Date of Patent: Aug. 19, 2025

(54) PROCESS OF MAKING A CRYSTALLINE EDG-2 RECEPTOR ANTAGONIST

(71) Applicant: HORIZON THERAPEUTICS IRELAND DAC, Dublin (IE)

(72) Inventors: Denis Billen, Dublin (IE); Bênédicte Martin, Dublin (IE); Michelle O'Mahony, Dublin (IE)

(73) Assignee: HORIZON THERAPEUTICS IRELAND DAC, Dublin (IE)

( * ) Notice: Subject to any disclaimer, the term of this patent is extended or adjusted under 35 U.S.C. 154(b) by 42 days.

(21) Appl. No.: 18/176,862

(22) Filed: Mar. 1, 2023

(65) Prior Publication Data

US 2023/0295073 A1    Sep. 21, 2023

Related U.S. Application Data

(60) Provisional application No. 63/315,898, filed on Mar. 2, 2022.

(51) Int. Cl.
*C07C 231/24* (2006.01)
*C07C 231/12* (2006.01)

(52) U.S. Cl.
CPC .......... *C07C 231/24* (2013.01); *C07C 231/12* (2013.01); *C07B 2200/13* (2013.01)

(58) Field of Classification Search
None
See application file for complete search history.

(56) References Cited

U.S. PATENT DOCUMENTS

| | | |
|---|---|---|
| 5,571,506 A | 11/1996 | Regan et al. |
| 6,225,352 B1 | 5/2001 | Horwell et al. |
| 6,375,986 B1 | 4/2002 | Ryde et al. |
| 6,431,478 B1 | 8/2002 | Reed et al. |
| 6,582,285 B2 | 6/2003 | Czekai et al. |
| 6,592,903 B2 | 7/2003 | Ryde et al. |
| 6,656,971 B2 | 12/2003 | Wu et al. |
| 6,742,734 B2 | 6/2004 | Reed et al. |
| 6,745,962 B2 | 6/2004 | Reed et al. |
| 6,861,448 B2 | 3/2005 | Brouillette et al. |
| 6,953,857 B2 | 10/2005 | Nazare et al. |
| 6,969,529 B2 | 11/2005 | Bosch et al. |
| 6,976,647 B2 | 12/2005 | Reed et al. |
| 6,991,191 B2 | 1/2006 | Reed et al. |
| 7,067,665 B2 | 6/2006 | Nazare et al. |
| 7,084,136 B2 | 8/2006 | Tanimoto et al. |

(Continued)

FOREIGN PATENT DOCUMENTS

| | | |
|---|---|---|
| EP | 1217000 A1 | 6/2002 |
| EP | 1349847 B1 | 4/2005 |

(Continued)

OTHER PUBLICATIONS

PCT/IB2023/000120 International Search Report and Written Opinion dated Jul. 25, 2023.

(Continued)

*Primary Examiner* — Renee Claytor
*Assistant Examiner* — Jennifer C Sawyer
(74) *Attorney, Agent, or Firm* — MARSHALL, GERSTEIN & BORUN LLP

(57) ABSTRACT

Described herein are methods of making crystalline Form 1 of 2-(4-methoxy-3-(3-methylphenethoxy)benzamido)-2,3-dihydro-1H-indene-2-carboxylic acid.

14 Claims, 26 Drawing Sheets

(56) References Cited

U.S. PATENT DOCUMENTS

| | | | |
|---|---|---|---|
| 7,208,601 | B2 | 4/2007 | Mjalli et al. |
| 7,244,451 | B2 | 7/2007 | Bosch et al. |
| 7,288,267 | B2 | 10/2007 | Bosch et al. |
| 7,459,472 | B2 | 12/2008 | Mjalli et al. |
| 7,465,825 | B2 | 12/2008 | Van Zandt et al. |
| 7,501,538 | B2 | 3/2009 | Mjalli et al. |
| 7,521,068 | B2 | 4/2009 | Bosch et al. |
| 7,575,184 | B2 | 8/2009 | Reed et al. |
| 7,695,739 | B2 | 4/2010 | Cooper et al. |
| 7,713,551 | B2 | 5/2010 | Mcgurk et al. |
| 7,842,232 | B2 | 11/2010 | Bosch et al. |
| 8,309,136 | B2 | 11/2012 | Cooper et al. |
| 8,362,073 | B2 | 1/2013 | Schaefer et al. |
| 8,445,530 | B2 | 5/2013 | Schaefer et al. |
| 8,802,720 | B2 | 8/2014 | Schaefer et al. |
| 9,328,071 | B2 | 5/2016 | Schaefer et al. |
| 9,345,665 | B2 | 5/2016 | Ryde et al. |
| 9,974,746 | B2 | 5/2018 | Ryde et al. |
| 9,974,747 | B2 | 5/2018 | Ryde et al. |
| 9,974,748 | B2 | 5/2018 | Ryde et al. |
| 2002/0165275 | A1 | 11/2002 | Wu et al. |
| 2002/0198195 | A1 | 12/2002 | Nazare et al. |
| 2003/0083269 | A1 | 5/2003 | Brouillette et al. |
| 2004/0024019 | A1 | 2/2004 | Tanimoto et al. |
| 2004/0157919 | A1 | 8/2004 | Wu et al. |
| 2005/0049310 | A1 | 3/2005 | Mjalli et al. |
| 2005/0059713 | A1 | 3/2005 | Mjalli et al. |
| 2005/0165058 | A1 | 7/2005 | Nazare et al. |
| 2005/0171148 | A1 | 8/2005 | Mjalli et al. |
| 2006/0122257 | A1 | 6/2006 | Van Zandt et al. |
| 2009/0076070 | A1 | 3/2009 | Harada et al. |
| 2009/0124654 | A1 | 5/2009 | Mjalli et al. |
| 2010/0267778 | A1 | 10/2010 | Kusuda et al. |
| 2011/0152290 | A1 | 6/2011 | Schaefer et al. |
| 2013/0030008 | A1 | 1/2013 | Schaefer et al. |
| 2013/0225605 | A1 | 8/2013 | Schaefer et al. |
| 2014/0309264 | A1 | 10/2014 | Schaefer et al. |
| 2015/0031708 | A1 | 1/2015 | Hadida-Ruah et al. |
| 2016/0272577 | A1* | 9/2016 | Schaefer ............... A61P 13/12 |
| 2022/0064105 | A1 | 3/2022 | Pernerstorfer et al. |
| 2023/0147835 | A1 | 5/2023 | Peloso et al. |
| 2023/0322657 | A1 | 10/2023 | Pernerstorfer et al. |

FOREIGN PATENT DOCUMENTS

| | | |
|---|---|---|
| WO | WO-9220350 A1 | 11/1992 |
| WO | WO-9806691 A2 | 2/1998 |
| WO | WO-0194309 A1 | 12/2001 |
| WO | WO-0207516 A2 | 1/2002 |
| WO | WO-02051831 A1 | 7/2002 |
| WO | WO-02059080 A2 | 8/2002 |
| WO | WO-03006628 A2 | 1/2003 |
| WO | WO-2004099127 A1 | 11/2004 |
| WO | WO-2005012221 A1 | 2/2005 |
| WO | WO-2005014533 A2 | 2/2005 |
| WO | WO-2006055625 A2 | 5/2006 |
| WO | WO-2006093823 A1 | 9/2006 |
| WO | WO-2009135590 A1 | 11/2009 |
| WO | WO-2010048149 A2 | 4/2010 |
| WO | WO-2012016133 A2 | 2/2012 |
| WO | WO-2021202955 A1 | 10/2021 |
| WO | WO-2022043755 A2 | 3/2022 |
| WO | WO-2023166346 A1 | 9/2023 |

OTHER PUBLICATIONS

Allanore et al. Lysophosphatidic Acid Receptor 1 Antagonist SAR100842 for Patients With Diffuse Cutaneous Systemic Sclerosis: A Double-Blind, Randomized, Eight-Week Placebo-Controlled Study Followed by a Sixteen-Week Open-Label Extension Study. Arthritis Rheumatol 70(10):1634-1643 (Oct. 2018).

Berge et al. Pharmaceutical Salts. Journal of Pharmaceutical Sciences 66(1):1-19 (Jan. 1977).

Brooks et al. Limited fibrosis accompanies triple-negative breast cancer metastasis in multiple model systems and is not a preventive target. Oncotarget 9(34):23462-23481 (2018).

Byrn et al. Chapter II: Hydrates and Solvates. Solid-State Chemistry of Drugs, 2nd edition pp. 233-248 (1999).

Caira. Crystalline Polymorphism of Organic Compounds. Topics in Current Chemistry. 198:163-208 (Jan. 1998).

Ellery et al. Identification of compounds acting as negative allosteric modulators of the LPA 1 receptor. Eur J Pharmacol 833:8-15 (2018).

Giron. Applications of Thermal Analysis and Coupled Techniques in Pharmaceutical Industry. J Therm Anal Calorim 68:335-357 (2002).

Giron. Investigations of Polymorphism and Pseudo-polymorphism in Pharmaceuticals by Combined Thermoanalytical Techniques. J Therm Anal Calorim 64:37-60 (2001).

González-Gil et al. The status of the lysophosphatidic acid receptor type 1 (LPA 1 R). MedChemComm 6:13-23 (2015).

Guillory. Chapter 5: Generation of Polymorphs, Hydrates, Solvates, and Amorphous Solids. Polymorphism in Pharmaceutical Solids pp. 183-226 (Brittain, H.G., ed., 1999).

Holzer et al. K$\alpha$1,2 and K$\beta$1,3 x-ray emission lines of the 3d transition metals. Phys. Rev. A56(6):4554-4568 (1997).

International Conference on Harmonization of Technical Requirements for Registration of Pharmaceuticals for Human Use (ICH), Impurities: Guidelines for Residual Solvents, Q3C(R3) (40 pgs) (Nov. 2005).

Kihara et al. Lysophospholipid receptors in drug discovery. Exp Cell Res 333(2):171-177 (2015).

Ledein et al. Translational engagement of lysophosphatidic acid receptor 1 in skin fibrosis: from dermal fibroblasts of patients with scleroderma to tight skin 1 mouse. J Pharmacol 177(18):4296-4309 (2020).

Llona-Minguez et al. Lysophosphatidic acid receptor (LPAR) modulators: The current pharmacological toolbox. Prog Lipid Res 58:51-75 (2015).

Luquet et al. Peroxisome proliferator-activated receptor delta controls muscle development and oxydative capability. FASEB J 17(13):209-226 (2003).

PCT/IB2021/000594 International Search Report and Written Opinion dated Feb. 24, 2022.

PCT/IB2021/000594 Invitation to Pay Additional Fees dated Jan. 3, 2022.

Rodriguez-Spong et al. General principles of pharmaceutical solid polymorphism: a supramolecular perspective. Adv Drug Deliv Rev 56:241-274 (2004).

Souillac et al. Characterization of Delivery Systems, Differential Scanning Calorimetry. Encyclopedia of Controlled Drug Delivery pp. 212-227 (John Wiley & Sons 1999).

Vippagunta et al. Crystalline Solids. Advanced Drug Delivery Reviews 48:3-26 (2001).

Khanna et al. Outcome measures in systemic sclerosis: an update on instruments and current research. Curr Rheumatol Rep. 9:151-7 (2007).

Khanna et al. The American College of Rheumatology Provisional Composite Response Index for Clinical Trials in Early Diffuse Cutaneous Systemic Sclerosis Arthritis Rheumatol. 68(2):299-311 (2016).

PCT/US2021/025505 International Search Report and Written Opinion dated Jun. 29, 2021.

Sultan et al. The health assessment questionnaire (HAQ) is strongly predictive of good outcome in early diffuse scleroderma: results from an analysis of two randomized controlled trials in early diffuse scleroderma. Rheumatology 43:472-8 (2004).

\* cited by examiner

PROCESS OF MAKING A CRYSTALLINE EDG-2 RECEPTOR ANTAGONIST

CROSS-REFERENCE

This application claims the benefit of U.S. Provisional Application No. 63/315,898 filed on Mar. 2, 2022, which is incorporated herein by reference in its entirety.

FIELD OF THE INVENTION

Described herein are methods of making crystalline Form 1 of 2-(4-methoxy-3-(3-methylphenethoxy)benzamido)-2,3-dihydro-1H-indene-2-carboxylic acid (Compound I).

BACKGROUND OF THE INVENTION

Compound I is a potent selective orally available $LPA_1$ receptor antagonist that is useful in the treatment of a variety of diseases or conditions as described herein, such as fibrotic disease or conditions. Compound I is a polymorphic substance and four crystalline forms have been identified. Reliably producing a single crystalline form of a polymorphic substance can be a challenge. Described herein is a reliable and reproducible method to produce Form 1.

SUMMARY OF THE INVENTION

Compound I is a polymorphic drug candidate in development for the treatment of diseases or conditions that would benefit from treatment with an $LPA_1$ receptor antagonist, such as fibrotic diseases or conditions. Crystalline Form 1 of Compound I has been identified as the preferred crystalline form. At neutral/acidic pH, Compound I is highly insoluble in most solvents and is prone to vigorously and uncontrollably crystallize as mixtures of polymorphs. A process was previously developed for the preparation of Form 1 that comprised the addition of citric acid and seeds of Form 1 to solution of Compound I. The previously developed process utilized a tight window of temperature and pH conditions as a means of preventing a supersaturated solution of Compound I from self-crystallizing into mixtures of polymorphs. The tight window of reaction conditions to prepare Form 1 posed manufacturing challenges for the reliable production of Form 1. Thus, a need existed for an improved manufacturing process to produce crystalline Form 1 of Compound I.

Described herein is an improved method for the reliable production of crystalline Form 1 of Compound I. The process described herein allows the production of Form 1 without the need for seeds of Form 1.

In one aspect, described herein is a process for the preparation of Crystalline Form 1 of 2-(4-methoxy-3-(3-methylphenethoxy)benzamido)-2,3-dihydro-1H-indene-2-carboxylic acid (Compound I):

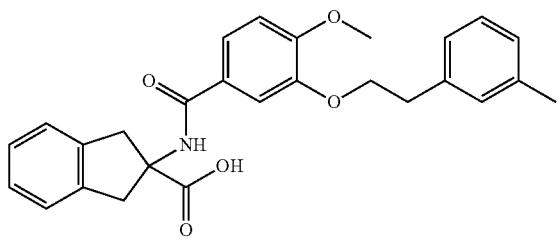

Compound I the process comprising the steps of:
(1) adding a mixture comprising a compound of Formula 2:

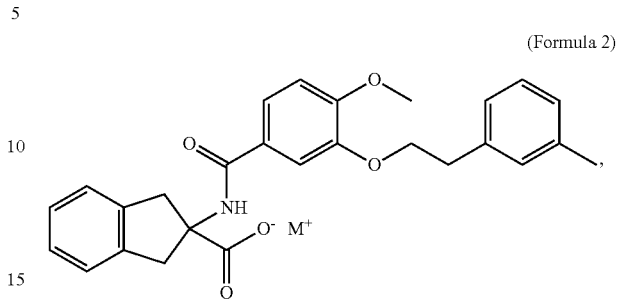

(Formula 2)

wherein $M^+$ is $Na^+$, $K^+$, or $Li^+$;
in a suitable solvent onto a slurry of citric acid; and
(2) isolating the Crystalline Form 1 of Compound I by filtration;
wherein Crystalline Form 1 of Compound I is characterized as having: an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation.

In some embodiments, the suitable solvent of step (1) is tetrahydrofuran, methanol, ethanol, ethylene glycol, acetonitrile, water, or a combination thereof. In some embodiments, the suitable solvent of step (1) is a mixture of methanol and water.

In some embodiments, the mixture comprising the compound of Formula 2 is a solution.

In some embodiments, the slurry of citric acid comprises citric acid in a suitable solvent. In some embodiments, the slurry of citric acid comprises citric acid in a solvent selected from tetrahydrofuran, methanol, ethanol, ethylene glycol, acetonitrile, water, or a combination thereof. In some embodiments, the slurry of citric acid comprises citric acid in methanol. In some embodiments, the slurry comprises at least 1.0 equivalent of citric acid relative to the amount of the compound of Formula 2. In some embodiments, from about 1.2 equivalents to about 1.5 equivalents of citric acid relative to the amount of the compound of Formula 2. In some embodiments, the concentration of the citric acid in the slurry is from about 0.5 M to about 1.5 M. In some embodiments, the concentration of the citric acid in the slurry is about 1.0 M. In some embodiments, the slurry of citric acid comprises about 1.32 equivalents of citric acid relative to the amount of the compound of Formula 2 in methanol at a concentration of about 1.0 M.

In some embodiments, the slurry of citric acid further comprises up to about 10% w/w of seeds of Crystalline Form 1 of Compound I. In some embodiments, the slurry of citric acid further comprises from 0% to about 5% w/w of seeds of Crystalline Form 1 of Compound I. In some embodiments, the slurry of citric acid further comprises from about 0.5% to about 5% w/w of seeds of Crystalline Form 1 of Compound I. In some embodiments, the slurry of citric acid further comprises about 0.5%, about 1.0%, about 1.5%, about 2.0%, about 2.5%, about 3.0%, about 3.5%, about 4.0%, about 4.5%, or about 5% w/w of seeds of Crystalline Form 1 of Compound I.

In some embodiments, the slurry of citric acid is heated to a temperature of about 40° C.

In some embodiments, the mixture comprising the compound of Formula 2 is added onto the slurry of citric acid over a period of time of from about 10 minutes to about 120 minutes. In some embodiments, after addition of the mixture comprising the compound of Formula 2 is added onto the slurry of citric acid, the resulting mixture is maintained at a temperature of about 40° C. for about 3 hours.

In some embodiments, the Crystalline Form 1 of Compound I that is isolated after step (2) is further washed with a suitable solvent up to four times. In some embodiments, the suitable solvent used for the washes is methanol, water, or a combination thereof. In some embodiments, the Crystalline Form 1 of Compound I isolated after step (2) is further dried under vacuum. In some embodiments, the Crystalline Form 1 of Compound I isolated after step (2) is further dried under vacuum at a temperature from about 35° C. to about 45° C., and for a time of from about 3 hours to about 36 hours. In some embodiments, the Crystalline Form 1 of Compound I isolated after step (2) is further dried under vacuum at a temperature of about 40° C. for about 16 hours.

In some embodiments, the process further comprises a cooling step wherein the mixture obtained after step (1) is cooled prior to the isolation of the Crystalline Form 1 of Compound I in step (2). In some embodiments, the mixture obtained after step (1) is cooled to about 10° C. In some embodiments, the mixture obtained after step (1) is cooled to about 10° C. over a period of time of about 3 hours.

In some embodiments, the mixture comprising a compound of Formula 2 is obtained by saponification of the ester moiety of the compound of Formula 1:

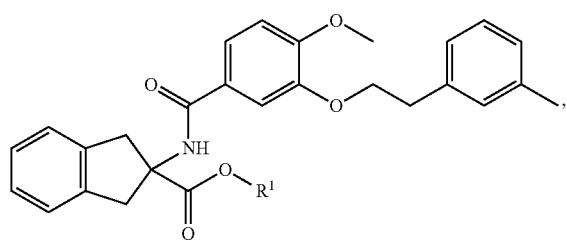

(Formula 1)

wherein $R^1$ is methyl or ethyl in a suitable solvent.

In some embodiments, the suitable solvent for the saponification comprises tetrahydrofuran, methanol, ethanol, ethylene glycol, acetonitrile, water, or a combination thereof. In some embodiments, the suitable solvent for the saponification comprises a mixture of methanol and water.

In some embodiments, the compound of Formula 1 is dissolved in a suitable solvent to obtain a solution prior to saponification. In some embodiments, the suitable solvent is tetrahydrofuran, methanol, ethanol, ethylene glycol, acetonitrile, water, or a combination thereof. In some embodiments, the suitable solvent is methanol. In some embodiments, the process further comprises heating the obtained solution of the compound of Formula 1 to a temperature of about 50° C. prior to saponification.

In some embodiments, the saponification comprises a metal hydroxide base having the formula M-OH; wherein M-OH is NaOH, KOH, or LiOH, and $M^+$ is $Na^+$, $K^+$, or $Li^+$ respectively. In some embodiments, the metal hydroxide base is added as a solution in water. In some embodiments, the concentration of the metal hydroxide base in water is from about 0.5 M to about 5.0 M. In some embodiments, the concentration of the metal hydroxide base in water is about 1.0 M. In some embodiments, the saponification comprises at least 1.0 equivalent of the metal hydroxide base relative to the amount of the compound of Formula 1. In some embodiments, the saponification comprises from about 1.1 equivalents to about 1.25 equivalents of the metal hydroxide base relative to the amount of the compound of Formula 1. In some embodiments, the metal hydroxide base is NaOH. In some embodiments, the temperature in the saponification step is about 60° C. In some embodiments, the saponification step occurs for at least 2 hours. In some embodiments, the saponification step occurs for from about 2 hours to about 4 hours.

In some embodiments, the compound of Formula 2 has the structure of Compound 2a:

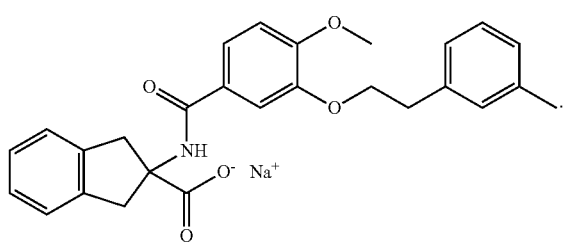

(Compound 2a)

In another aspect, described herein is a process for the preparation of Crystalline Form 1 of 2-(4-methoxy-3-(3-methylphenethoxy)benzamido)-2,3-dihydro-1H-indene-2-carboxylic acid (Compound I):

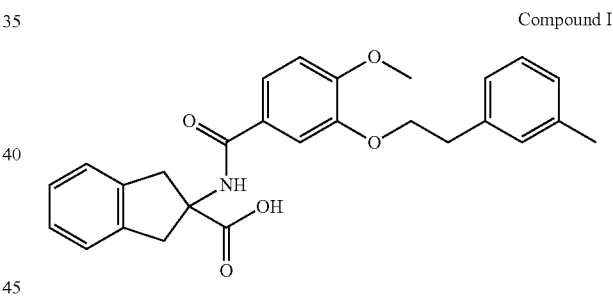

Compound I the process comprising the steps of:
(1) saponification of the ester moiety of the compound of Formula 1:

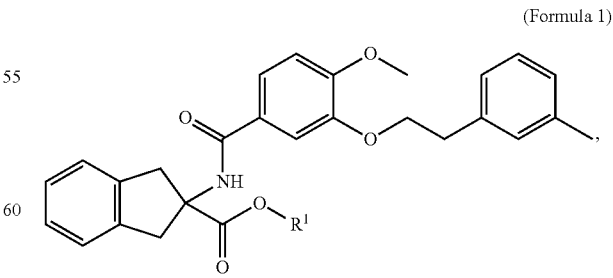

(Formula 1)

wherein $R^1$ is methyl or ethyl in a suitable solvent to provide a reaction mixture comprising the compound of Formula 2:

(Formula 2)

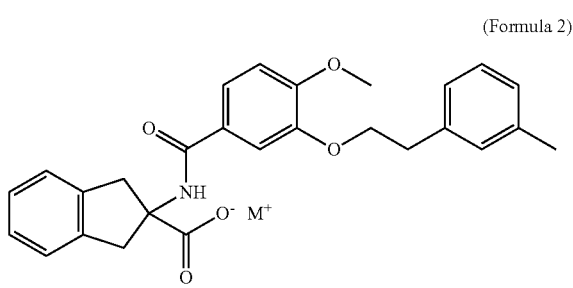

wherein M⁺ is a suitable cation;
(2) adding the reaction mixture of step (1) onto a slurry of citric acid; and
(3) isolating the Crystalline Form 1 of Compound I by filtration;
wherein Crystalline Form 1 of Compound I is characterized as having: an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation.

In some embodiments, the saponification comprises a metal hydroxide base having the formula M-OH; wherein M-OH is NaOH, KOH, or LiOH, and M⁺ is Na⁺, K⁺, or Li⁺ respectively.

In some embodiments, the saponification in step (1) comprises:
(a) obtaining a solution of the compound of Formula 1 in a suitable solvent;
(b) optionally heating the solution of step (a); and
(c) adding the metal hydroxide base as a solution in water to the solution of step (a) and heating the reaction mixture to obtain the reaction mixture comprising the compound of Formula 2.

In some embodiments, the suitable solvent of step (a) is methanol; and the solution of step (a) is heated to about 50° C.

In some embodiments, the concentration of the metal hydroxide base in water in step (c) is about 1.0 M; and from about 1.1 equivalents to about 1.25 equivalents of the metal hydroxide base is used in step (c) relative to the amount of the compound of Formula 1. In some embodiments, the reaction mixture in step (c) is heated to about 60° C. for from about 2 hours to about 4 hours.

In some embodiments, the metal hydroxide base in step (c) is NaOH; and the compound of Formula 2 has the structure of Compound 2a:

(Compound 2a)

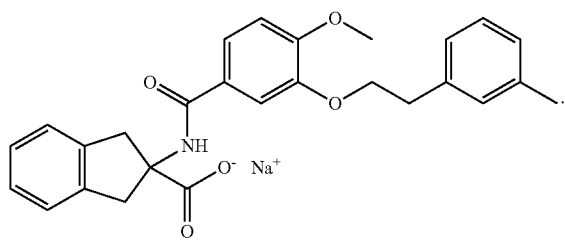

In some embodiments, the slurry of citric acid comprises from about 1.2 equivalents to about 1.5 equivalents of citric acid relative to the amount of the compound of Formula 1 in methanol. In some embodiments, the concentration of the citric acid in the slurry is from about 0.5 M to about 1.5 M. In some embodiments, the concentration of the citric acid in the slurry is about 1.0 M. In some embodiments, the slurry of citric acid comprises about 1.32 equivalents of citric acid relative to the amount of the compound of Formula 1 in methanol at a concentration of about 1.0 M. In some embodiments, the slurry of citric acid further comprises up to about 10% w/w of seeds of Crystalline Form 1 of Compound I. In some embodiments, the slurry of citric acid further comprises about 0.5%, about 1.0%, about 1.5%, about 2.0%, about 2.5%, about 3.0%, about 3.5%, about 4.0%, about 4.5%, or about 5% w/w of seeds of Crystalline Form 1 of Compound I. In some embodiments, the mixture comprising the compound of Formula 2 is added onto the slurry of citric acid over a period of time of from about 10 minutes to about 120 minutes. In some embodiments, after addition of the mixture comprising the compound of Formula 2 is added onto the slurry of citric acid, the resulting mixture is maintained at a temperature of about 40° C. for about 3 hours.

In another aspect, described herein is a process for the preparation of Crystalline Form 1 of 2-(4-methoxy-3-(3-methylphenethoxy)benzamido)-2,3-dihydro-1H-indene-2-carboxylic acid (Compound I):

Compound I

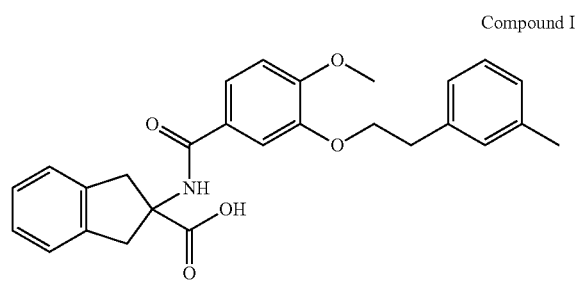 [SMILES: COc1ccc(C(=O)NC2(C(=O)O)Cc3ccccc3C2)cc1OCCc1cccc(C)c1]

the process comprising the steps of:
(1) saponification of the ester moiety of the compound methyl 2-(4-methoxy-3-(3-methylphenethoxy)benzamido)-2,3-dihydro-1H-indene-2-carboxylate (Compound 1a):

(Compound 1a)

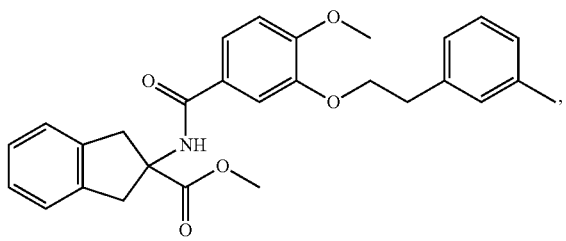

with NaOH in a suitable solvent to provide a reaction mixture comprising sodium 2-(4-methoxy-3-(3-methylphenethoxy)benzamido)-2,3-dihydro-1H-indene-2-carboxylate (Compound 2a):

(Compound 2a)

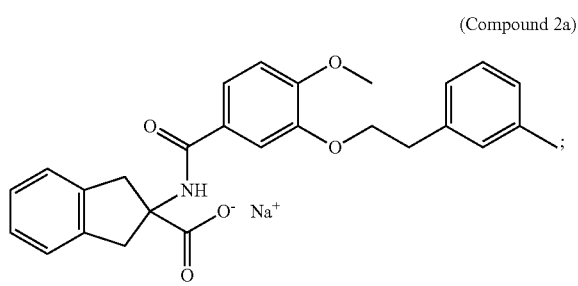 [SMILES: COc1ccc(C(=O)NC2(C(=O)[O-])Cc3ccccc3C2)cc1OCCc1cccc(C)c1 ; [Na+]]

(2) adding the reaction mixture of step (1) onto a slurry of citric acid; and
(3) isolating the Crystalline Form 1 of Compound I by filtration;
wherein Crystalline Form 1 of Compound I is characterized as having: an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation.

In some embodiments, the saponification of step (1) comprises:
a. obtaining a solution of Compound 1a in methanol and heating to a temperature of about 50° C.;
b. adding from about 1.1 equivalents to about 1.25 equivalents of NaOH relative to Compound 1a as an about 1.0 M solution in water to the solution in step (a) to obtain a reaction mixture; and
c. heating the reaction mixture of step (b) to about 60° C. for from about 2 hours to about 4 hours.

In some embodiments, the slurry of citric acid comprises from about 1.2 equivalents to about 1.5 equivalents of citric acid relative to the amount of the compound of Formula 1 in methanol; the concentration of the citric acid in the slurry is about 1.0 M; and the slurry of citric acid comprises from 0% to about 5% w/w of seeds of Crystalline Form 1 of Compound I. In some embodiments, the slurry of citric acid is heated to a temperature of about 40° C.; the mixture comprising the compound of Formula 2 is added onto the slurry of citric acid over a period of time of from about 10 minutes to about 120 minutes; and the resulting mixture is maintained at a temperature of about 40° C. for about 3 hours.

In some embodiments, the Crystalline Form 1 of Compound I that is isolated after step (3) is further washed with a mixture of methanol and water two times followed by methanol two times, and is further dried under vacuum at a temperature from about 35° C. to about 45° C., and for a time of from about 3 hours to about 36 hours.

In another aspect, described herein is Crystalline Form 1 of 2-(4-methoxy-3-(3-methylphenethoxy)benzamido)-2,3-dihydro-1H-indene-2-carboxylic acid (Compound I):

Compound I

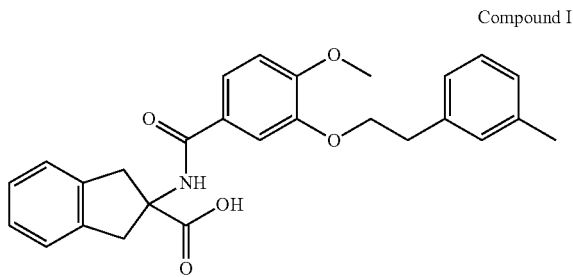 [SMILES: COc1ccc(C(=O)NC2(C(=O)O)Cc3ccccc3C2)cc1OCCc1cccc(C)c1]

as prepared by the processes described herein. In some embodiments, Crystalline Form 1 of Compound I is characterized as having: an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation. In some embodiments, the crystalline Form 1 of Compound I is substantially free of crystalline Form 2 of Compound I. In some embodiments, the crystalline Form 1 of Compound I comprises less than 1% w/w of crystalline Form 2 of Compound I.

Also described herein, in some embodiments, is a pharmaceutical composition comprising crystalline form 1 of Compound I as prepared herein and at least one pharmaceutically acceptable excipient. In some embodiments, the pharmaceutical composition is formulated for administration to a mammal by oral administration. In some embodiments, the pharmaceutical composition is formulated for administration to a mammal by oral administration in the form of a tablet, a pill, a capsule, a suspension, or a solution. In some embodiments, the pharmaceutical composition is in the form of a solid form pharmaceutical composition. In some embodiments, the pharmaceutical composition is in the form of a tablet, a pill, or a capsule.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

Figure 1:
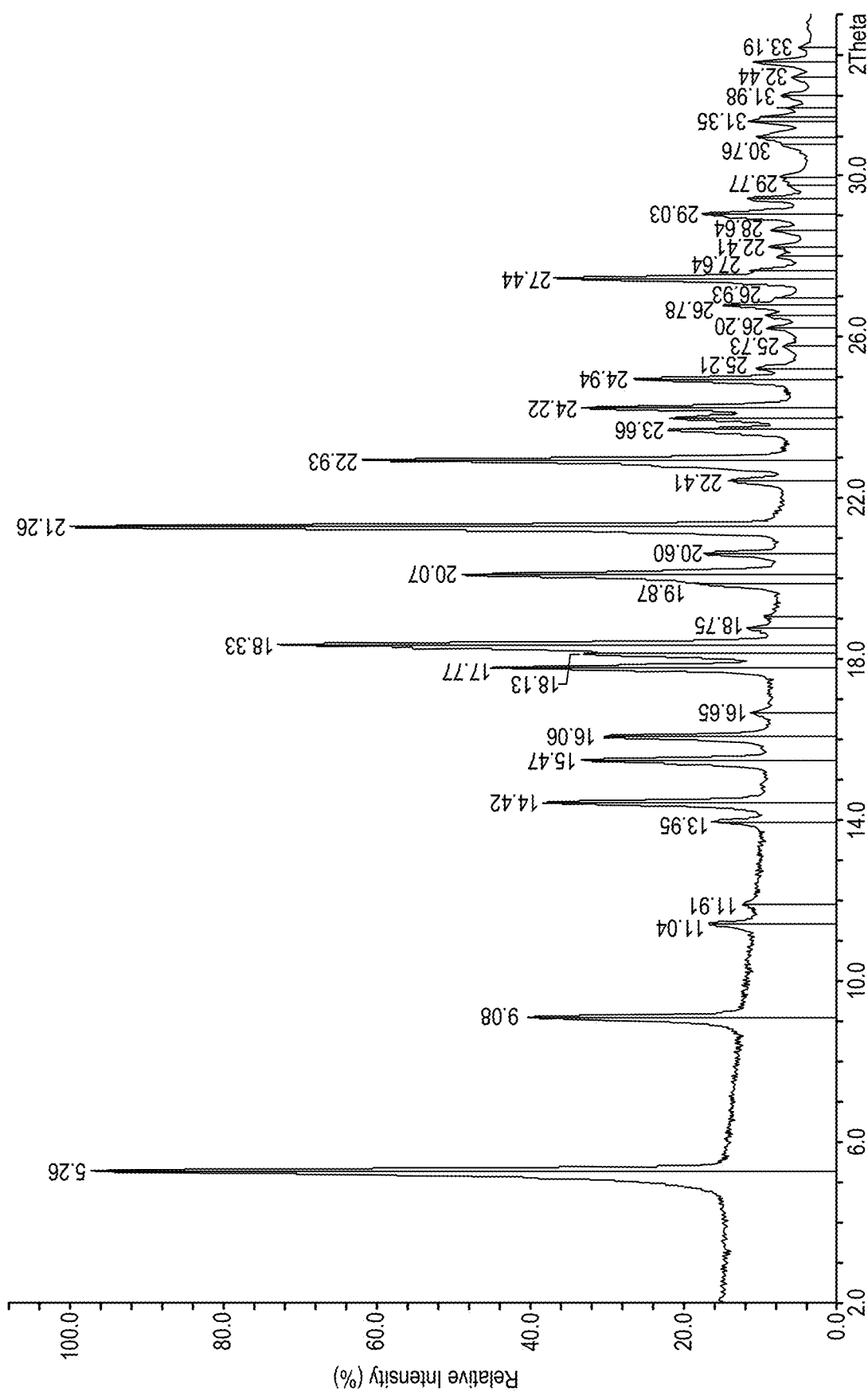
FIG. 1 shows the X-ray powder diffraction (XRPD) pattern of Form 1.

DETAILED DESCRIPTION OF THE INVENTION 2-(4-methoxy-3-(3-methylphenethoxy)benzamido)-2,3-dihydro-1H-indene-2-carboxylic acid (Compound I) is a potent and selective $LPA_1$ receptor antagonist. The $LPA_1$ receptor is activated by lysophosphatidic acid (LPA). $LPA_1$ receptor antagonists are useful in the treatment of diseases or conditions for which abnormal LPA signaling plays a role, such as atherosclerosis, myocardial infarction, and heart failure.

Compound I

Compound I is a potent selective orally available $LPA_1$ receptor antagonist that is useful in the treatment of a variety of diseases or conditions as described herein, such as fibrotic disease or conditions. In vivo, Compound I reversed dermal thickening and significantly inhibited myofibroblast differentiation and reduced collagen content in a mouse model of skin fibrosis. Mechanistic investigations showed that the antifibrotic effects of $LPA_1$ blockade could be mediated partly via inhibition of the Wnt signaling pathway. In the clinical setting, Compound I was well tolerated in patients with diffuse cutaneous systemic sclerosis SSc (dcSSc), demonstrated target engagement, and improved outcome measures (Y. Allanore et al. *Arthritis & Rheumatology*, Vol. 70, No. 10, October 2018, pp 1634-1643).

The preparation and uses of Compound I have been previously described (see, WO 2009/135590, U.S. Pat. Nos. 8,362,073, 8,445,530, 8,802,720, 9,328,071, each of which is incorporated by reference in its entirety). The preparation of crystalline form 1 of Compound I has been previously described (see, International Patent Application No. PCT/IB2021/000594, and U.S. patent application Ser. No. 17/463,369, each of which is incorporated by reference in its entirety).

Compound I refers to 2-(4-methoxy-3-(3-methylphenethoxy)benzamido)-2,3-dihydro-1H-indene-2-carboxylic acid, which has the chemical structure shown below:

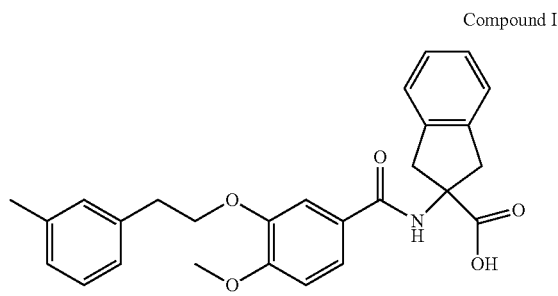 [SMILES: COc1ccc(C(=O)NC2(C(=O)O)Cc3ccccc3C2)cc1OCCc1cccc(C)c1]

Compound I

In some embodiments provided herein, Compound I is crystalline.

In some embodiments provided herein, Compound I is a single crystalline form. In some embodiments provided herein, Compound I is a single crystalline form that is substantially free of any other crystalline form. In some embodiments, the crystalline solid form is a single solid state form, e.g. crystalline Form 1. In some embodiments, "substantially free" means less than about 10% w/w, less than about 9% w/w, less than about 8% w/w, less than about 7% w/w, less than about 6% w/w, less than about 5% w/w, less than about 4% w/w, less than about 3% w/w, less than about 2.5% w/w, less than about 2% w/w, less than about 1.5% w/w, less than about 1% w/w, less than about 0.75% w/w, less than about 0.50% w/w, less than about 0.25% w/w, less than about 0.10% w/w, or less than about 0.05% w/w of any other crystalline form (e.g., Form 2) in a sample of crystalline Form 1. In some embodiments, "substantially free" means an undetectable amount (e.g., by XRPD analysis).

In some embodiments, crystallinity of a solid form is determined by X-Ray Powder Diffraction (XRPD). In some embodiments, crystallinity of a solid form is determined by solid state NMR. In some embodiments, crystallinity of a solid form is determined by Fourier Transform IR Spectroscopy (FTIR).

Crystalline Form 1 of Compound I

In one aspect, provided herein is crystalline Form 1 of Compound I. Some embodiments provide a composition comprising crystalline Form 1 of Compound I. In some embodiments, crystalline Form 1 of Compound I is characterized as having:

an X-ray powder diffraction (XRPD) pattern substantially the same as shown in FIG. 1, as measured using Cu (Kα) radiation;

an X-ray powder diffraction (XRPD) pattern derived using Cu (Kα) radiation with peaks at 5.2±0.2° 2-Theta, 9.0±0.2° 2-Theta, 14.4±0.2° 2-Theta, and 17.7±0.2° 2-Theta, as measured using Cu (Kα) radiation;

a Fourier Transform IR Spectroscopy (FTIR) pattern with a peak at about 1739.6 $cm^{-1}$;

unit cell parameters substantially equal to the following at 293 K:

| Crystal System | triclinic |
|---|---|
| Space Group | P-1; Z = 2 |
| a (Å) | 6.521(6) |
| b (Å) | 10.548(9) |

Figure 4:
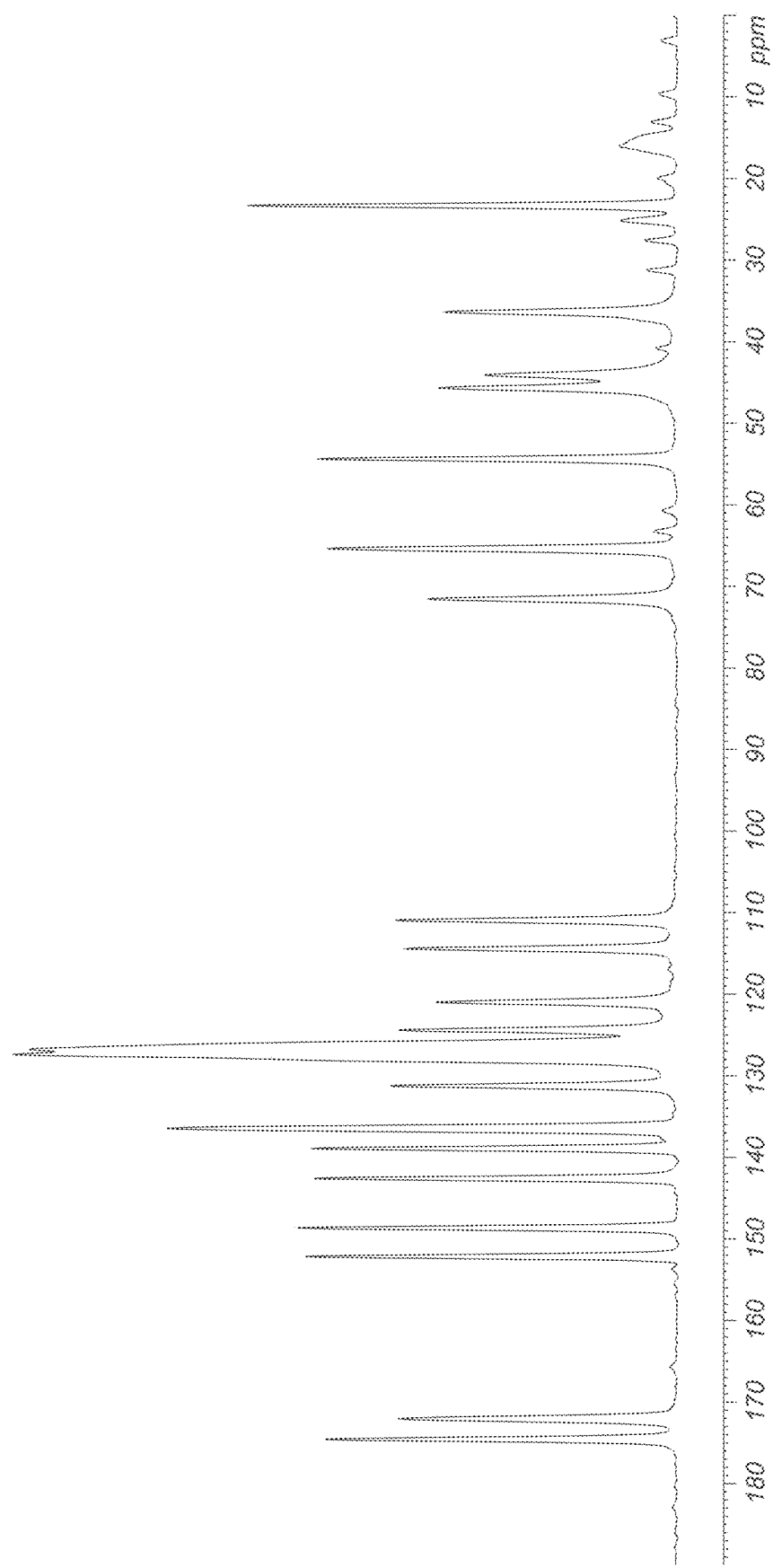
FIG. 4 shows the Solid State $^{13}$Carbon NMR Spectrum of Form 1.

| | |
|---|---|
| c (Å) | 17.453(15) |
| α (°) | 104.080(16) |
| β (°) | 92.430(16) |
| γ (°) | 101.081(17) |
| V (Å$^3$) | 1137.6(17) |
| Calculated Density (Mg/m$^3$) | 1.301 |
| Unique Reflections | 4753 | a Solid State $^{13}$Carbon Nuclear Magnetic Resonance (ssNMR) spectrum substantially the same as shown in FIG. 4;

a Solid State $^{13}$Carbon Nuclear Magnetic Resonance (ssNMR) spectrum characterized by resonances (δc) at 23.35, 124.43, 126.78, 127.42, and 136.47 ppm; or combinations thereof.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation; and a Fourier Transform IR Spectroscopy (FTIR) pattern with a peak at about 1739.6 cm$^{-1}$.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation; and a Differential Scanning Calorimetry (DSC) thermogram with three endothermic events having: an onset at about 198.5° C. and a peak at about 200.4° C.; an onset at about 204.8° C. and a peak at about 205.8° C.; and an onset at about 213.9° C. and a peak at about 216.3° C.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation; and a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm.

In some embodiments, crystalline Form 1 of Compound I has an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation; and a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm; and a Differential Scanning Calorimetry (DSC) thermogram with three endothermic events having: an onset at about 198.5° C. and a peak at about 200.4° C.; an onset at about 204.8° C. and a peak at about 205.8° C.; and an onset at about 213.9° C. and a peak at about 216.3° C.

In some embodiments, crystalline Form 1 of Compound I has an X-ray powder diffraction (XRPD) pattern substantially the same as shown in FIG. 1, as measured using Cu (Kα) radiation.

Figure 2:
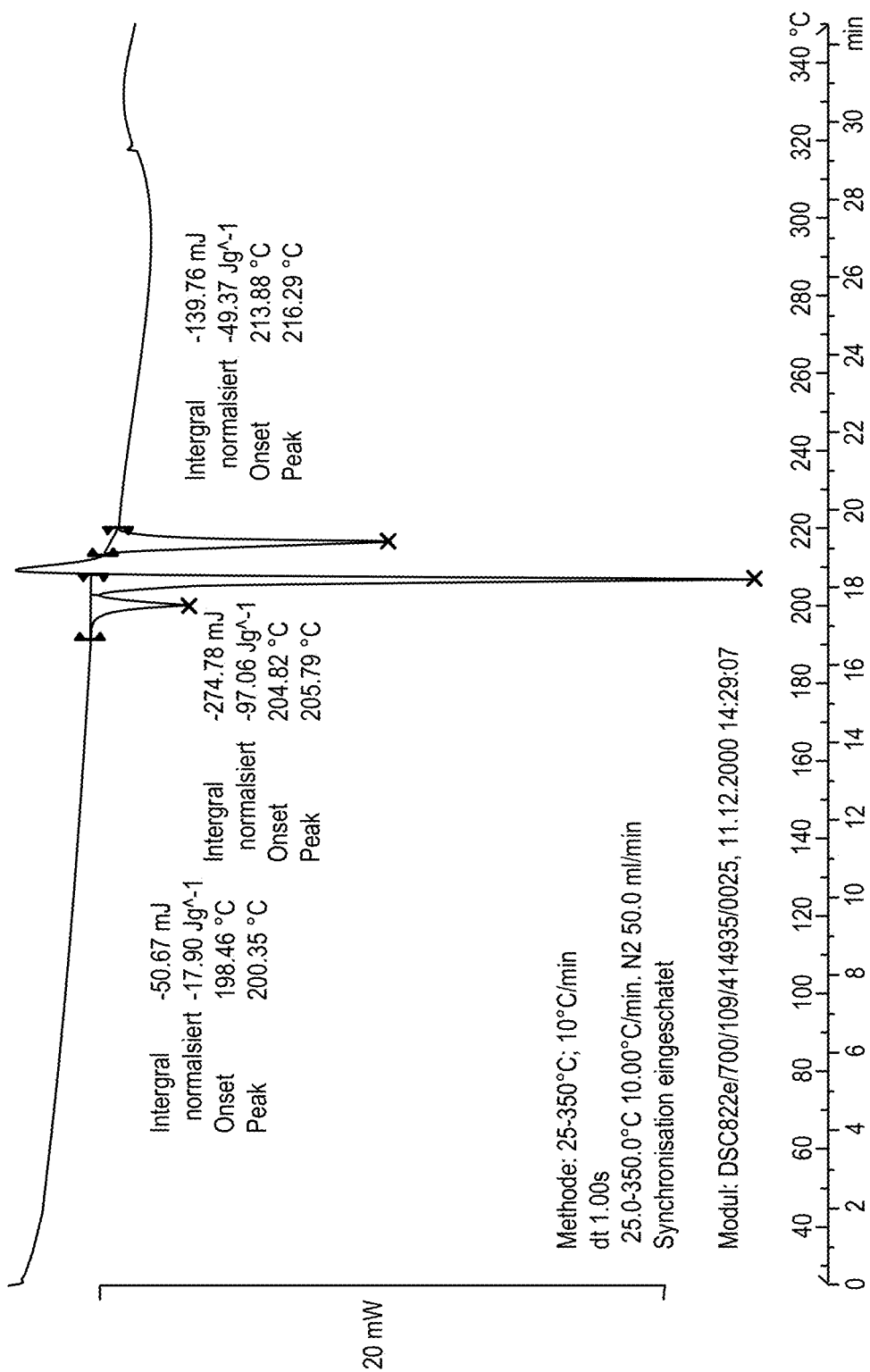
FIG. 2 shows the Differential Scanning Calorimetry (DSC) thermogram of Form 1.

In some embodiments, crystalline Form 1 of Compound I has an X-ray powder diffraction (XRPD) pattern substantially the same as shown in FIG. 1, as measured using Cu (Kα) radiation; and a Differential Scanning Calorimetry (DSC) thermogram substantially the same as shown in FIG. 2.

In some embodiments, crystalline Form 1 of Compound I has an X-ray powder diffraction (XRPD) pattern substantially the same as shown in FIG. 1, as measured using Cu (Kα) radiation; and a Fourier Transform IR Spectroscopy (FTIR) pattern with a peak at about 1739.6 cm$^{-1}$. In some embodiments, crystalline Form 1 of Compound I has an X-ray powder diffraction (XRPD) pattern substantially the same as shown in FIG. 1, as measured using Cu (Kα) radiation; and a Fourier Transform IR Spectroscopy (FTIR) pattern with a peak at about 1739.6 cm$^{-1}$; and a Differential Scanning Calorimetry (DSC) thermogram substantially the same as shown in FIG. 2.

In some embodiments, crystalline Form 1 of Compound I has an X-ray powder diffraction (XRPD) pattern substantially the same as shown in FIG. 1, as measured using Cu (Kα) radiation; and a Solid State $^{13}$Carbon Nuclear Magnetic Resonance (ssNMR) spectrum substantially the same as shown in FIG. 4. In some embodiments, crystalline Form 1 of Compound I has an X-ray powder diffraction (XRPD) pattern substantially the same as shown in FIG. 1, as measured using Cu (Kα) radiation; and a Solid State $^{13}$Carbon Nuclear Magnetic Resonance (ssNMR) spectrum substantially the same as shown in FIG. 4; and a Differential Scanning Calorimetry (DSC) thermogram substantially the same as shown in FIG. 2.

In some embodiments, crystalline Form 1 of Compound I having unit cell parameters substantially equal to the following at 293 K:

| | |
|---|---|
| Crystal System | triclinic |
| Space Group | P-1; Z = 2 |
| a (Å) | 6.521(6) |
| b (Å) | 10.548(9) |
| c (Å) | 17.453(15) |
| α (°) | 104.080(16) |
| β (°) | 92.430(16) |
| γ (°) | 101.081(17) |
| V (Å$^3$) | 1137.6(17) |
| Calculated Density (Mg/m$^3$) | 1.301 |
| Unique Reflections | 4753 |

In some embodiments, crystalline Form 1 of Compound I is characterized as having a Solid State $^{13}$Carbon Nuclear Magnetic Resonance (ssNMR) spectrum substantially the same as shown in FIG. 4. In some embodiments, crystalline Form 1 of Compound I is characterized as having a Solid State $^{13}$Carbon Nuclear Magnetic Resonance (ssNMR) spectrum substantially the same as shown in FIG. 4; and a Fourier Transform IR Spectroscopy (FTIR) pattern with a peak at about 1739.6 cm$^{-1}$. In some embodiments, crystalline Form 1 of Compound I is characterized as having a Solid State $^{13}$Carbon Nuclear Magnetic Resonance (ssNMR) spectrum substantially the same as shown in FIG. 4; and a Differential Scanning Calorimetry (DSC) thermogram substantially the same as shown in FIG. 2.

In some embodiments, crystalline Form 1 of Compound I is characterized as having a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm.

In some embodiments, crystalline Form 1 of Compound I is characterized as having a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm; and a Differential Scanning Calorimetry (DSC) thermogram substantially the same as shown in FIG. 2.

In some embodiments, crystalline Form 1 of Compound I is characterized as having a Solid State $^{13}$Carbon Nuclear Magnetic Resonance (ssNMR) spectrum characterized by resonances (δc) at about 23.35 ppm, about 124.43 ppm, about 126.78 ppm, about 127.42 ppm, and about 136.47 ppm; and a Fourier Transform IR Spectroscopy (FTIR) pattern with a peak at about 1739.6 cm$^{-1}$.

In some embodiments, crystalline Form 1 of Compound I is characterized as having a Fourier Transform IR Spectroscopy (FTIR) pattern with a peak at about 1739.6 cm$^{-1}$. In some embodiments, crystalline Form 1 of Compound I is characterized as having a Fourier Transform IR Spectroscopy (FTIR) pattern with a peak at about 1739.6 cm$^{-1}$; and a Differential Scanning Calorimetry (DSC) thermogram substantially the same as shown in FIG. 2.

In some embodiments, crystalline Form 1 of Compound I is characterized as having a Fourier Transform IR Spectroscopy (FTIR) pattern with a peak at about 1739.6 cm$^{-1}$; and a Differential Scanning Calorimetry (DSC) thermogram with three endothermic events having: an onset at about 198.5° C. and a peak at about 200.4° C.; an onset at about 204.8° C. and a peak at about 205.8° C.; and an onset at about 213.9° C. and a peak at about 216.3° C.

In some embodiments, crystalline Form 1 of Compound I has a DSC thermogram substantially the same as shown in FIG. 2. In some embodiments, crystalline Form 1 has a DSC thermogram with one or more endothermic events having: an onset at about 198.5° C. and a peak at about 200.4° C.; an onset at about 204.8° C. and a peak at about 205.8° C.; and/or an onset at about 213.9° C. and a peak at about 216.3° C. In some embodiments, crystalline Form 1 has a DSC thermogram with three endothermic events having: an onset at about 198.5° C. and a peak at about 200.4° C.; an onset at about 204.8° C. and a peak at about 205.8° C.; and an onset at about 213.9° C. and a peak at about 216.3° C.

Figure 3:
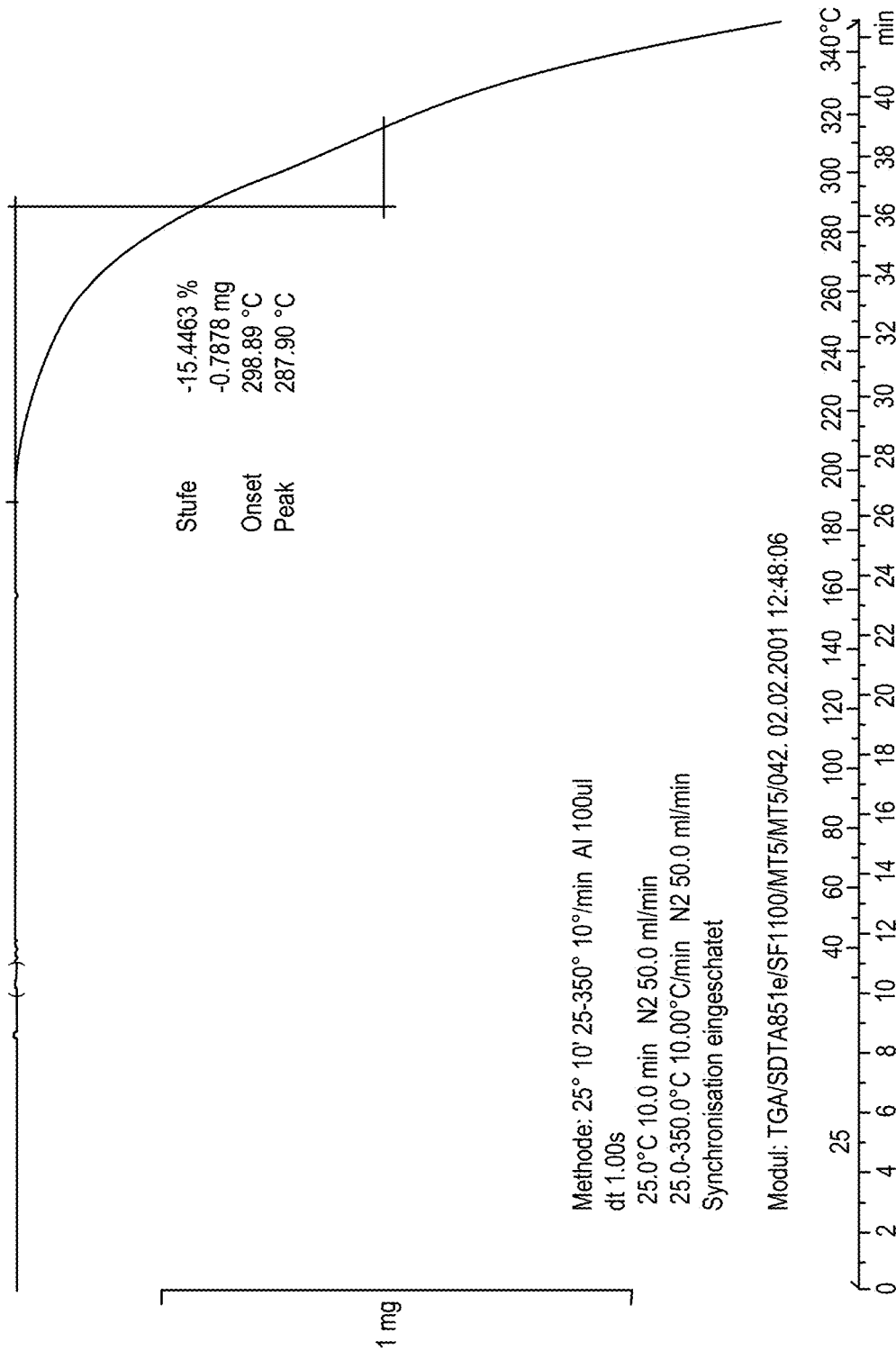
FIG. 3 shows the Thermogravimetric Analysis (TGA) pattern of Form 1.

In some embodiments, crystalline Form 1 of Compound I has a TGA pattern substantially the same as shown in FIG. 3. In some embodiments, crystalline Form 1 has a TGA pattern with a 15.4% w/w loss from about 287.9° C. to about 298.9° C. In some embodiments, crystalline Form 1 has a TGA pattern with less than 1% weight loss up to 200° C.

In some embodiments, crystalline Form 1 of Compound I has no reversible water uptake (~−0.1% w/w) between 0 and 95% Relative Humidity (RH). In some embodiments, crystalline Form 1 of Compound I has no reversible water uptake between 0 and 95% Relative Humidity (RH). In some embodiments, crystalline Form 1 of Compound I has <1% w/w reversible water uptake between 0 and 95% Relative Humidity (RH). In some embodiments, crystalline Form 1 of Compound I has ~−0.1% w/w reversible water uptake between 0 and 95% Relative Humidity (RH).

In some embodiments, crystalline Form 1 of Compound I has an FTIR spectrum with a peak at about 1739.6 cm$^{-1}$.

In some embodiments, crystalline Form 1 of Compound I has an unchanged FTIR after storage at 75% RH and 80° C. over 7 days.

In some embodiments, crystalline Form 1 of Compound I has a ssNMR spectrum substantially the same as shown in FIG. 4. In some embodiments, crystalline Form 1 has a ssNMR spectrum characterized by resonances (δc) at 23.35, 124.43, 126.78, 127.42, and 136.47 ppm. In some embodiments, crystalline Form 1 has a ssNMR spectrum further characterized by resonances (δc) at 54.41, 65.40, 138.94, 142.61, 148.68, 152.19, and 174.59 ppm. In some embodiments, crystalline Form 1 has a ssNMR spectrum characterized by resonances (δc) at 23.35, 36.40, 44.12, 45.70, 54.41, 65.40, 71.58, 110.97, 114.45, 121.00, 124.43, 126.78, 127.42, 131.27, 136.47, 138.94, 142.61, 148.68, 152.19, 172.07, and 174.59 ppm.

In some embodiments, crystalline Form 1 of Compound I converts to crystalline Form 2 when slurried in solvent at a temperature of 60° C. or above. In some embodiments, crystalline Form 1 converts to crystalline Form 2 when slurried in MEK or 1-pentanol at a temperature of 60° C. or 70° C. In some embodiments, form conversion is determined by FTIR.

In some embodiments, crystalline Form 1 of Compound I is anhydrous.

Preparation of Crystalline Form 1 of Compound I

Disclosed herein are methods for the synthesis crystalline form 1 of Compound I, as outlined in Scheme 1.

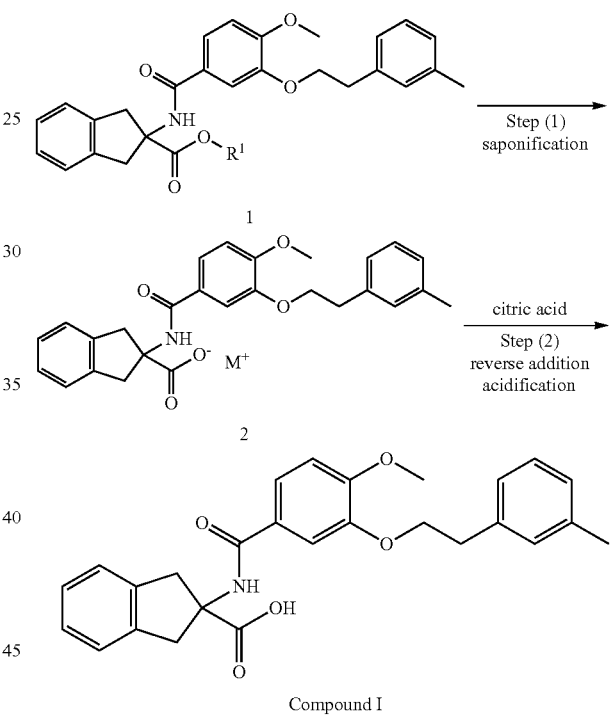

Scheme 1 Preparation of Crystalline Form 1 of Compound I where R$^1$ is methyl or ethyl, and M$^+$ is a suitable cation.

Briefly, the compound of Formula 1 undergoes a saponification reaction to yield the compound of Formula 2. The compound of Formula 2 is acidified by adding the compound to citric acid to provide Compound I, which is isolated directly from the reaction vessel as crystalline form 1 of Compound 1.

Step (1): Synthesis of a Compound of Formula 2 (Saponification)

In some embodiments, the ester moiety of the compound of Formula 1 undergoes a saponification reaction to yield a compound of Formula 2 in a suitable solvent.

In some embodiments, the compound of Formula 2 is obtained by saponification of the ester moiety of the compound of Formula 1:

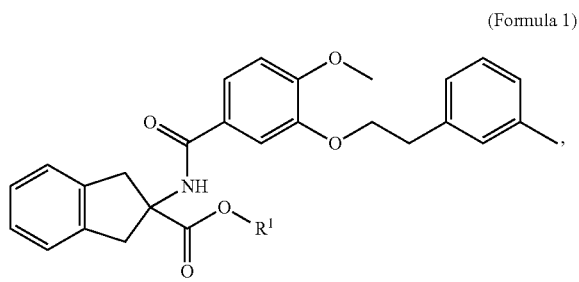
(Formula 1)

wherein R¹ is methyl or ethyl in a suitable solvent.

In some embodiments, the suitable solvent for the saponification reaction is tetrahydrofuran, methanol, ethanol, ethylene glycol, acetonitrile, water, or a combination thereof. In some embodiments, the suitable solvent is a mixture of methanol and water.

In some embodiments, the compound of Formula 1 is dissolved in a suitable solvent to obtain a solution prior to saponification. In some embodiments, the suitable solvent is tetrahydrofuran, methanol, ethanol, ethylene glycol, acetonitrile, water, or a combination thereof. In some embodiments, the suitable solvent is methanol, ethanol, water, or a combination thereof. In some embodiments, the suitable solvent is methanol. In some embodiments, the suitable solvent is ethanol. In some embodiments, the obtained solution of the compound of Formula 1 is heated prior to saponification. In some embodiments, the obtained solution of the compound of Formula 1 is heated to a temperature of about 50° C. prior to saponification. In some embodiments, "about 50° C." means from 45° C. to 55° C. In some embodiments, "about 50° C." means from 47° C. to 53° C. In some embodiments, the obtained solution of the compound of Formula 1 is heated to a temperature of from 47° C. to 53° C. prior to saponification.

In some embodiments, the saponification comprises a metal hydroxide base. In some embodiments, the saponification comprises a metal hydroxide base having the formula M-OH; wherein M-OH is NaOH, KOH, or LiOH, and M⁺ is Na⁺, K⁺, or Li⁺ respectively. In some embodiments, the saponification comprises a metal hydroxide base having the formula M-OH; wherein M-OH is NaOH, and M⁺ is Na⁺. In some embodiments, the saponification comprises a metal hydroxide base having the formula M-OH; wherein M-OH is KOH, and M⁺ is K⁺. In some embodiments, the saponification comprises a metal hydroxide base having the formula M-OH; wherein M-OH is LiOH, and M⁺ is Li⁺.

In some embodiments, the saponification comprises at least 1.0 equivalent of a metal hydroxide base relative to the amount of the compound of Formula 1. In some embodiments, the saponification comprises from about 1.1 equivalents to about 1.25 equivalents of the metal hydroxide base relative to the amount of the compound of Formula 1. In some embodiments, the saponification comprises about 1.0, about 1.05, about 1.1, about 1.15, about 1.2, about 1.25, or about 1.3 equivalents of the metal hydroxide base relative to the amount of the compound of Formula 1. In some embodiments, the saponification comprises about 1.15, about 1.16, about 1.17, about 1.18, about 1.19, about 1.20, about 1.21, about 1.22, about 1.23, about 1.24, or about 1.25 equivalents of the metal hydroxide base relative to the amount of the compound of Formula 1.

In some embodiments, the metal hydroxide base is added to the solution of compound 1 as a solution in water. In some embodiments, the concentration of the solution of metal hydroxide base in water is from about 0.5 M to about 5.0 M. In some embodiments, the metal hydroxide base is added as a solution in water. In some embodiments, the concentration of the solution of metal hydroxide base in water is from about 0.5 M to about 1.5 M. In some embodiments, the concentration of the solution of metal hydroxide base in water is about 0.1 M, about 0.5 M, about 1.0 M, about 2.0 M, or about 5.0 M. In some embodiments, the concentration of the solution of metal hydroxide base in water is about 1.0 M. In some embodiments, the concentration of the solution of metal hydroxide base in water is 1.0 M.

In some embodiments, the temperature of the reaction is maintained throughout addition of the metal hydroxide base. In some embodiments, the temperature of the reaction is maintained at about 50° C. throughout addition of the metal hydroxide base. In some embodiments, "about 50° C." means from 45° C. to 65° C. In some embodiments, "about 50° C." means from 47° C. to 63° C. In some embodiments, the temperature of the reaction is maintained at a temperature of 47° C. to 63° C. throughout addition of the metal hydroxide base. In some embodiments, the temperature of the reaction is maintained throughout addition of the metal hydroxide base by slow addition of the metal hydroxide base.

In some embodiments, the saponification step is performed at an elevated temperature. In some embodiments, the saponification step is performed at a temperature of about 50° C. to about 70° C. In some embodiments, the saponification step is performed at a temperature of about 60° C. In some embodiments, "about 60° C." means from 55° C. to 65° C. In some embodiments, "about 60° C." means from 57° C. to 63° C. In some embodiments, the saponification step is performed at a temperature of 57° C. to 63° C.

In some embodiments, the saponification step is performed for at least 1 hour. In some embodiments, the saponification step is performed for about 1 hour, about 2 hours, about 3 hours, or more. In some embodiments, the saponification step is performed for at least 2 hours. In some embodiments, the saponification step is performed for from about 2 hours to about 4 hours. In some embodiments, the saponification step is performed for about 2 hours. In some embodiments, "about 2 hours" means from about 1 h 30 min to about 2 h 30 min. In some embodiments, "about 2 hours" means from about 1 h 45 min to about 2 h 15 min. In some embodiments, "about 2 hours" means from 1 h 45 min to 2 h 15 min. In some embodiments, the saponification step is performed for 1 h 45 min to 2 h 15 min. In some embodiments, the saponification step is performed for about 2 hours. In some embodiments, "about 3 hours" means from about 2 h 30 min to about 3 h 30 min. In some embodiments, "about 3 hours" means from about 2 h 45 min to about 3 h 15 min. In some embodiments, "about 3 hours" means from 2 h 45 min to 3 h 15 min. In some embodiments, the saponification step is performed for 2 h 45 min to 3 h 15 min.

In some embodiments, the saponification step is performed at a temperature of 57° C. to 63° C. for about 1 h 45 min to 2 h 15 min. In other embodiments, the saponification step is performed at a temperature of 57° C. to 63° C. for about 2 h 45 min to 3 h 15 min.

In other embodiments, the saponification comprises an inorganic acid. In some embodiments, the inorganic acid is hydrochloric acid, sulfuric acid, trifluoroacetic acid, formic acid, or nitric acid. In some embodiments, the resulting acid is converted to the compound of Formula 2 with a suitable base.

In some embodiments, the compound of Formula 1, is Compound 1a:

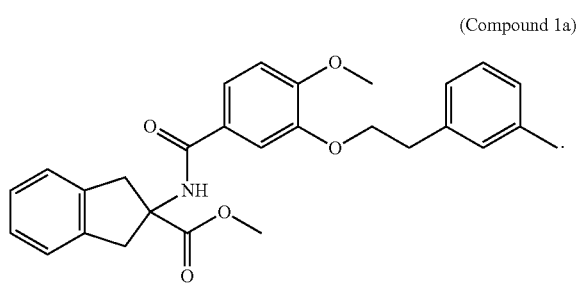 [SMILES: COC(=O)C1(NC(=O)c2ccc(OC)c(OCCc3cccc(C)c3)c2)Cc2ccccc2C1]

(Compound 1a)

In some embodiments, the compound of Formula 1, is Compound 1b:

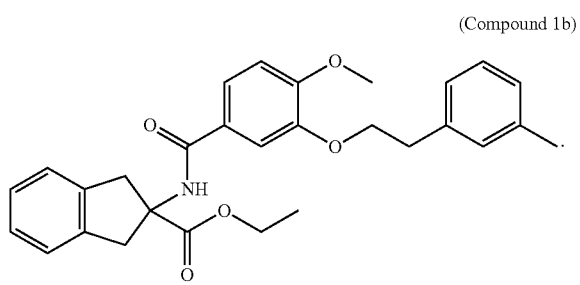 [SMILES: CCOC(=O)C1(NC(=O)c2ccc(OC)c(OCCc3cccc(C)c3)c2)Cc2ccccc2C1]

(Compound 1b)

In some embodiments, the compound of Formula 2, is Compound 2a:

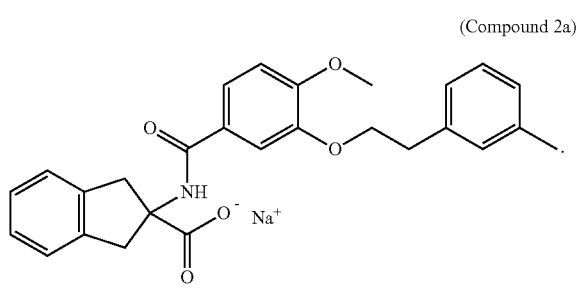 [SMILES: COc1ccc(C(=O)NC2(C(=O)O)Cc3ccccc3C2)cc1OCCc1cccc(C)c1 ; [Na+]]

(Compound 2a)

In some embodiments, the compound of Formula 2 is isolated prior to Step (2): acidification. In some embodiments, the compound of Formula 2 is purified prior to the acidification step.

In some embodiments, the compound of Formula 2 is not isolated prior to Step (2): acidification. In some embodiments, the reaction mixture of Step (1) is reverse added onto the reaction mixture used in Step (2).

Step (2): Preparation of Crystalline Form 1 of Compound I (Acidification)

In some embodiments, a compound of Formula 2 undergoes an acidification reaction to provide the free acid Compound I. In some embodiments, a compound of Formula 2 undergoes an acidification reaction to provide the crystalline form 1 of Compound I. In some embodiments, crystalline form 1 of Compound I is isolated directly from the acidification reaction mixture.

Initial Optimization for the Preparation of Crystalline Form 1 of Compound I

Previous methods for the preparation of crystalline form 1 of Compound I comprised:
  a. adding citric acid to the reaction mixture of Step (1) to quench the excess metal hydroxide base, and carefully control pH to neutral;
  b. quickly thereafter adding seeds of crystalline form 1 of compound I (e.g., 2%);
  c. aging this mixture for precisely 15 minutes;
  d. quickly adding additional citric acid to crystallize Compound 1 into crystalline form 1.

Despite this processes ability to produce crystalline form 1, the process provides many manufacturing challenges and requires close monitoring due to the extremely tight window of conditions required.

For example, in some instances, temperatures above 50° C. result in isolation of crystalline form 2, and not crystalline form 1. In some instances, temperatures below 20° C. result in fast spontaneous crystallization resulting in a mixture of polymorphs. Further, In some instances temperatures above 35° C. provide crystalline particles less than 500 μm is size and in a monomodal particle size distribution; while temperatures below 20° C. result in a bimodal partical size distribution with particle sizes>500 μm. As a result, the temperature in the previously reported acidification and crystallization process must be tightly controlled at 40° C. throughout the process in order to obtain crystalline form 1.

In some instances of the original process, a pH of less than 6.9 after quenching the base also results in isolation of crystalline form 2. In some instances, if the pH of the reaction mixture is dropped too quickly, Compound I spontaneously crystallizes, which can lead to a mixture of polymorphic forms, or to form 2. Additionally, if the pH is too high when the seeds are added, the seeds will dissolve leading to no benefit of seeding. As a result slow and careful control of pH is required throughout the process in order to obtain crystalline form 1.

Additionally, in some instances even with the tight temperature and pH control, an unseeded mixture kept at 40° C. can lead to spontaneous crystallization of crystalline form 2. In other instances, a mixture seeded with 2% to 5% w/w seeds kept at 20° C. results in crystalline form 2. A very slow conversion of undesired form 2 to desired from 1 can occur with slurrying the mixture over long periods at 20° C., but this is not a good manufacturing solution.

Accordingly, this original process relies on preventing a supersaturated solution of Compound I from self-crystallizing into mixtures of polymorphs, using a tight window of pH and temperature conditions throughout the process. At the neutral/acidic pH needed to form the free acid Compound I, the compound is highly insoluble and the final hypersaturated solutions are thermodynamically unstable and prone to vigorous and spontaneous crystallization into a mixture of polymorphs.

Improved Preparation of Crystalline Form 1 of Compound I

In some embodiments, Crystalline Form 1 of Compound I is prepared by a process comprising adding a mixture comprising a compound of Formula 2:

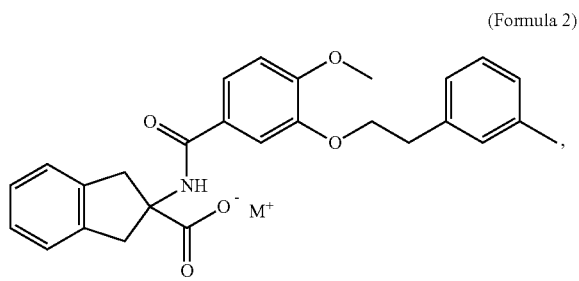

(Formula 2)

wherein M⁺ is Na⁺, K⁺, or Li⁺;
in a suitable solvent onto a slurry of citric acid.

In some embodiments, Crystalline Form 1 of Compound I is characterized as having: an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Kα) radiation.

In some embodiments, the suitable solvent tetrahydrofuran, methanol, ethanol, ethylene glycol, acetonitrile, water, or a combination thereof. In some embodiments, the suitable solvent is a mixture of methanol and water.

In some embodiments, the mixture comprising the compound of Formula 2 is a solution. In some embodiments, the mixture comprising a compound of Formula 2 is obtained by saponification of the ester moiety of the compound of Formula 1:

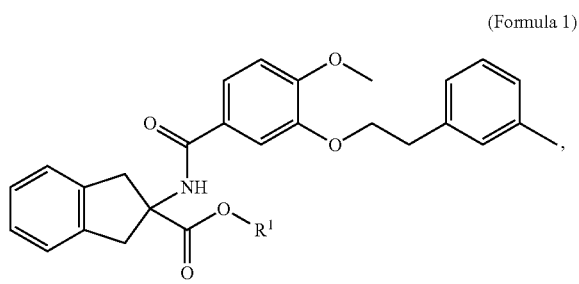

(Formula 1)

wherein R¹ is methyl or ethyl in a suitable solvent. In some embodiments, the mixture comprising the compound of Formula 2 is the reaction mixture obtained from the saponification reaction as described above.

In some embodiments, the slurry of citric acid comprises citric acid in a suitable solvent. In some embodiments, the slurry of citric acid comprises citric acid in a solvent selected from tetrahydrofuran, methanol, ethanol, ethylene glycol, acetonitrile, water, or a combination thereof. In some embodiments, the slurry of citric acid comprises citric acid in methanol.

In some embodiments, the slurry comprises at least 1.0 equivalent of citric acid relative to the amount of the compound of Formula 2. In some embodiments, the slurry comprises at least 1.0 equivalent of citric acid relative to the amount of the compound of Formula 1 used in a saponification reaction as described above. In some embodiments, the slurry comprises from about 1.2 equivalents to about 1.5 equivalents of citric acid relative to the amount of the compound of Formula 2. In some embodiments, the slurry comprises from about 1.2 equivalents to about 1.5 equivalents of citric acid relative to the amount of the compound of Formula 1 used in a saponification reaction as described above. In some embodiments, the concentration of the citric acid in the slurry is from about 0.5 M to about 1.5 M. In some embodiments, the concentration of the citric acid in the slurry is about 0.5 M, about 0.6 M, about 0.7 M, about 0.8 M, about 0.9 M, about 1.0 M, about 1.1 M, about 1.2 M, about 1.3 M, about 1.4 M, or about 1.5 M. In some embodiments, the concentration of the citric acid in the slurry is about 1.0 M. In some embodiments, the slurry of citric acid comprises about 1.32 equivalents of citric acid relative to the amount of the compound of Formula 2 in methanol at a concentration of about 1.0 M. In some embodiments, the slurry of citric acid comprises about 1.32 equivalents of citric acid relative to the amount of the compound of Formula 1 used in a saponification reaction as described above in methanol at a concentration of about 1.0 M.

In some embodiments, the slurry of citric acid further comprises seed crystals of crystalline form 1 of Compound I. In some instances, a seed crystal is a small crystal used as a base to grow a large single crystal. In some instances, crystals form slowly from random intermolecular interactions in the absence of seed crystals. In some instances, when the seed is placed in a saturated or supersaturated solution it acts as a nucleation site for crystallization of the desired from (e.g., crystalline form 1 of Compound I).

In some embodiments, the slurry of citric acid further comprises up to about 10% w/w of seeds of Crystalline Form 1 of Compound I. In some embodiments, the slurry of citric acid further comprises from 0% to about 5% w/w of seeds of Crystalline Form 1 of Compound I. In some embodiments, the slurry of citric acid further comprises from about 0.5% to about 5% w/w of seeds of Crystalline Form 1 of Compound I. In some embodiments, the slurry of citric acid further comprises about 0.5%, about 1.0%, about 1.5%, about 2.0%, about 2.5%, about 3.0%, about 3.5%, about 4.0%, about 4.5%, or about 5% w/w of seeds of Crystalline Form 1 of Compound I. In some embodiments, the % w/w is relative to the amount of expected Compound I. In some embodiments, the % w/w is relative to the amount of the compound of Formula 2. In some embodiments, the % w/w is relative to the amount of the compound of Formula 1 used in a saponification reaction as described above.

In some embodiments, the slurry of citric acid does not comprise any seed crystals of Crystalline Form 1 of Compound I.

In some embodiments, the slurry of citric acid is heated prior to addition of the mixture comprising a compound of Formula 2. In some embodiments, the slurry of citric acid is heated to about 40° C. In some embodiments, the temperature of the slurry is maintained at about 40° C. throughout addition of the mixture comprising a compound of Formula 2. In some embodiments, "about 40° C." means from 35° C. to 45° C. In some embodiments, "about 40° C." means from 37° C. to 43° C. In some embodiments, the temperature of the slurry is maintained at a temperature of 37° C. to 43° C. throughout addition of the mixture comprising a compound of Formula 2. In some embodiments, the temperature of the temperature of the slurry is throughout addition of the mixture comprising a compound of Formula 2 by slow addition of the mixture comprising a compound of Formula 2. In some embodiments, the mixture comprising a compound of Formula 2 is added onto the slurry of citric acid over about 1 hour, about 2 hours, about 3 hours, or more. In some embodiments, the mixture comprising a compound of Formula 2 is added onto the slurry of citric acid over about 2 hours. In some embodiments, "about 2 hours" means from about 1 h 30 min to about 2 h 30 min. In some embodiments, "about 2 hours" means from about 1 h 45 min to about 2 h 15 min. In some embodiments, "about 2 hours" means from 1 h 30 min to 2 h 30 min. In some embodiments, "about 2 hours" means from 1 h 45 min to 2 h 15 min. In some embodiments, the mixture comprising a compound of Formula 2 is added onto the slurry of citric acid over a period of time of 1 h 30 min to 2 h 30 min. In other embodiments, the mixture comprising the compound of Formula 2 is added onto the slurry of citric acid over a period of time of from about 10 minutes to about 120 minutes.

In some embodiments, after addition of the mixture comprising the compound of Formula 2 is added onto the slurry of citric acid, the resulting mixture is maintained, or aged, at a temperature of about 40° C. In some embodiments, "about 40° C." means from 35° C. to 45° C. In some embodiments, "about 40° C." means from 37° C. to 43° C. In some embodiments, the resulting mixture is maintained, or aged, for about 1 hour, about 2 hours, about 3 hours, or more. In some embodiments, the resulting mixture is aged for about 2 hours. In some embodiments, "about 2 hours" means from about 1 h 30 min to about 2 h 30 min. In some embodiments, "about 2 hours" means from about 1 h 45 min to about 2 h 15 min. In some embodiments, "about 2 hours" means from 1 h 45 min to 2 h 15 min. In some embodiments, the resulting mixture is aged for about 3 hours. In some embodiments, "about 3 hours" means from about 2 h 30 min to about 3 h 30 min. In some embodiments, "about 3 hours" means from about 2 h 45 min to about 3 h 15 min. In some embodiments, "about 3 hours" means from 2 h 45 min to 3 h 15 min. In some embodiments, after addition of the mixture comprising the compound of Formula 2 is added onto the slurry of citric acid, the resulting mixture is maintained at a temperature of about 40° C. for about 3 hours.

In some embodiments, the mixture is cooled before isolation. In some embodiments, the mixture is cooled to from about 0° C. to about 10° C. In some embodiments, the mixture is cooled to about 10° C. In some embodiments, "about 10° C." means from 5° C. to 15° C. In some embodiments, "about 50° C." means from 7° C. to 13° C. In some embodiments, the mixture is cooled to 7° C. to 13° C. prior to isolation In some embodiments, the mixture is quickly cooled. In other embodiments, the mixture is cooled slowly. In some embodiments, the mixture is cooled over about 1 hour, 2 hours, 3 hours, 4 hours, or more. In some embodiments, the cooled mixture is maintained at the lower temperature for a period of about 1 hour, 2 hours, 3 hours, 4 hours, or more. In some embodiments, the mixture is cooled to about 10° C. over a period of time of about 3 hours.

In some embodiments, crystalline form 1 of Compound I is isolated by filtration.

In some embodiments, the isolated crystalline form 1 of Compound I is washed with a suitable solvent. In some embodiments, the isolated crystalline form 1 of Compound I is washed with a suitable solvent once, twice, three time, four time, or more. In some embodiments, the isolated crystalline form 1 of Compound I is washed with a suitable solvent up to four times. In some embodiments, the suitable solvent used for the washes tetrahydrofuran, methanol, ethanol, ethylene glycol, acetonitrile, water, or a combination thereof. In some embodiments, the suitable solvent used for the washes is methanol, water, or a combination thereof. In some embodiments, each of the washes is performed with the same solvent. In other embodiments, some washes are performed with one suitable solvent, for example methanol, and other washes are performed with another suitable solvent, for example a 1:1 methanol/water mixture.

In some embodiments, the isolated crystalline form 1 of Compound I is dried. In some embodiments, the isolated crystalline form 1 of Compound I is dried under vacuum. In some embodiments, the isolated crystalline form 1 of Compound I is dried at an elevated temperature. In some embodiments, the isolated crystalline form 1 of Compound I is dried at a temperature of about 40° C. In some embodiments, the isolated crystalline form 1 of Compound I is dried at a temperature of about 35° C. to about 45° C. In some embodiments, the isolated crystalline form 1 of Compound I is dried under vacuum at a temperature from about 35° C. to about 45° C. In some embodiments, the isolated crystalline form 1 of Compound I is dried under vacuum at a temperature from about 35° C. to about 45° C., and for a time of from about 3 hours to about 36 hours. In some embodiments, the isolated crystalline form 1 of Compound I is dried under vacuum at a temperature of about 40° C. for about 16 hours.

In some embodiments, isolated Compound I is isolated as crystalline form 1 and shows no evidence of other forms. In some embodiments, isolated Compound I is isolated as crystalline form 1 and shows no evidence crystalline form 2.

In some embodiments, the reverse addition of the mixture comprising a compound of Formula 2 onto the slurry comprising citric acid is more robust, scaleable, and predictable, as well as less expensive than, the previous process of adding acid to the compound of Formula 2. The improved process works to provide crystalline form 1 without the tight parameter conditions that are still unpredictable in the earlier processes.

In some embodiments, crystalline form 1 of Compound I is synthesized as outlined in the Examples.

Described herein is a pharmaceutical composition of Compound I substantially free of impurities. In some embodiments, the pharmaceutical composition is substantially free of Compound I impurities. In some embodiments, the pharmaceutical composition comprises less than about 1% w/w of Compound I impurities. In some embodiments, the pharmaceutical composition comprises less than about 1% w/w, less than about 0.75% w/w, less than about 0.50% w/w, less than about 0.25% w/w, less than about 0.20% w/w, less than about 0.15% w/w, less than about 0.10% w/w, or less than about 0.05% w/w of Compound I impurities. In some embodiments, the amount of Compound I impurities is undetectable. In some embodiments, the amount of Compound I impurities is undetectable by NMR, HPLC, or the like.

In some embodiments, the Compound I impurities comprise one or more degradants of Compound I. In some embodiments, the Compound I impurities comprise one or more intermediates used in the synthesis of Compound I. In some embodiments, the Compound I impurities are selected from:

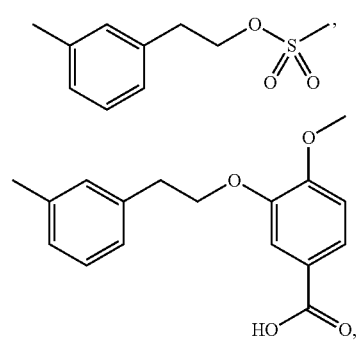

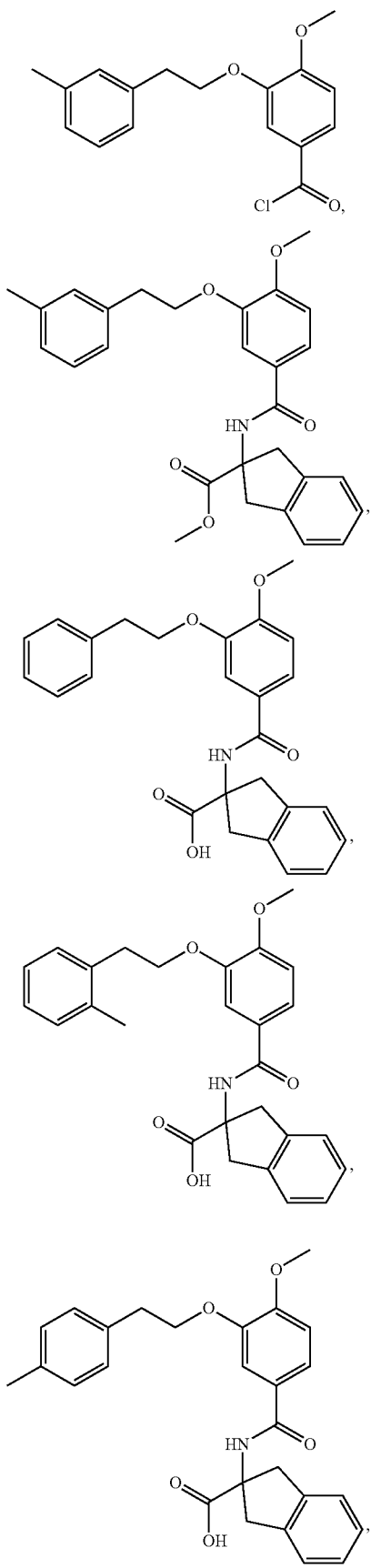

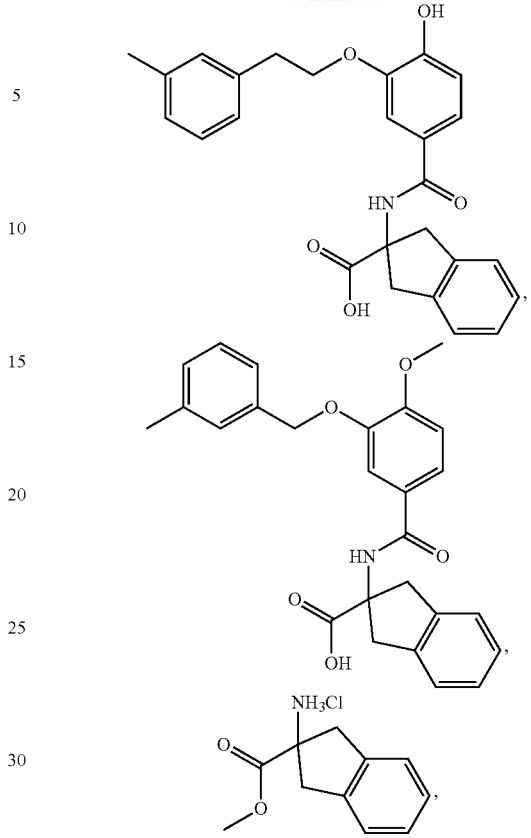

or a combination thereof.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use*, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts of Compound I are obtained by reacting Compound I with a base. In some embodiments, the base is an inorganic base.

In such situations, the acidic proton of Compound I is replaced by a metal ion, e.g., lithium, sodium, potassium, magnesium, or calcium. Acceptable inorganic bases used to form salts with Compound I include, but are not limited to, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, or magnesium salt. In some embodiments, described herein is the sodium salt of Compound I.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound I, comprise an organic solvent(s). In some embodiments, compositions comprising Compound I include a residual amount of an organic solvent(s). In some embodiments, compositions comprising Compound I comprise a residual amount of a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

In some embodiments, the compositions comprising Compound I include a detectable amount of an organic solvent. In some embodiments, the organic solvent is a Class 3 solvent.

In other embodiments are compositions comprising Compound I wherein the composition comprises a detectable amount of solvent that is less than about 1%, wherein the solvent is selected from acetone, 1,2-dimethoxyethane, acetonitrile, ethyl acetate, tetrahydrofuran, methanol, ethanol, heptane, and 2-propanol. In a further embodiment are compositions comprising Compound I wherein the composition comprises a detectable amount of solvent which is less than about 5000 ppm. In yet a further embodiment are compositions comprising Compound I, wherein the detectable amount of solvent is less than about 5000 ppm, less than about 4000 ppm, less than about 3000 ppm, less than about 2000 ppm, less than about 1000 ppm, less than about 500 ppm, or less than about 100 ppm.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering," "administration," and the like, as used herein, refer to the methods that may be used to enable delivery of compounds or compositions to the desired site of biological action. These methods include, but are not limited to oral routes.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds disclosed herein, or a pharmaceutically acceptable salt thereof, are used in the preparation of medicaments for the treatment of diseases or conditions in a mammal that would benefit from modulation of $LPA_1$ receptor activity. Methods for treating any of the diseases or conditions described herein in a mammal in need of such treatment, involves administration of pharmaceutical compositions that include at least one compound disclosed herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In any of the aforementioned aspects are further embodiments in which the effective amount of the compound disclosed herein, or a pharmaceutically acceptable salt thereof, is: (a) systemically administered to the mammal; and/or (b) administered orally to the mammal.

In some embodiments, compound I, or a pharmaceutically acceptable salt thereof, is administered is dose selected from about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, and about 400 mg. In some embodiments, the dose is administered once a day. In some embodiments, the dose is administered twice a day.

EXAMPLES

Abbreviations:
Aq or aq: aqueous;
ACN or MeCN: acetonitrile;
DCM: dichloromethane;
DSC: differential scanning calorimetry;
DVS: dynamic vapor sorption;
Et: ethyl;
EtOAc: ethyl acetate;
EtOH: ethanol;
equiv or eq.: equivalents;
FTIR: Fourier transform infrared
h or hr: hour;
hrs: hours;
HPLC: high-performance liquid chromatography;
LC-MS or LCMS or LC/MS: liquid chromatography-mass spectrometry;
M: molar;
MEK: methyl ethyl ketone;
Me: methyl;
MeOH: methanol;
Me-THF or methyl THF: 2-methyltetrahydrofuran;
mins or min: minutes;
NaOH: sodium hydroxide;
NMR: nuclear magnetic resonance;
RH: relative humidity;
rt or RT: room temperature;
SCXRD: single crystal x-ray diffraction;
ssNMR: solid state nuclear magnetic resonance;
TGA: thermogravimetic analysis;
THF: tetrahydrofuran;
vol: volume, typically used for reaction volume or ratio of solvents;
w/w: weight ratio; and
XRPD: X-ray powder diffraction.

The following examples are provided for illustrative purposes only and not to limit the scope of the claims provided herein.

Example 1: Preparation of 2-(4-methoxy-3-(3-methylphenethoxy)benzamido)-2,3-dihydro-1H-indene-2-carboxylic acid (Compound I)

The preparation of Compound I has been previously described (see, WO 2009/135590, U.S. Pat. Nos. 8,362,073, 8,445,530, 8,802,720, 9,328,071, each of which is incorporated by reference in its entirety).

Example 2: Preparation of Crystalline Form 1 of Compound I—Initial Optimized Process The preparation of crystalline form 1 of Compound I has been previously described (see, International Patent Application No. PCT/IB2021/000594, and U.S. patent application Ser. No. 17/463,369, each of which is incorporated by reference in its entirety). The preparation of crystalline form 1 of Compound I comprises the following steps:

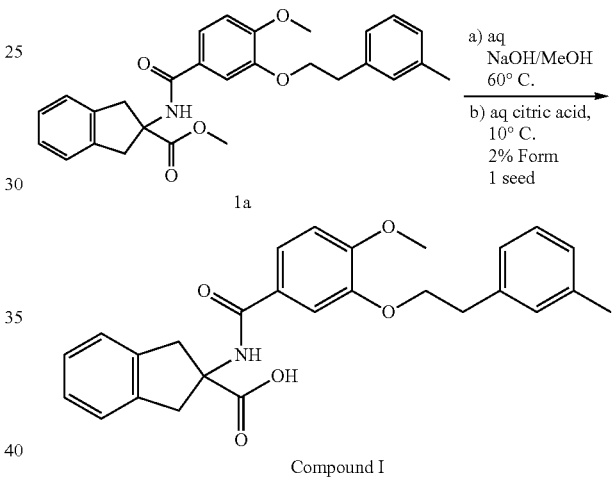

a) Saponification: Methyl 2-(4-methoxy-3-(3-methylphenethoxy)benzamido)-2,3-dihydro-1H-indene-2-carboxylate (1a, 10 g, 22 mmol, 1 eq) was dissolved in methanol (164 mL, 1.64 vol) and was heated to 50° C. with stirring. Aqueous NaOH (1 M, 26 mL, 1.21 eq) was added to the stirred solution over 30 min followed by water (3 mL, 0.3 vol). The reaction was stirred at 60° C. for 3 h, at which point LCMS showed complete reaction of 1a. The reaction mixture was cooled to 20° C. and filtered to remove insoluble material. The pH of the resultant solution was 13.2.

b) Acidification/Crystallization: The solution was acidified with 1 M citric acid (aq) to pH 7.5. The solution was seeded with crystals of Form 1 (2% by mass), cooled to 10° C. over 3 hrs, and was kept at 10° C. for 1 hr. The resulting suspension was filtered and solids were washed with 1:1 water:methanol (2×5 vol) followed by methanol (2×5 vol). The solid was dried in a vacuum oven at 40° C. to yield Compound I (9.2 g, 95%, Form 1 by XRPD).

Example 3: Large Scale Preparation of Crystalline Form 1 of Compound I

The process of Example 2 was repeated on kilogram scale, and manufacturing challenges for the reliable production of Form 1 were identified. Control of polymorphism for Compound I is difficult and requires tightly controlled window of conditions to yield Form 1. At neutral/acidic pH, Compound I is highly insoluble in most solvents, therefore hyper-saturated solutions (final stage of the manufacture) are thermodynamically unstable and prone to vigorously and spontaneously (i.e., uncontrollably) crystallize as mixtures of polymorphs.

Precise control of pH through sequential addition of citric acid is required: first careful addition of citric acid to bring pH to exact neutral (i.e. quench excess NaOH); then the reaction is seeded with Form 1; then a second addition of citric acid to bring pH to acid and release free carboxylic acid Compound I. If the pH is too high during this process, it will lead to dissolution of the seeds, and too low pH will trigger uncontrolled crystallizations.

Precise control of temperature is also required during this process. If the temperature is too low (e.g., about 20° C.), a fast crystallization is triggered yielding mixtures of Form 2 and Form 1. Temperatures above about 40° C. will favor Form 2. A "sweet spot (yet still precarious)" at 40° C., with appropriate optimized seeding was found. A fine balance between temperature/seeding revealed a criticality of conditions: left unseeded, the solution of Compound I will spontaneously crystallize. Furthermore, spontaneous crystallization at 40° C. again can lead to Form 2.

The process of Example 2 relies on preventing a supersaturated solution of Compound I from self-crystallizing into mixtures of polymorphs, using a tight window of temperature and pH conditions.

a) Saponification: Compound 1a (1.00 equiv) and methanol (16.40 V) are charged into Reactor A at a target temperature of 20° C. (acceptable limits: 17-23° C.). The mixture is heated to a target temperature of 50° C. (47-53° C.) and a 1 M sodium hydroxide solution (1.21 equiv) is added keeping the temperature around 50° C. (47-60° C.). The sodium hydroxide transfer line is rinsed with purified water (0.22 V), and the resulting reaction mixture is heated 60° C. (57-63° C.) and stirred at 60° C. (57-63° C.) for 3 h (2 h 45-3 h 15). The reaction progress is monitored and if remaining starting material is >1.0%, the reaction time is extended for 1 h and resampled. Once the reaction is completed, the reaction mixture comprising Compound 2a is cooled to 20° C. (17-23° C.). The resulting solutions is passed through a polish filter (0.3 μm) into Reactor B. Reactor A, the filter, and the transfer line are rinsed with methanol (0.50 C) and the solution is heated to 40° C. (37-43° C.).

b) Acidification/Crystallization: A citric acid solution (1M, ~0.127 equiv) is added to the solution in Reactor B (from step a). The pH of the solution is adjusted to pH 8.0 (7.5-8.5). If the pH stabilizes above 8.5, additional 1M citric acid solution is added in 0.05 equiv portions. A separate suspension of seed crystals of Crystalline Form 1 of Compound I (~2% w/w, 60 g/L) in methanol is added to the mixture in Reactor B and the resulting mixture is stirred for 15 min (15-25 min) at 40° C. (37-43° C.). After confirming that the seed crystals have not dissolved, the remaining 1M citric acid solution (~1.189 equiv) is added while maintaining the temperature at 40° C. (37-43° C.). The reaction mixture is stirred for 3 h (2 h 45-3 h 15) at 40° C. (37-43° C.), then is cooled to 10° C. (7-13° C.) within 3 h (2 h 45-3 h 15).

Isolation: The mother liquors are filtered and the cake is washed with methanol:purified water mixture (1:1), (2×5.00 V). The cake is washed further with methanol (2×5.00 V). The wet solid is dried to constant mass under max. vacuum at 40° C. (37-43° C.) for 3 h (3-36 h). The isolated solid is the undesired crystalline form 2 of Compound I, as confirmed by XRPD, DSC, and IR.

As demonstrated in this example, even with careful control of temperature, pH, and time, the process is very precarious.

Example 4: Improved Preparation of Crystalline Form 1 of Compound I—Reverse Addition onto Citric Acid

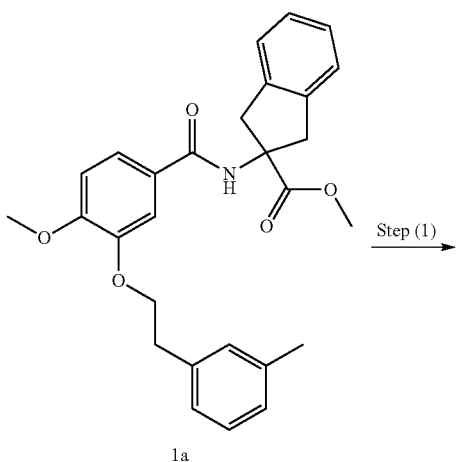

1a

Step (1)

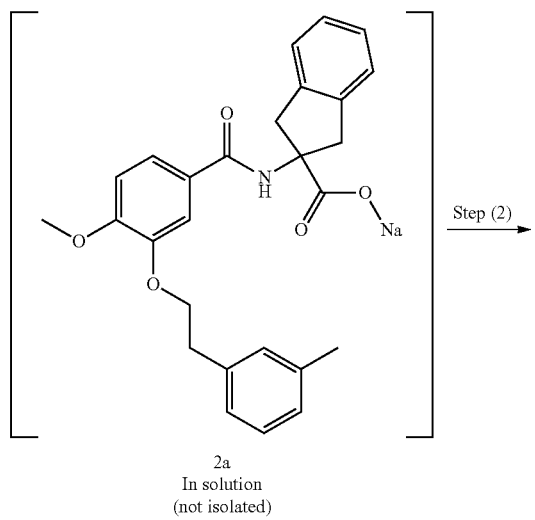

2a
In solution
(not isolated)

Step (2)

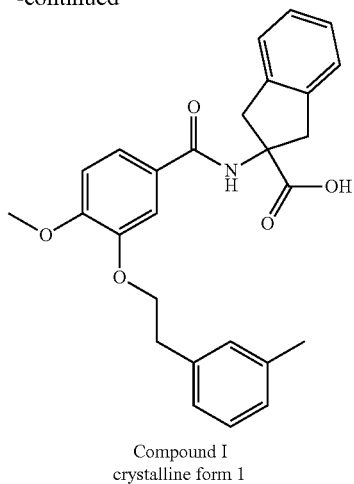

Compound I
crystalline form 1

Step (1)—Compound 2a: Compound 1a (1.00 equiv) and methanol (16.91 V) are charged into Reactor A at a target temperature of 20° C. (acceptable limits: 15-25° C.). The mixture is heated to a target temperature of 50° C. (47-53° C.) and a 1 M sodium hydroxide solution (1.21 equiv) is added keeping the temperature around 50° C. (47-60° C.). The sodium hydroxide transfer line is rinsed with purified water (0.12 V), and the resulting reaction mixture is heated 60° C. (57-63° C.) and stirred at 60° C. (57-63° C.) for 2 h (1 h 45-2 h 15). The reaction progress is monitored and if remaining starting material is >1.0%, the reaction time is extended for 1 h and resampled. Once the reaction is completed, the reaction mixture comprising Compound 2a is cooled to 40° C. (37-43° C.) to prepare for the next step.

Step (2)—Crystalline form 1 of Compound I: A 1M citric acid solution in methanol (1.36 equiv of citric acid) and seed crystals of Crystalline Form 1 of Compound I (1% w/w) are charged into Reactor B. The resulting mixture is heated to a target temperature of 40° C. (acceptable limits: 37-43° C.). The reaction mixture comprising Compound 2a from reactor A (Step (1)) is dosed through a 0.3 μm polish filter onto the citric acid mixture in reactor B within 2 h (1 h 30 min-2 h 30 min) keeping temperature at 40° C. (37-43° C.). The transfer line is rinsed with methanol (0.50 V). The resulting mixture is stirred for 3 h (2 h 30-3 h 30) at 40° C. (37-43 C), then is cooled to 10° C. (7-13° C.) within 3 h (2 h 30-3 h 30).

Isolation: The mixture is filtered and the wet cake is washed with 2 portions a mixture of methanol/purified water (1:1, 2×5.16 V) and then 2 portions of methanol (2×5.16 V). The wet solid is dried to constant mass under max. vacuum at 40° C. (35-45° C.) for 16 h (3-36 h).

The isolated solid is crystalline form 1 of Compound I. The crystalline form 2 is not detected.

Example 5: Process Parameter Study

The goal of this study was to test its robustness to consistently obtain polymorphic Form 1. To this end, the seed concentration, carboxylate addition rate and stirring speed were tested at low and high levels/rates. In an effort to generate larger crystals and facilitate filtration, the impact of temperature cycling was also tested. Only minor modifications were made to optimize the hydrolysis step with a reduction of the saponification duration, also limiting the time when potential hydrolysis of the product could occur. The stability of the Compound I suspension before isolation was then tested and the simulation of drying in a tumble drying was finally performed as for the two previous steps.

In total, 8 trials were performed on this step at the laboratory scale. The results are detailed in the following paragraphs.

Example 6: Robustness of the Inverse-Addition Crystallization

The promotion of different polymorphic forms is usually driven by solvent composition, temperature, impurities, degree of supersaturation or crystallization time. With the inverse addition of the carboxylate onto the citric acid solution, the product crashes out so crystallization time and degree of supersaturation is no longer parameters that need to be carefully controlled. Solvent composition is defined by the amount of methanol and water entering the process and are well controlled. Therefore, the amount of seed (Example 6a), the dosing time (Example 6b) and the stirring pattern (Example δc) were tested. Finally, to confirm the results, the trials with the most and the least favorable conditions towards target polymorph were repeated (Example 6d).

Results for these trials are in Table 1.

TABLE 1:1

| Trial | Seed % w/w | Carboxylate addition time min | Stirrer | Isolated Form |
|---|---|---|---|---|
| 1 | 1.0 | 120 | Pitched blade turbine[1] | 1 |
| 2 | 1.0 | 10 | Pitched blade turbine[1] | 1 |
| 3 | 1.0 | 120 | Half moon-shaped impeller[2] | 1 |
| 4 | 1.0 | 10 | Half moon-shaped impeller[2] | 1 |
| 5 | 0.5 | 120 | Pitched blade turbine[1] | 1 |
| 6[3] | 0.0 | 240 | Pitched blade turbine[1] | 1 |

[1]Axial + radial stirring
[2]Radial stirring
[3]Reworking of Compound I Form 2 stirred during 30 min at 20° C. with 1.25 equiv. NaOH 1M dosed onto 1.36 equiv. citric acid solution (inverse crystallization)

Example 6a: Seed Amount

The inverse-addition crystallization was successfully tested with 5% w/w seed. Since the carboxylic acid precipitates with a large excess of seed as the carboxylate is dosed onto the citric acid solution, reduction of the initial seed bed was studied up to 1.0% w/w. Even with the "worst case conditions" regarding addition time and stirring (see Table 1), Crystalline Form 1 was consistently obtained. Further reductions to 0.5% w/w, and without seed at all, were performed and again Crystalline Form 1 was obtained consistently.

Example 6b: Carboxylate Solution Addition Time

The carboxylate dosage is intended to be performed on a regular manner over about two hours in production. In case of a transfer issue, a very fast dosage was tested in Trial 2, i.e. 10 min with a full opening of the addition funnel. The seed loading was kept at 1% w/w. Trial 2 yielded crystalline form 1 (based on IR) and typical impurity profile of the isolated product. The duration of addition of the carboxylate solution onto the seed-containing citric acid solution did not impact the polymorphic form for the tested extremes (10 and 120 min) (see Table 1).

Example 6c: Impact of Stirring

Local hotspots could potentially affect the polymorph, due to a fast dosage, a poor stirring or a combination of these two factors. For this reason, the impact of the stirring was tested. Axial flow stirrers (pitched blade turbines) and radial stirrers (half moon-shaped impellers) were investigated. The seed amount was maintained at 1% w/w and the carboxylate solution was dosed over 2 h. Again, polymorph Form 1 (based on IR) and typical impurity profile of the isolated product were obtained in all studies (see Table 1). A stirring with lower mixing efficiency had no impact the polymorphic form of Compound I crystals.

Example 6d: Replicate Trials

Two duplicate trials were performed with the standard and the "worst case" conditions (Table 2). In both cases, Crystalline Form 1 was obtained.

TABLE 2

| Trial | Seed % w/w | Carboxylate addition time min | Stirrer | Isolated Form |
|---|---|---|---|---|
| 7 | 1.0 | 10 | Radial stirring | 1 |
| 8 | 0.5 | 120 | Axial + radial stirring | 1 |

These results confirm the robustness of the inverse crystallization process. The process robustness was experienced in terms of stirring efficiency and carboxylate dosing time. A repetition of the two trials with the best and less favorable conditions confirmed the results already obtained. The Form 1 polymorph was obtained in both cases with an in-spec impurity profile.

Example 7: X-Ray Powder Diffraction (XRPD)

Although the following diffractometers were used, other types of diffractometers could be used. Furthermore, other wavelengths could be used and converted to the Cu Kα. In some embodiments, Synchrotron Radiation X-Ray Powder Diffraction (SR-XRPD) can be used to characterize the crystalline forms.

"Characteristic peaks", to the extent they exist, are a subset of observed peaks and are used to differentiate one crystalline polymorph from another crystalline polymorph (polymorphs being crystalline forms having the same chemical composition). Characteristic peaks are determined by evaluating which observed peaks, if any, are present in one crystalline polymorph of a compound against all other known crystalline polymorphs of that compound to within ±0.2° 2-Theta.

STOE Stadi-P Transmission Diffractometer

X-ray powder diffractions were performed with STOE Stadi-P transmission diffractometers using Cu-Kα$_1$ radiation. Linear position sensitive detectors were used for capillary measurements and for samples in flat preparation, while image plate position sensitive detectors (IP-PSDs) were used for temperature-resolved XRPD, humidity-resolved XRPD and for robot samples in 96-well plates. The measured data was visualized and evaluated with the Software WinXPOW V2.12.

The 2-Theta peak values that are provided for the XRPD are within ±0.2° 2-Theta.

Characterization of Solid-State Forms of Compound I

Figure 5:
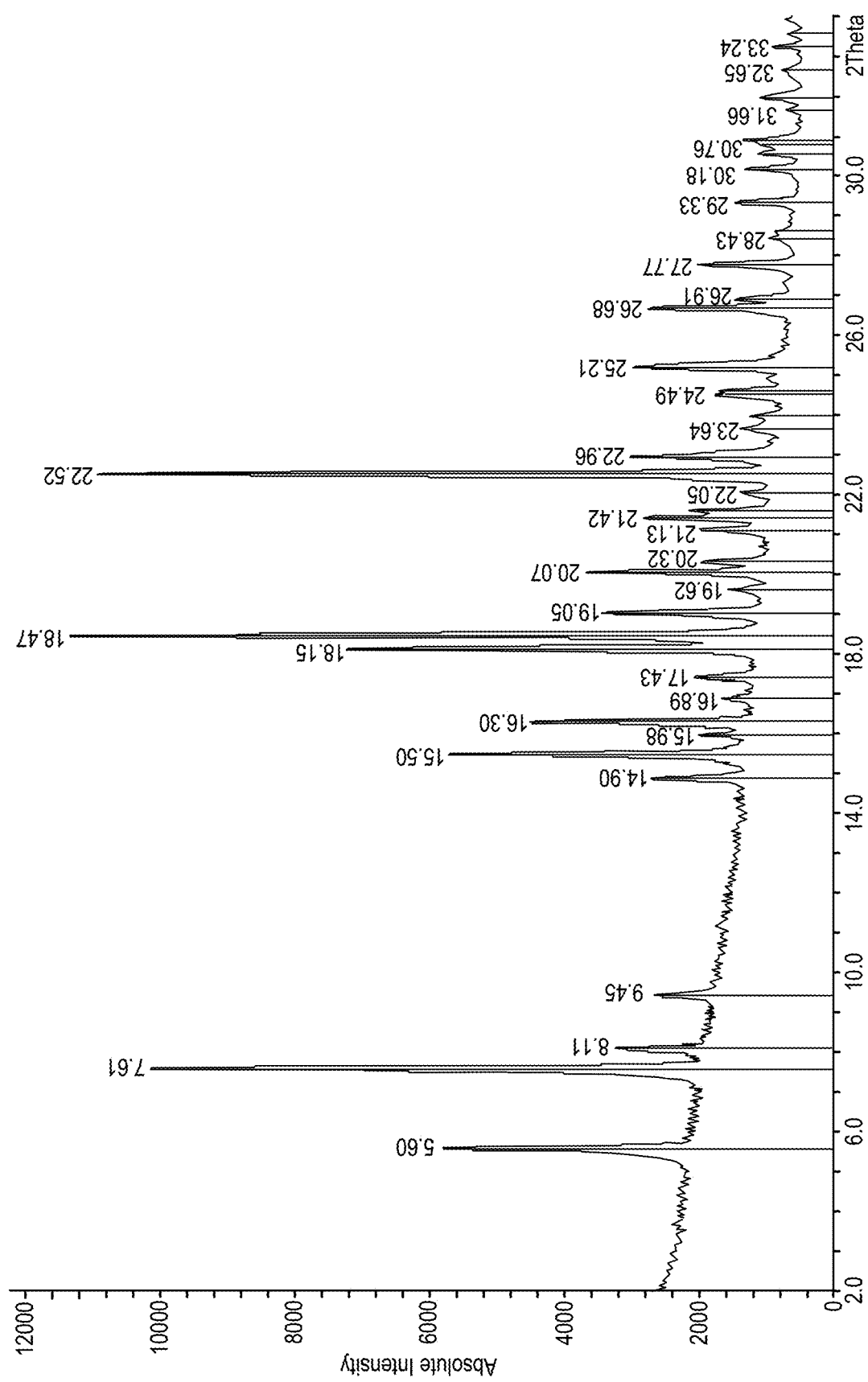
FIG. 5 shows the X-ray powder diffraction (XRPD) pattern of Form 2.
Figure 11:
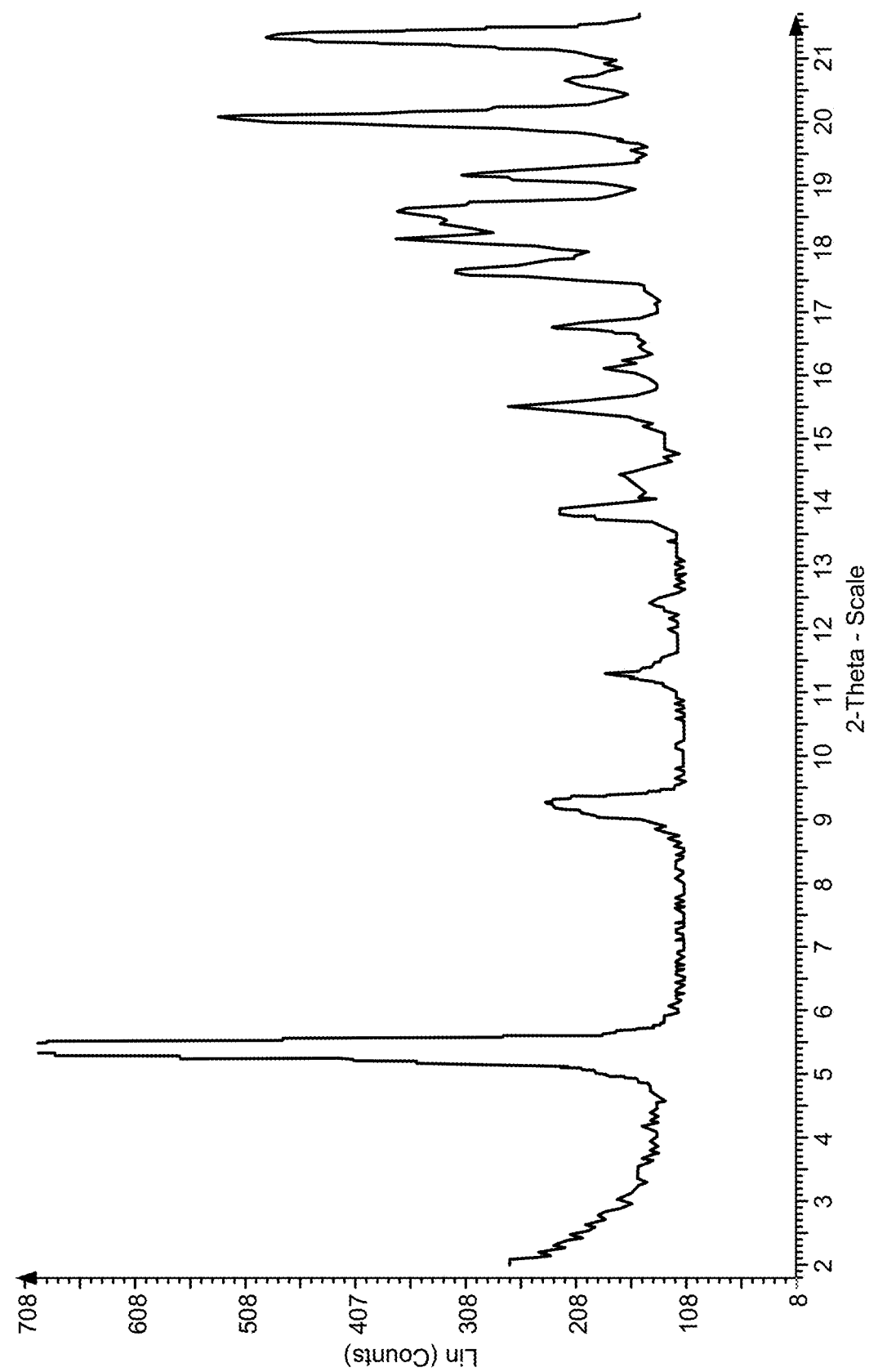
FIG. 11 shows the X-ray powder diffraction (XRPD) pattern of Form 4.

The X-Ray powder diffraction pattern for crystalline Form 1 of Compound I is displayed in FIG. 1. The X-Ray powder diffraction pattern for crystalline Form 2 of Compound I is displayed in FIG. 5. The X-Ray powder diffraction pattern for crystalline Form 3 of Compound I is displayed in FIG. 8. The X-Ray powder diffraction pattern for crystalline Form 4 of Compound I is displayed in FIG. 11.

Characterization of Crystalline Form 1 of Compound I

The X-Ray powder diffraction pattern for crystalline Form 1 of Compound I is displayed in FIG. 1. Characteristic XRPD peaks include: 5.2±0.2° 2-Theta, 9.0±0.2° 2-Theta, 14.4±0.2° 2-Theta, and 17.7±0.2° 2-Theta.

Characterization of Crystalline Form 2 of Compound I

Figure 6:
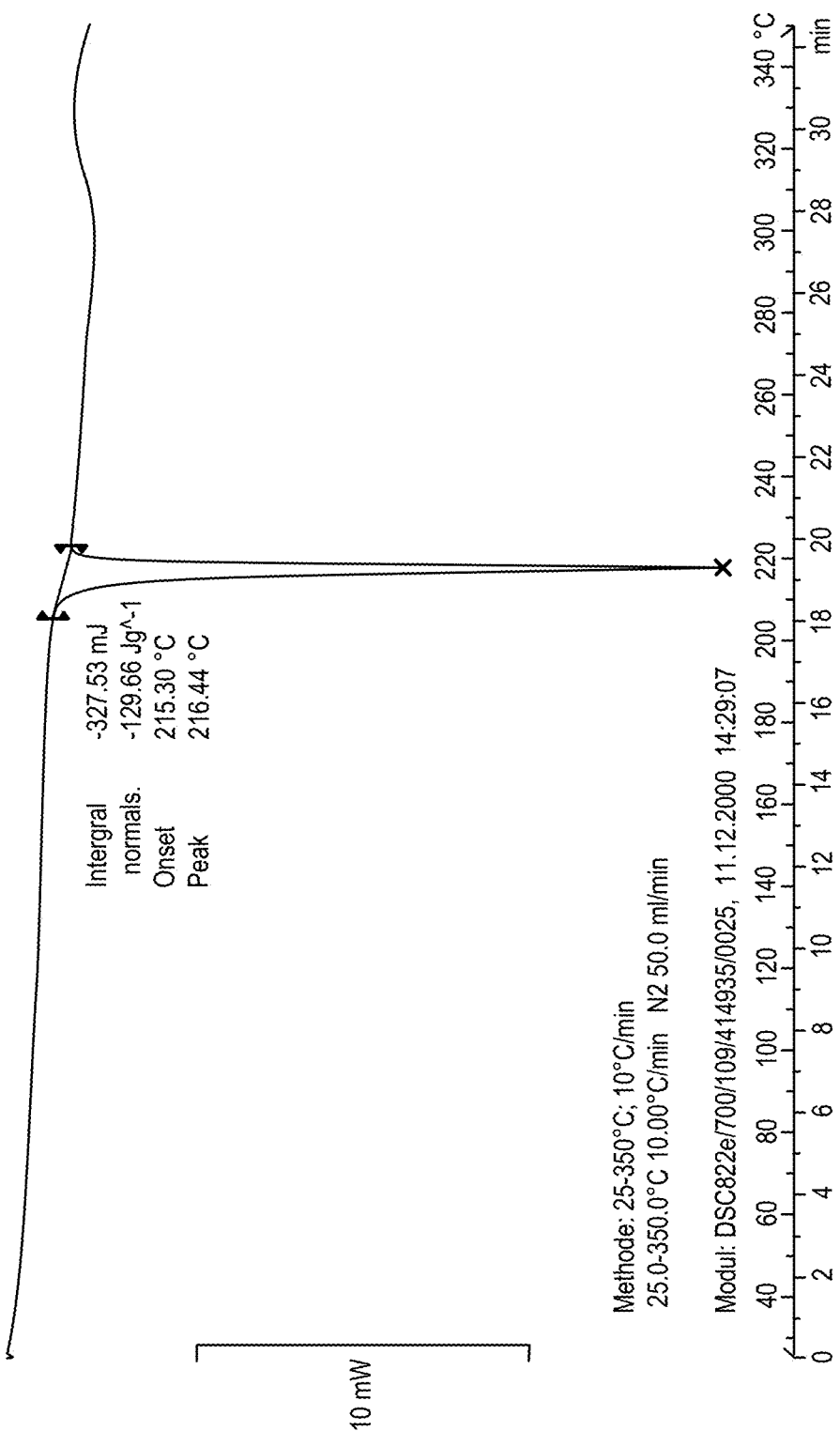
FIG. 6 shows the Differential Scanning Calorimetry (DSC) thermogram of Form 2.

The X-Ray powder diffraction pattern for crystalline Form 2 of Compound I is displayed in FIG. 6. Characteristic XRPD peaks include: 5.6±0.2° 2-Theta, 7.6±0.2° 2-Theta, 8.1±0.2° 2-Theta, 9.4±0.2° 2-Theta, 14.9±0.2° 2-Theta, and 16.3±0.2° 2-Theta.

Characterization of Crystalline Form 3 of Compound I

Figure 8:
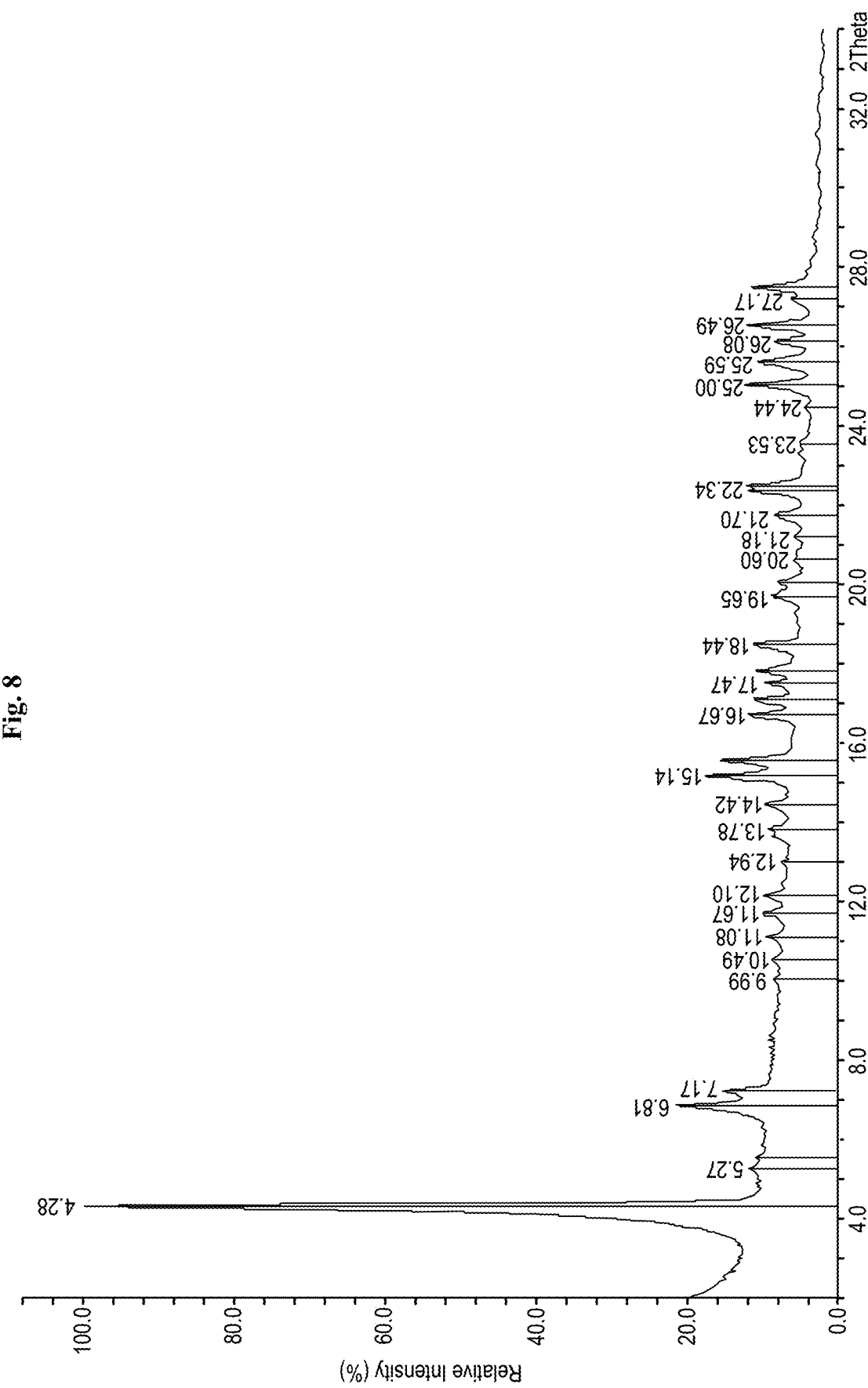
FIG. 8 shows the X-ray powder diffraction (XRPD) pattern of Form 3.

The X-Ray powder diffraction pattern for crystalline Form 3 of Compound I is displayed in FIG. 8. Characteristic XRPD peaks include: 4.2±0.2° 2-Theta, 6.8±0.2° 2-Theta, 15.1±0.2° 2-Theta, 25.0±0.2° 2-Theta, 25.5±0.2° 2-Theta, and 26.4±0.2° 2-Theta.

In some embodiments, measurements on independently prepared samples on different instruments may lead to variability which is greater than ±0.2° 2-Theta. Independently prepared samples of crystalline Forms 1 and 2 were characterized on three additional diffractometers.

Malvern Panalytical Empyrean Diffractometer

Instrument: Malvern Panalytical

Type: Empyrean with a Pixcel 1D Detector, a Copper XRD tube, a theta-theta goniometer and a sample changer.

Characterization of Crystalline Form 1 of Compound I

Figure 15:
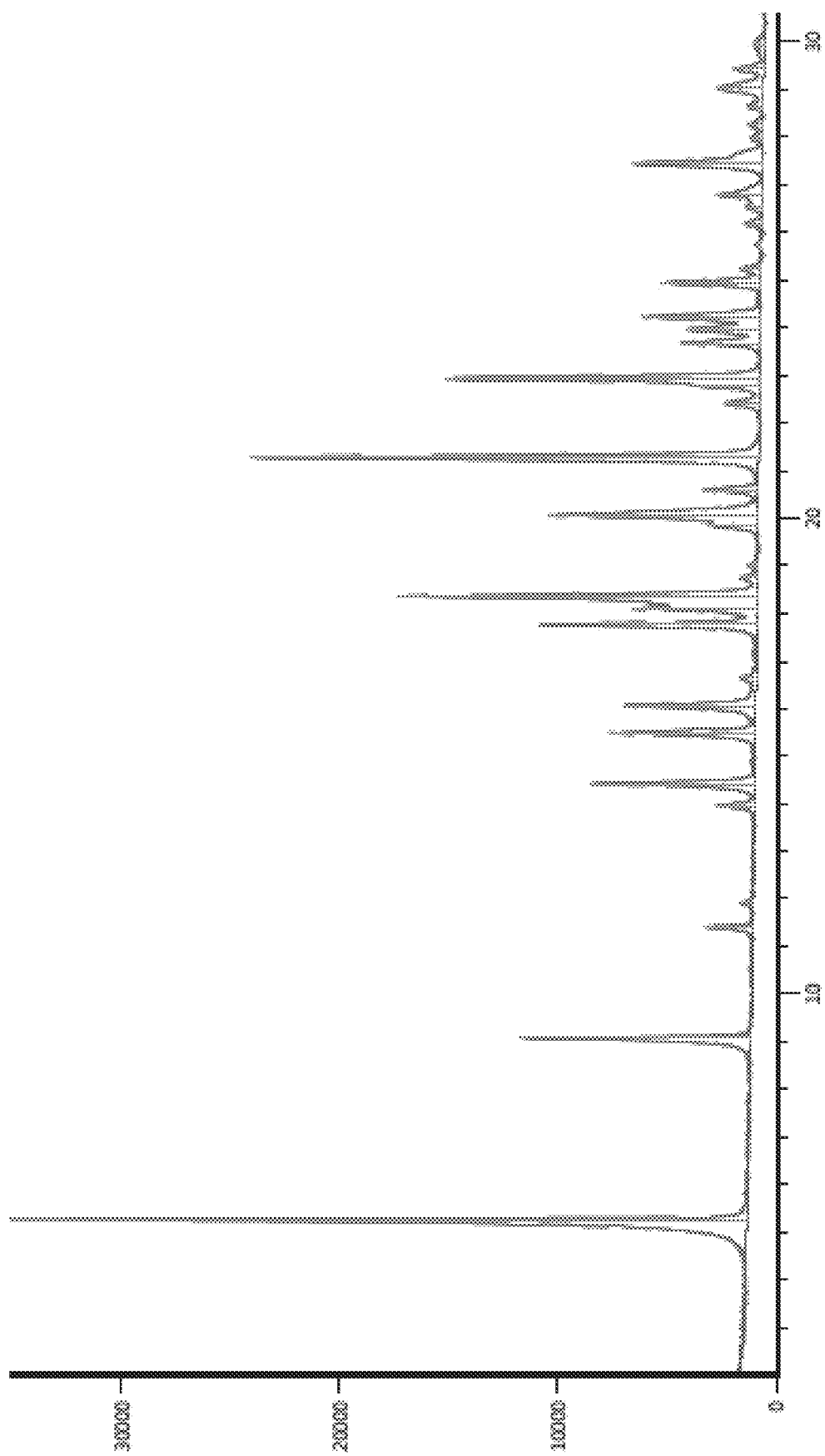
FIG. 15 shows the XRPD pattern of Form 1 obtained with the Malvern Panalytical Empyrean diffractometer.

The X-Ray powder diffraction pattern for crystalline Form 1 of Compound I is displayed in FIG. 15. Characteristic XRPD peaks include: 5.2±0.2° 2-Theta, 9.0±0.2° 2-Theta, 14.4±0.2° 2-Theta, and 17.7±0.2° 2-Theta.

Characterization of Crystalline Form 2 of Compound I

Figure 16:
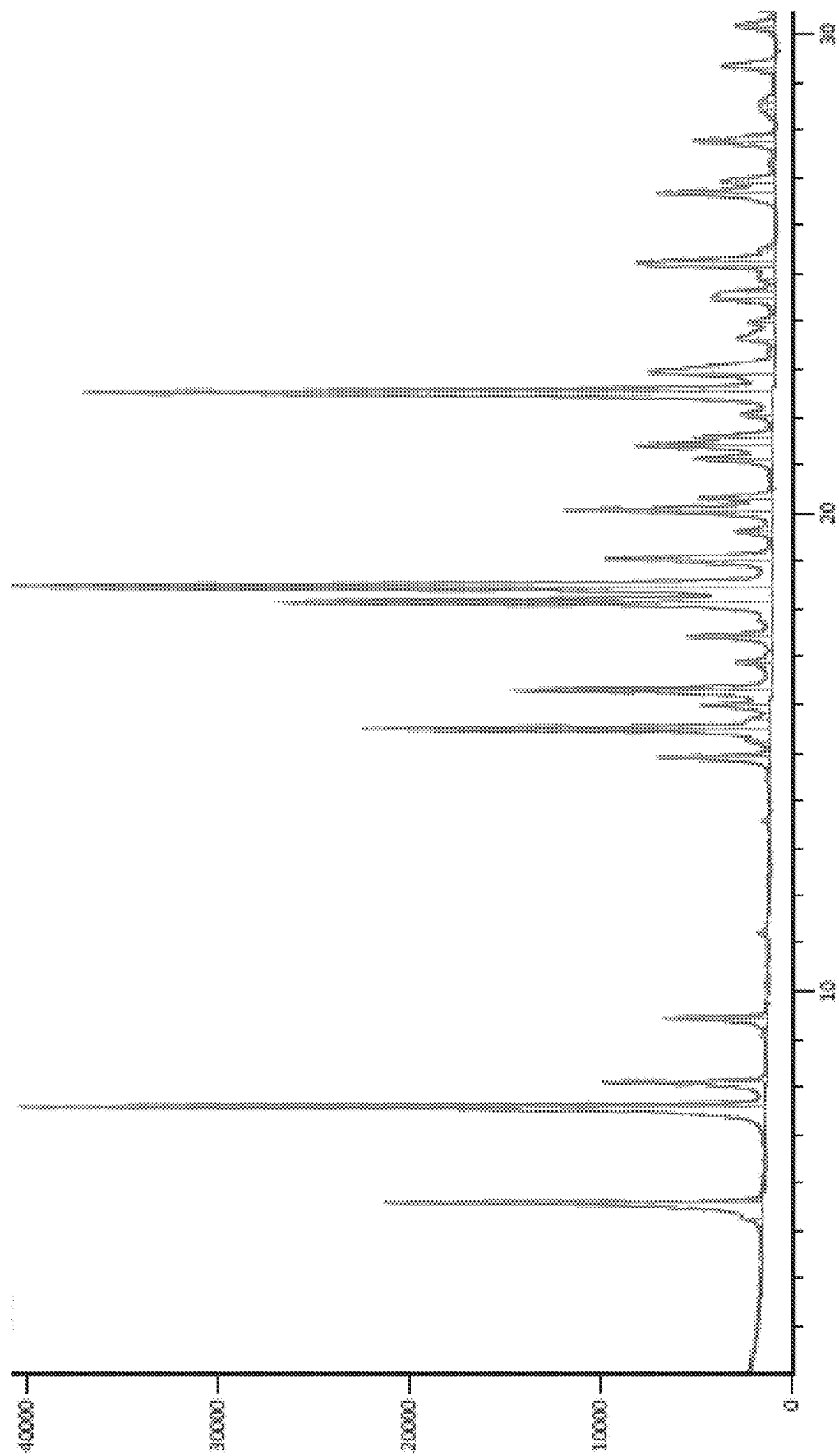
FIG. 16 shows the XRPD pattern of Form 2 obtained with the Malvern Panalytical Empyrean diffractometer.

The X-Ray powder diffraction pattern for crystalline Form 2 of Compound I is displayed in FIG. 16. Characteristic XRPD peaks include: 5.6±0.2° 2-Theta, 7.6±0.2° 2-Theta, 8.1±0.2° 2-Theta, 9.4±0.2° 2-Theta, 14.8±0.2° 2-Theta, and 16.2±0.2° 2-Theta.

Stoe Stadi P, G.52.SYS.S072

Equipment and Measurement Parameters

| | |
|---|---|
| Diffractometer: | Stoe Stadi P, G.52.SYS.S072 |
| Sample holders: | Stoe transmission sample holder, sample between two acetate foils with a 0.4 mm metal washer in between |
| Evaluation software: | WinXPOW by Stoe |

The X-ray diffraction pattern was recorded with the following instrumental parameters:

| | |
|---|---|
| Radiation: | Cu Kα1; 40 kV, 40 mA |
| Collimator: | 0.5 × 10 mm |
| Detector: | Mythen1K |
| Detector distance: | resulting to 0.01°(2θ) intrinsic resolution |
| Monochromator: | Ge, curved monochromator |
| Sample rotation | 1 rps |
| Scan range: | at least 2-40°(2θ) |
| Step size: | 0.020°(2q) |
| Detector Step time: | 48 s |
| Detector step: | 1°(2q) |

Figure 17:
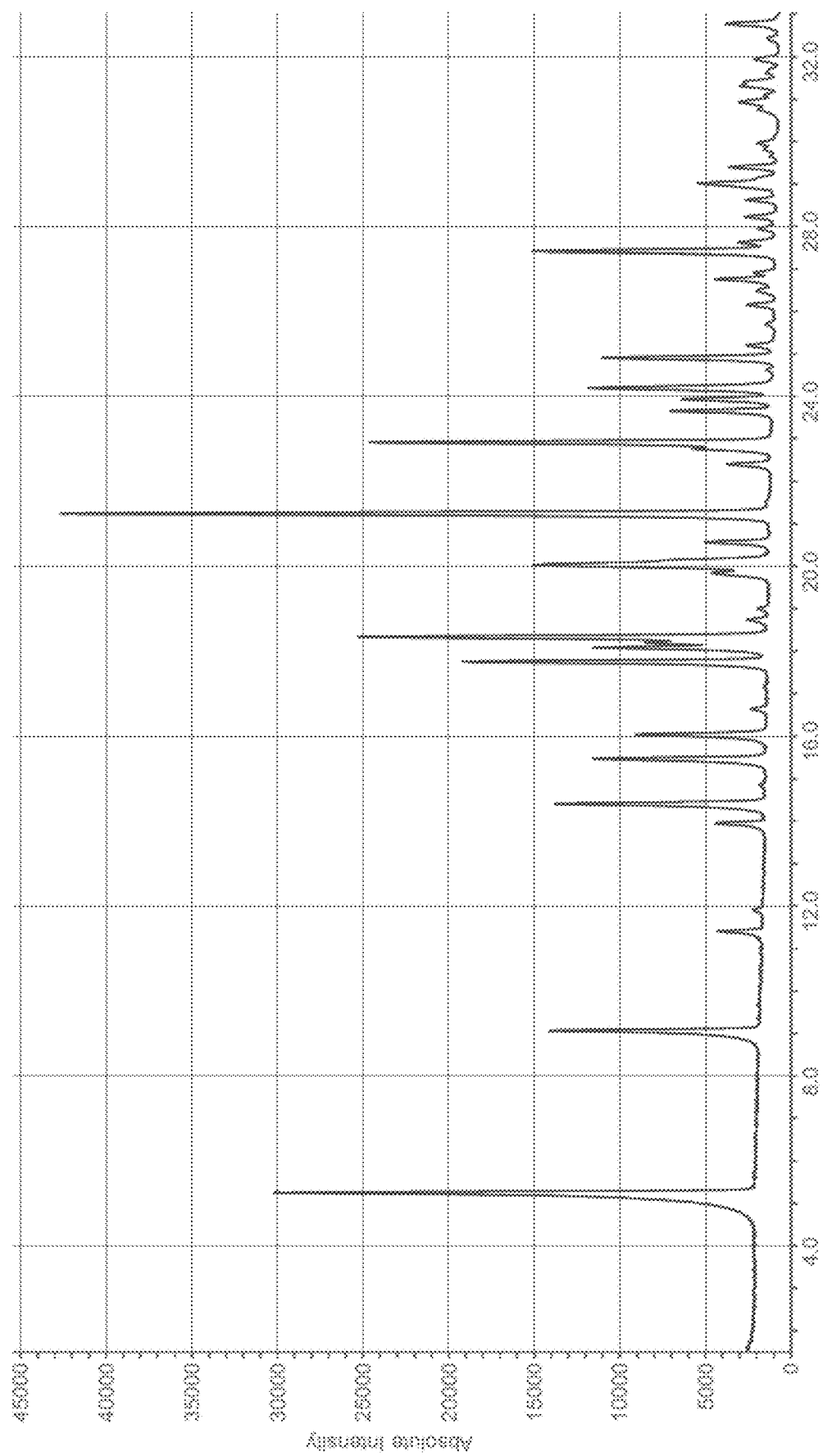
FIG. 17 shows the XRPD pattern of Form 1 obtained with the Stoe Stadi P, G.52.SYS.S072 diffractometer.

Sample preparation: The cylindrical volume determined by the washer and the two sheets of foil was slightly overfilled with a small quantity of the sample and then smoothed with two glass slides to obtain a disk of powder. This specimen was then secured into a Ni-coated metal sample holder Characterization of Crystalline Form 1 of Compound I The X-Ray powder diffraction pattern for crystalline Form 1 of Compound I is displayed in FIG. 17. Characteristic XRPD peaks include: 5.2±0.2° 2-Theta, 9.0±0.2° 2-Theta, 14.4±0.2° 2-Theta, and 17.7±0.2° 2-Theta.

Characterization of Crystalline Form 2 of Compound I

Figure 18:
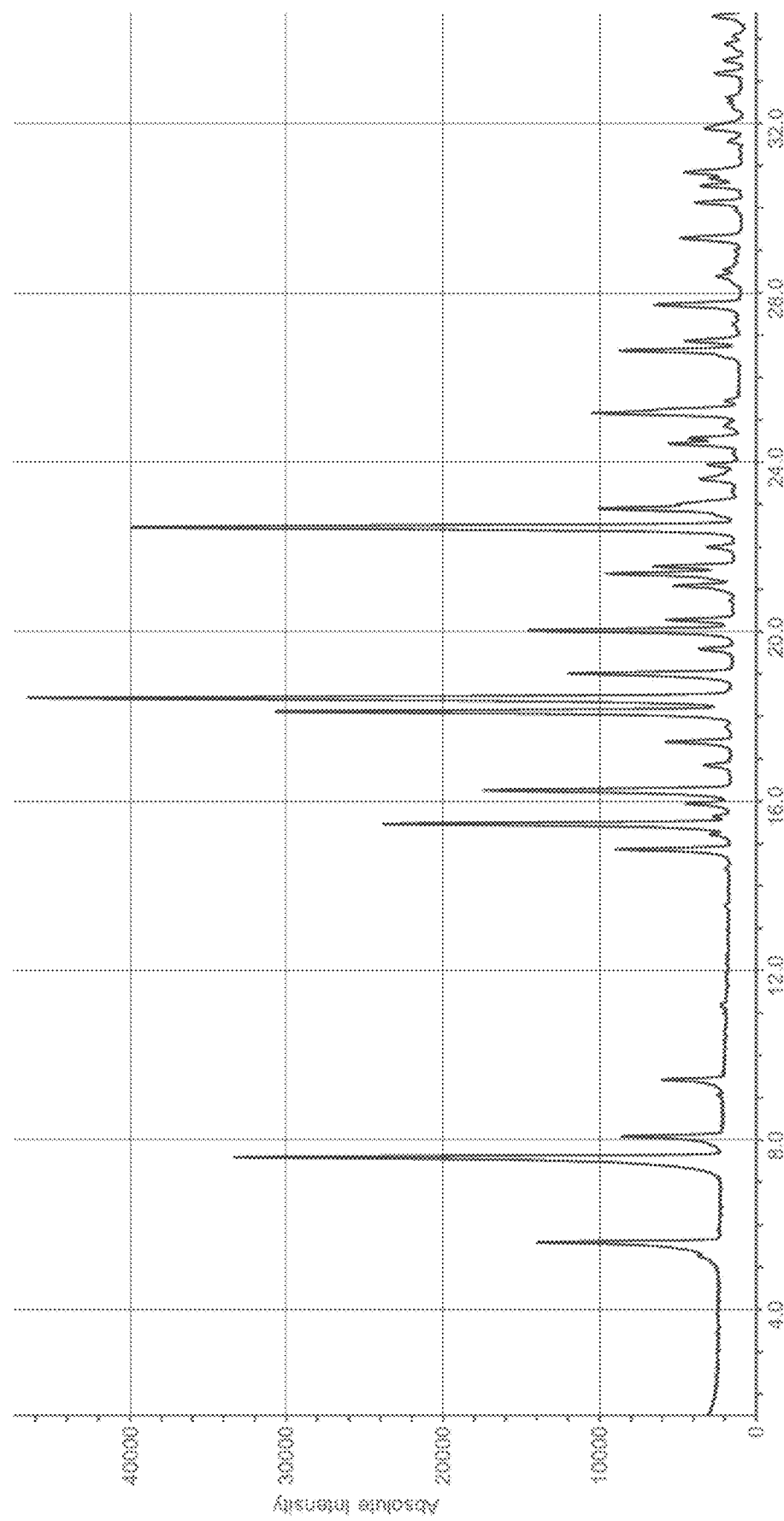
FIG. 18 shows the XRPD pattern of Form 2 obtained with the Stoe Stadi P, G.52.SYS.S072 diffractometer.
Figure 19:
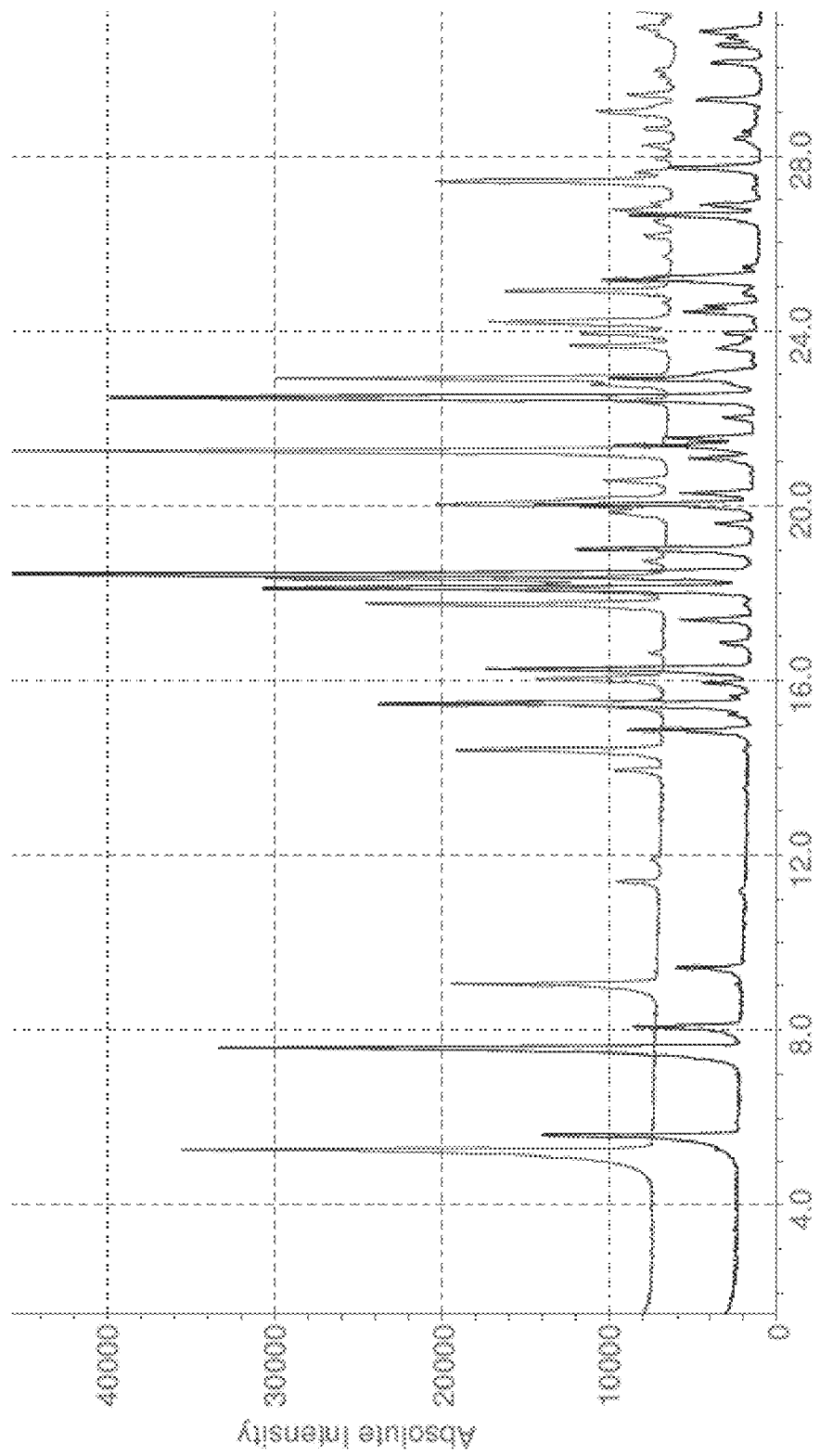
FIG. 19 shows an overlay of the XRPD patterns of Form 1 (top XRPD) Form 2 (bottom XRPD) obtained with the Stoe Stadi P, G.52.SYS.S072 diffractometer.

The X-Ray powder diffraction pattern for crystalline Form 2 of Compound I is displayed in FIG. 18. Characteristic XRPD peaks include: 5.5±0.2° 2-Theta, 7.5±0.2° 2-Theta, 8.0±0.2° 2-Theta, 9.4±0.2° 2-Theta, 14.8±0.2° 2-Theta, and 16.2±0.2° 2-Theta.

Figure 21:
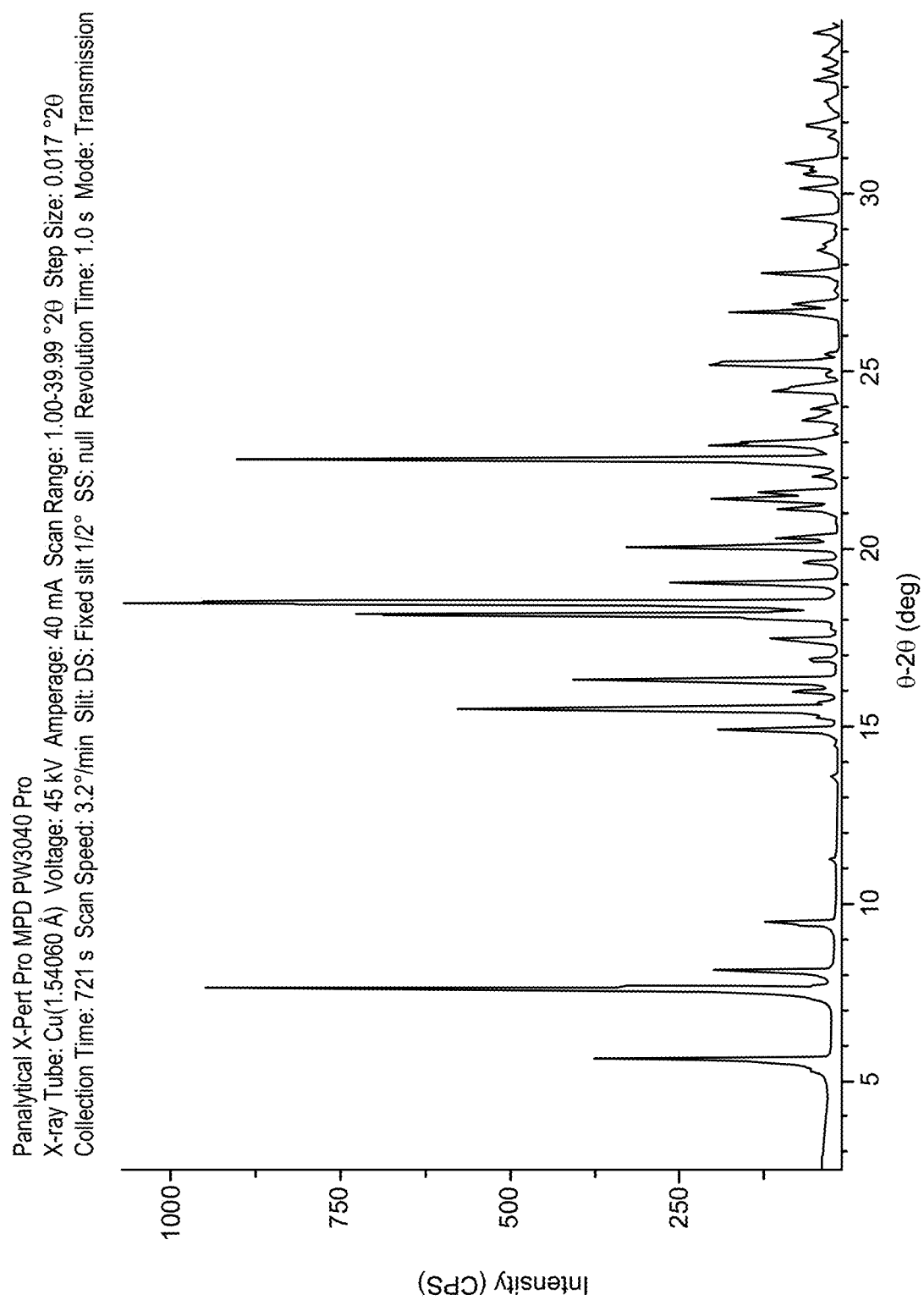
FIG. 21 shows the XRPD pattern of Form 2 obtained with the PANalytical X'Pert PRO MPD diffractometer.

An overlay of the XRPD of Form 1 (top spectra) and Form 2 (bottom spectra) is displayed in FIG. 21.

PANalytical X'Pert PRO MPD diffractometer

X-Ray Powder Diffractometry (XRPD, transmission mode): XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. A specimen of the sample was sandwiched between 3-μm-thick films and analyzed in transmission geometry. Prior to the analysis, a silicon specimen (NIST SRM 640f) was analyzed to verify the observed position of the Si 111 peak is consistent with the NIST-certified position. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 5.5.

X-ray Powder Diffraction Peak Identification Process: Rounding algorithms were used to round each peak to the nearest 0.10 or 0.01° 2Θ, depending upon the instrument used to collect the data and/or the inherent peak resolution. The location of the peaks along the x-axis (° 2-Theta) in both the figures and the tables were determined using TRIADS® v2.1.1 software and rounded to one or two significant figures after the decimal point based upon the above criteria. Peak position variabilities are given to within ±0.2° 2-Theta based upon recommendations outlined in the USP discussion of variability in x-ray powder diffraction (USP-NF 2021, Issue 2, <941>, *Characterization of Crystalline and Partially Crystalline Solids by X-Ray Powder Diffraction (XRPD)*, 1_GUID-14EBB55E-0D24-45A1-A84F-FE4DCAAEE3E8_1_en-US, official prior to 2013). In some embodiments, measurements on independently prepared samples on different instruments may lead to variability which is greater than ±0.2° 2-Theta. For d-space listings, the wavelength used to calculate d-spacings was 1.5405929 Å, the Cu-Kα$_1$ wavelength (Phys. Rev. A56(6) 4554-4568 (1997)).

Characterization of Crystalline Form 1 of Compound I

Figure 20:
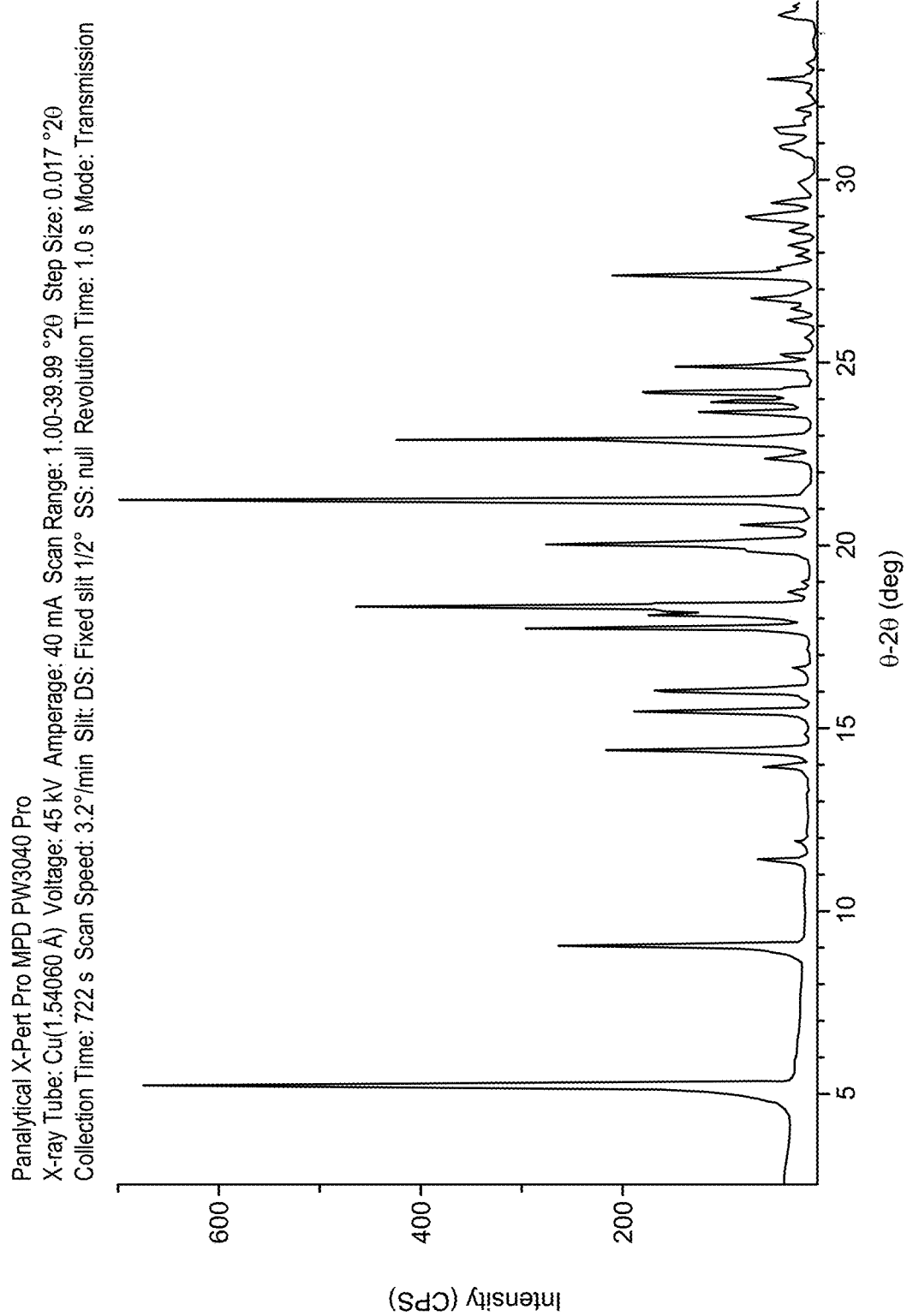
FIG. 20 shows the XRPD pattern of Form 1 obtained with the PANalytical X'Pert PRO MPD diffractometer.

The X-Ray powder diffraction pattern for crystalline Form 1 of Compound I is displayed in FIG. 20. Characteristic XRPD peaks include: 5.2±0.2° 2-Theta, 9.0±0.2° 2-Theta, 14.4±0.2° 2-Theta, and 17.7±0.2° 2-Theta.

Characterization of Crystalline Form 2 of Compound I

The X-Ray powder diffraction pattern for crystalline Form 2 of Compound I is displayed in FIG. 21. Characteristic XRPD peaks include: 5.5±0.2° 2-Theta, 7.5±0.2° 2-Theta, 8.0±0.2° 2-Theta, 9.4±0.2° 2-Theta, 14.8±0.2° 2-Theta, and 16.2±0.2° 2-Theta.

XRPD Limit Test Method with PANalytical X'Pert PRO MPD Diffractometer

Figure 22:
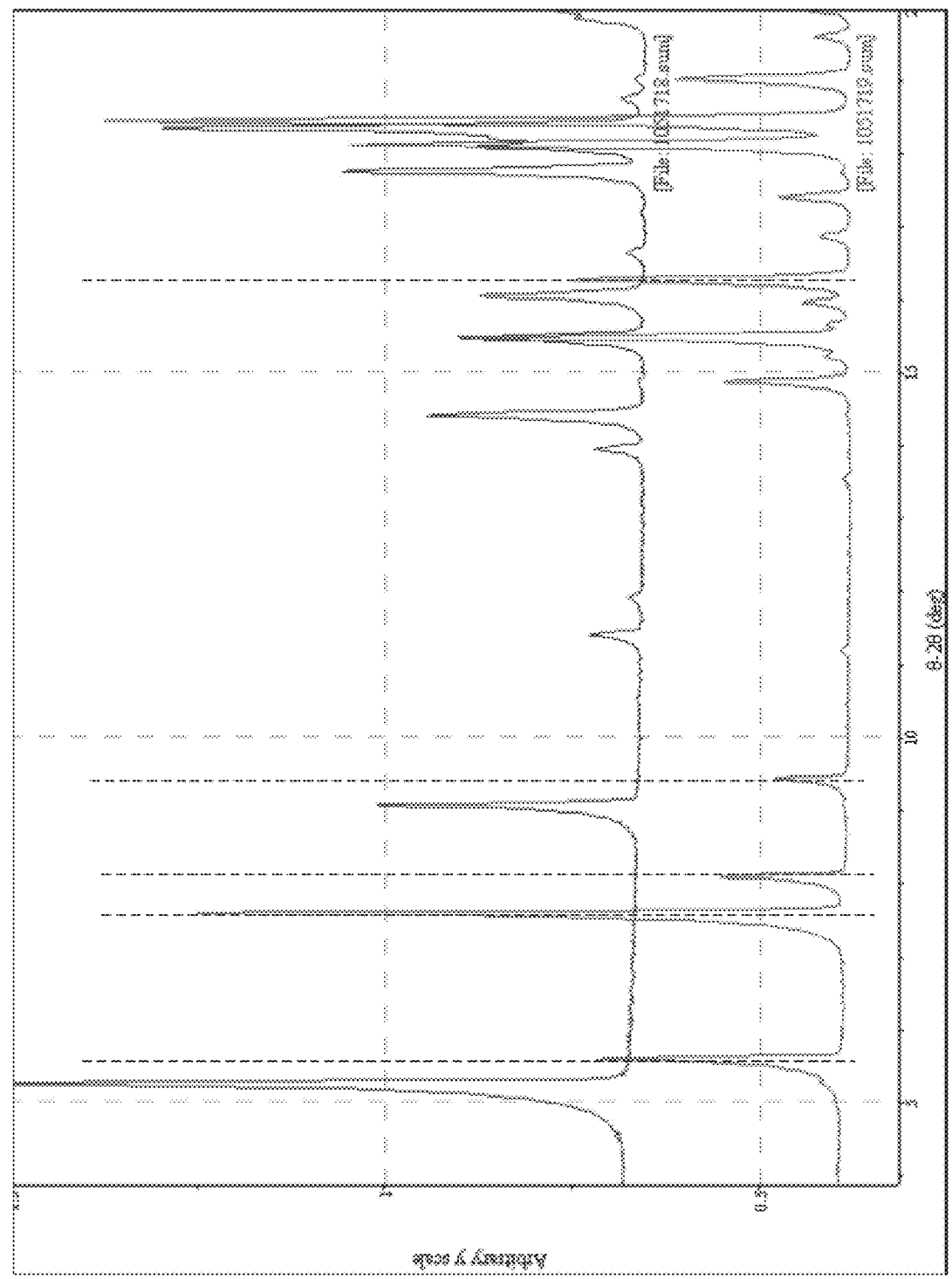
FIG. 22 shows a comparison of XRPD patterns of forms 1 (top XRPD) and 2 (bottom XRPD), highlighting the Form 2 peaks used for the quantification of Form 2 in Form 1.

A non-limiting method development of an XRPD limit test for determining Form 2 in Form 1 drug substance is described. Specificity, the ability to unequivocally assess the analyte in the presence of components that may be expected to be present, was assessed by comparing XRPD patterns of forms 1 and 2. Specificity of Form 2 is good in the Form 1 drug substance as several peaks highlighted in FIG. 22 can be used for the quantification of Form 2 (bottom spectra) in Form 1 (top spectra).

Calibration Models Generation: Calibration standards containing 0-10% Form 2 in Form 1 were prepared by geometrically mixing components without any extra sample handling.

| Form 2 | Form 1 | Form 2 | Form 1 | |
|---|---|---|---|---|
| mg | | % | | XRPD |
| 0.0000 | 100.0240 | 0.00 | 100.00 | 1054814 |
| 1.0260 | 98.9810 | 1.03 | 98.97 | 1054212 |
| 1.9830 | 98.0325 | 1.98 | 98.02 | 1054213 |
| 2.9730 | 96.9775 | 2.97 | 97.03 | 1054214 |
| 5.0255 | 94.9725 | 5.03 | 94.97 | 1054215 |
| 6.0170 | 93.9960 | 6.02 | 93.98 | 1054216 |
| 7.9800 | 92.0045 | 7.98 | 92.02 | 1054811 |
| 9.0410 | 90.9795 | 9.04 | 90.96 | 1054812 |
| 9.9990 | 90.0040 | 10.00 | 90.00 | 1054813 |

Figure 23:
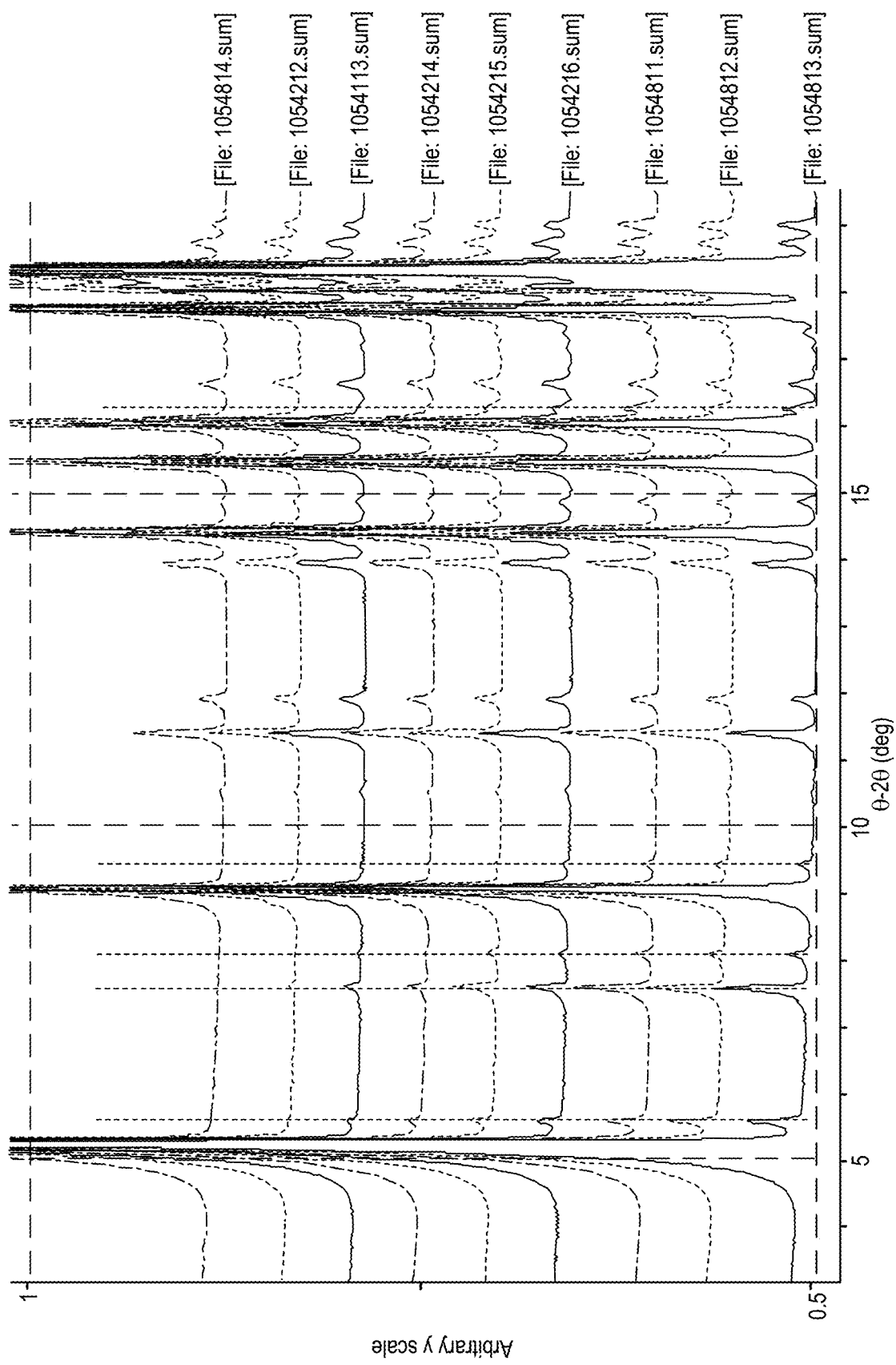
FIG. 23 shows XRPD overlays of the calibration standards used in the development of an XRPD limit test for determining Form 2 in Form 1 drug substance.

XRPD overlays of the calibration standards are shown in FIG. 23. Peaks unique to Form 2 were highlighted (with dotted lines) and showed good linearity based on visual assessment.

A spreadsheet was developed to calculate the areas of peaks approximately at 5.6°, 7.6°, and 8.10° which are normalized to the total peak area in the range of 4.0-25.5°.

Figure 24:
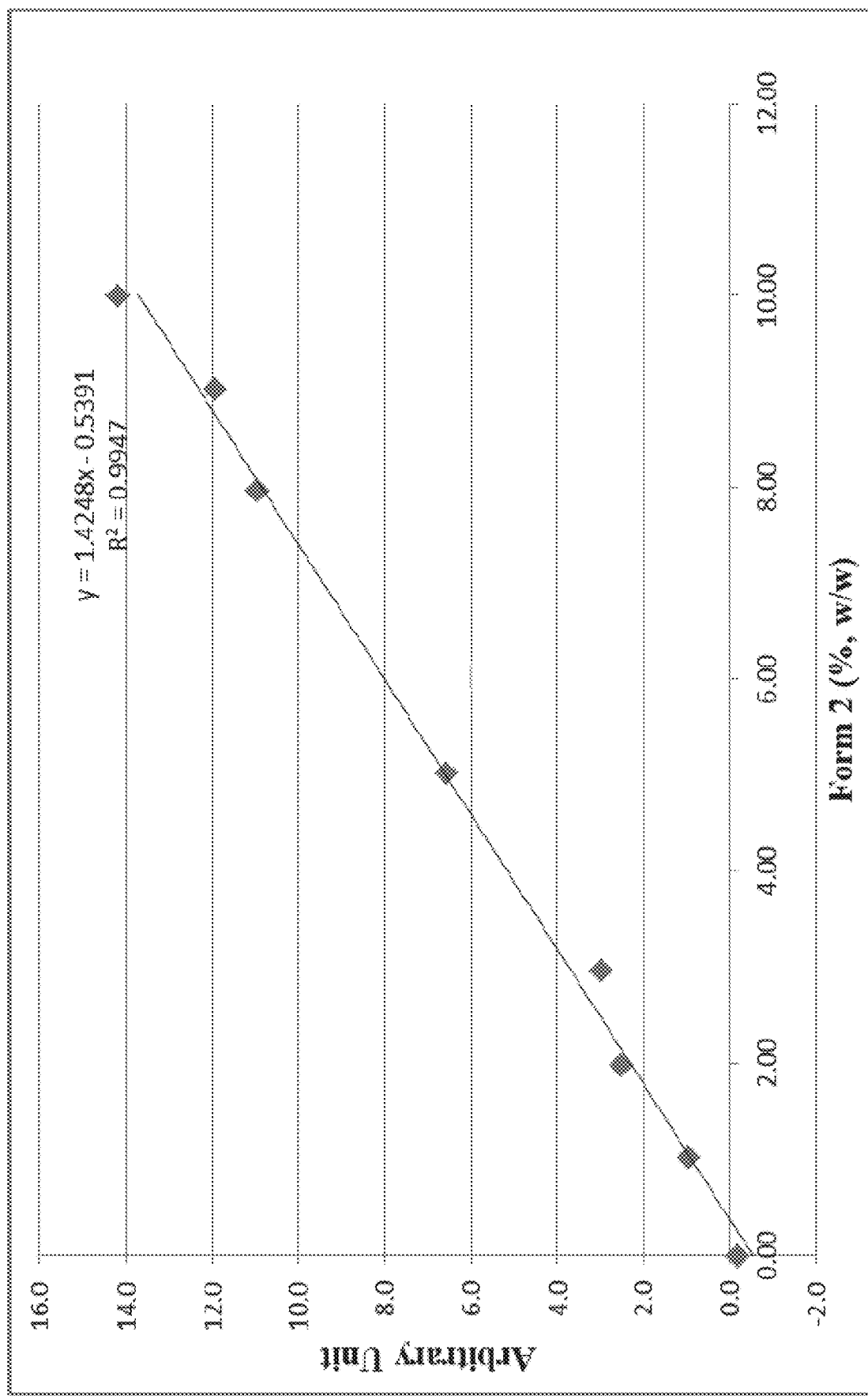
FIG. 24 shows the calibration curve used in the development of an XRPD limit test for determining Form 2 in Form 1 drug substance.

The calibration curve is shown in FIG. 24. Regression statistics along with the limit of detection (LOD) and limit of quantification (LOQ) are summarized below.

| Regression Statistics | |
|---|---|
| Multiple R | 0.9974 |
| R Square | 0.9947 |
| Adjusted R Square | 0.9938 |
| Standard Error | 0.4316 |
| Observations | 8 |

| ANOVA | | | | | |
|---|---|---|---|---|---|
| | df | SS | MS | F | Significance F |
| Regression | 1 | 210.54 | 210.54 | 1130.43 | 4.60825E-08 |
| Residual | 6 | 1.12 | 0.19 | | |
| Total | 7 | 211.66 | | | |

| | Coefficients | Standard Error | t Stat | P-value | Lower 95% | Upper 95% |
|---|---|---|---|---|---|---|
| Intercept | -0.54 | 0.25 | -2.13 | 0.08 | -1.16 | 0.08 |
| X Variable 1 | 1.42 | 0.04 | 33.62 | 4.6082E-08 | 1.32 | 1.53 |

LOD and LOQ were calculated using the following equations:

$$LOD=(3.3\times\sigma)/S$$

$$LOQ=(10\times\sigma)/S$$

where σ is the standard error of linear regression and S is the slope of the calibration curve. The LOD and LOQ were calculated to be 1.0% and 2.8% (w/total), respectively.

Example 8: Differential Scanning Calorimetry (DSC)

9.1 METTLER DSC822e

DSC measurements are performed with a METTLER DSC822e (module DSC822e/700/109/414935/0025). 40 μl Al-crucibles with sealed lid and pinhole are used. All measurements are carried out in a nitrogen gas flow of 50 mL/min and typical heating rate of 10° C./min. The measured data is evaluated via the software STARe V8.10.

9.2 Perkin Elmer Diamond DSC

DSC scans were obtained using a Perkin Elmer Diamond DSC. The samples were encapsulated in aluminum pans that were pierced to allow for residual solvent to be released. Scans were obtained at 10° C./min from 25-240° C. The system was calibrated with indium (MP 156.6° C.) and tin (MP 231.9° C.) prior to use.

Characterization of Solid State Forms of Compound I

The DSC thermogram for crystalline Form 1 of Compound I is displayed in FIG. 2.

The DSC thermogram for crystalline Form 2 of Compound I is displayed in FIG. 6.

Figure 9:
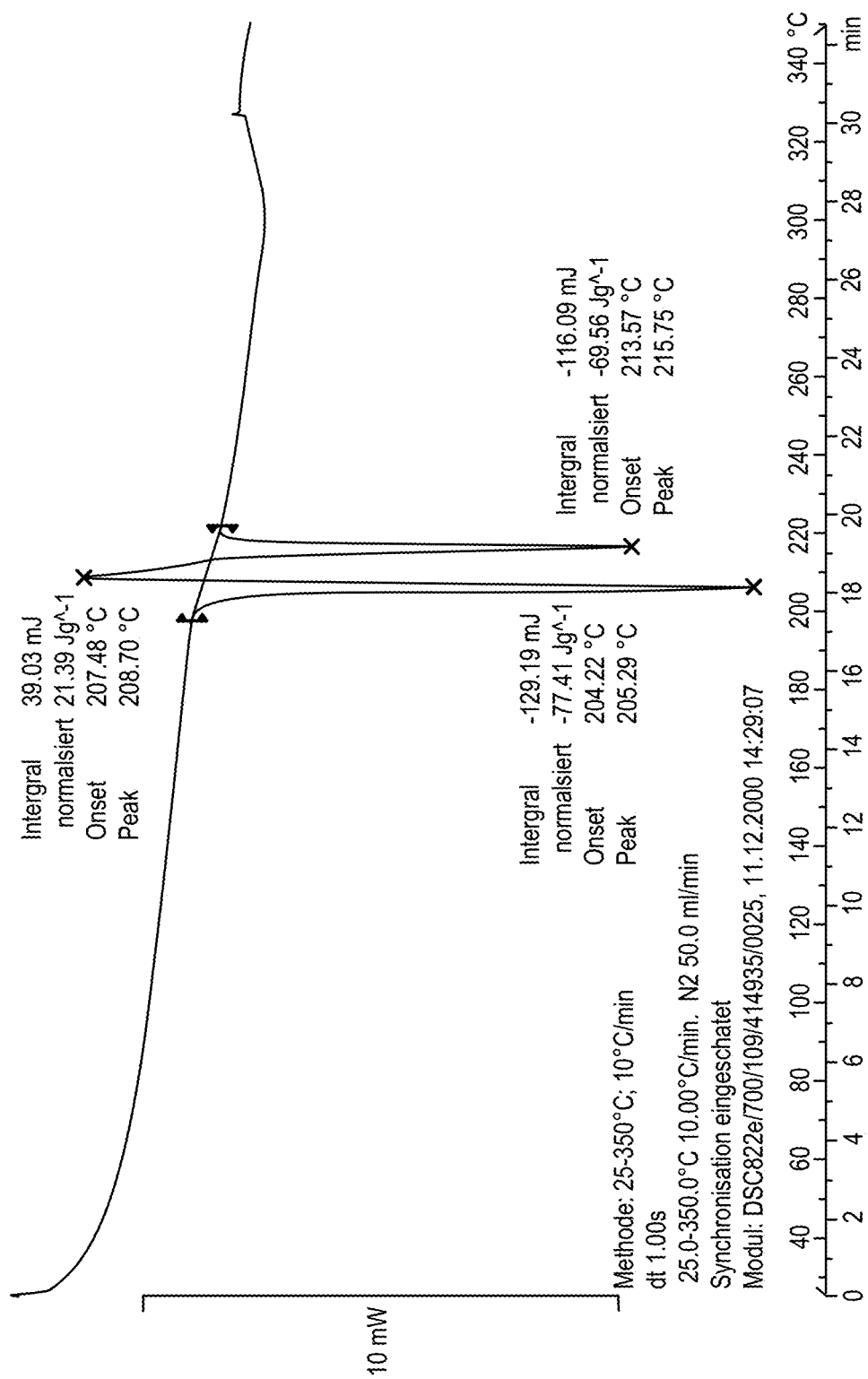
FIG. 9 shows the Differential Scanning Calorimetry (DSC) thermogram of Form 3.

The DSC thermogram for crystalline Form 3 of Compound I is displayed in FIG. 9.

Figure 12:
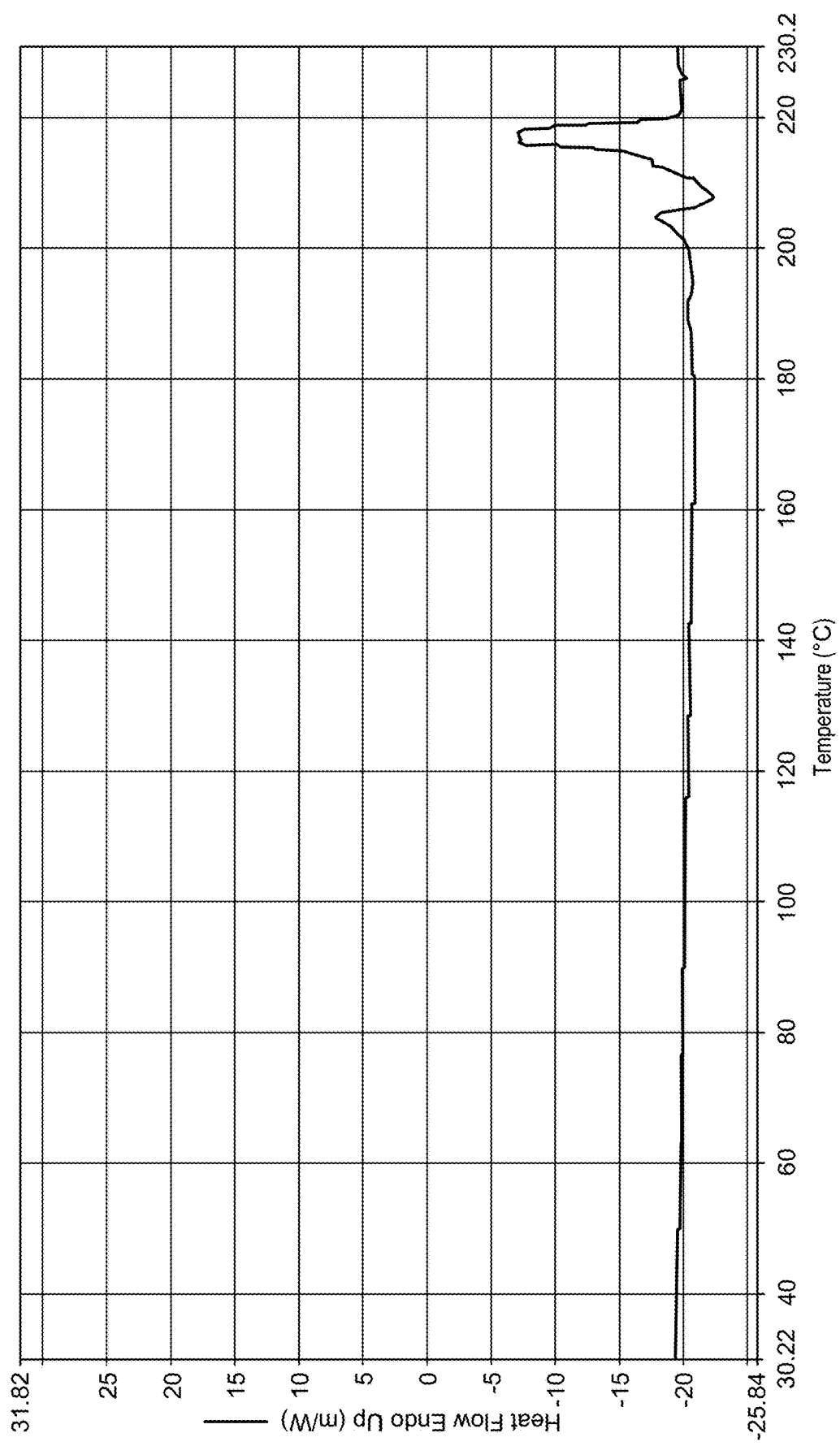
FIG. 12 shows the Differential Scanning Calorimetry (DSC) thermogram of Form 4.

The DSC thermogram for crystalline Form 4 of Compound I is displayed in FIG. 12.

Differential Scanning Calorimetry (DSC) thermogram thermal events for the solid state forms are as described in the following table:

| Solid State Form | DSC Thermal Events |
| --- | --- |
| Form 1 | three endothermic events having: an onset at about 198.5° C. and a peak at about 200.4° C.; an onset at about 204.8° C. and a peak at about 205.8° C.; and an onset at about 213.9° C. and a peak at about 216.3° C. |
| Form 2 | endothermic event having an onset at about 215.3° C. and a peak at about 216.4° C. |
| Form 3 | two endothermic events having: an onset at about 204.2° C. and a peak at about 205.3° C.; and an onset at about 213.6° C. and a peak at about 215.8° C. |

Example 9: Thermogravimetric Analysis (TGA)

Method 10.1: METTLER TGA851e

The thermogravimetric analyses are performed with a METTLER TGA851e (module TGA/SDTA851e/SF 1100/042). 100 μl Al-crucibles with sealed lid and hole are used and the measurements are performed in a nitrogen gas flow of 50 mL/min. The measured data is evaluated via the software STARe V8.10.

Method 10.2: Perkin Elmer Pyris System

TGA was obtained on either a Perkin Elmer Pyris System. The samples were run from 25-200° C. at 10° C./min. Accuracy of the system was verified using barium chloride dihydrate.

Characterization of Solid State Forms of Compound I

The TGA pattern for crystalline Form 1 of Compound I is displayed in FIG. 3.

Thermogravimetric Analysis (TGA) patterns for the solid state forms are as described in the following table:

| Solid State Form | TGA Pattern |
| --- | --- |
| Form 1 | method 10.1: 15.4% w/w loss from about 287.9° C. to about 298.9° C.; method 10.2: TGA pattern (up to 200° C.) showed less than 1% weight loss |
| Form 2 | TGA pattern (up to 200° C.) showed less than 1% weight loss |
| Form 3 | TGA pattern (up to 200° C.) showed less than 1% weight loss |
| Form 4 | TGA pattern (up to 200° C.) showed less than 1% weight loss |

Example 10: Dynamic Vapor Sorption (DVS)

Moisture sorption/desorption isotherms are recorded on a DVS-1 from SURFACE MEASUREMENT SYSTEMS. Two cycles are run at 25° C., in which the Relative Humidity (RH) is stepped from 0 to 95% and back to 0%. The data is evaluated with the software DVSWin V. 2.15.

Reversible water uptake for Form 1 of Compound I as determined by DVS is less than 1% (~-0.1% w/w between 0 and 95% RH).

Example 11: Fourier Transform Infrared (FTIR) Spectroscopy

Nicolet *Magna* 750 system was used to collect FTIR of the different solid state forms of Compound I. Samples were prepared at 1% concentration in KBr and compressed at 10,000 lbs.

Figure 13:
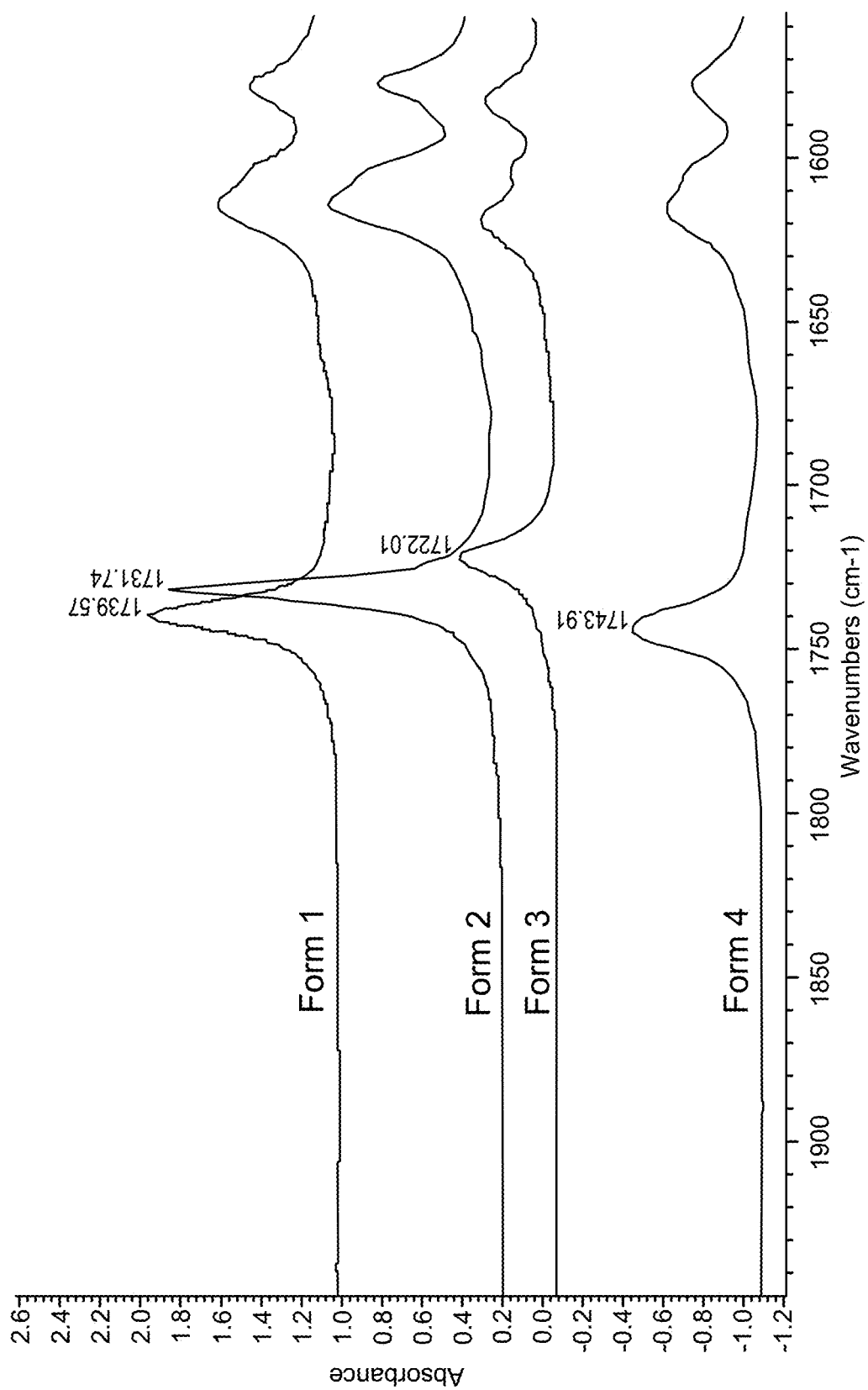
FIG. 13 shows the Fourier Transform IR Spectroscopy (FTIR) pattern overlay of Forms 1, 2, 3, and 4.

The partial Fourier Transform Infrared (FTIR) pattern overlay for crystalline Forms 1, 2, 3, and 4 of Compound I is displayed in FIG. 13. The FTIR spectrum for Crystalline Form 1 has a peak at about 1739.6 cm$^{-1}$. The FTIR spectrum for Crystalline Form 2 has a peak at about 1731.7 cm$^{-1}$. The FTIR spectrum for Crystalline Form 3 has a peak at about 1722.0 cm$^{-1}$. The FTIR spectrum for Crystalline Form 4 has a peak at about 1743.9 cm$^{-1}$.

Example 12: Fourier Transform Raman Spectroscopy

Raman spectra were acquired on a Raman module interfaced to a Nicolet 6700 IR spectrophotometer (Thermo Nicolet) equipped with an indium gallium arsenide (InGaAs) detector. Wavelength verification was performed using sulfur and cyclohexane. Each sample was prepared for analysis by placing the sample into a 13 mm diameter stainless steel cup and leveling the material. A Thermo Nicolet Step-and-Repeat accessory was used to spin the cup during data acquisition. Three spectra were collected for each sample from outer to inner rings of the sample cup. Approximately 0.5 W of Nd:YVO4 laser power (1064 nm excitation wavelength) was used to irradiate the sample. Each spectrum consists of 512 co-added scans with a spectral resolution of 2 cm$^{-1}$. The three spectra for each sample were averaged using Omnic v7.2 (ThermoElectron).

Raman peak position variabilities are given to within ±2 cm$^{-1}$, based on the observed sharpness of the peaks picked and acquisition of data using a 1 cm$^{-1}$ data point spacing (2 cm-1 resolution). The peak picking was performed using OMNIC software, version 7.2, Thermo Electron Corporation. Observed Peaks include all Raman peaks for a given form, with the exclusion of very weak intensity peaks and broad peaks with poorly defined maxima.

Figure 25:
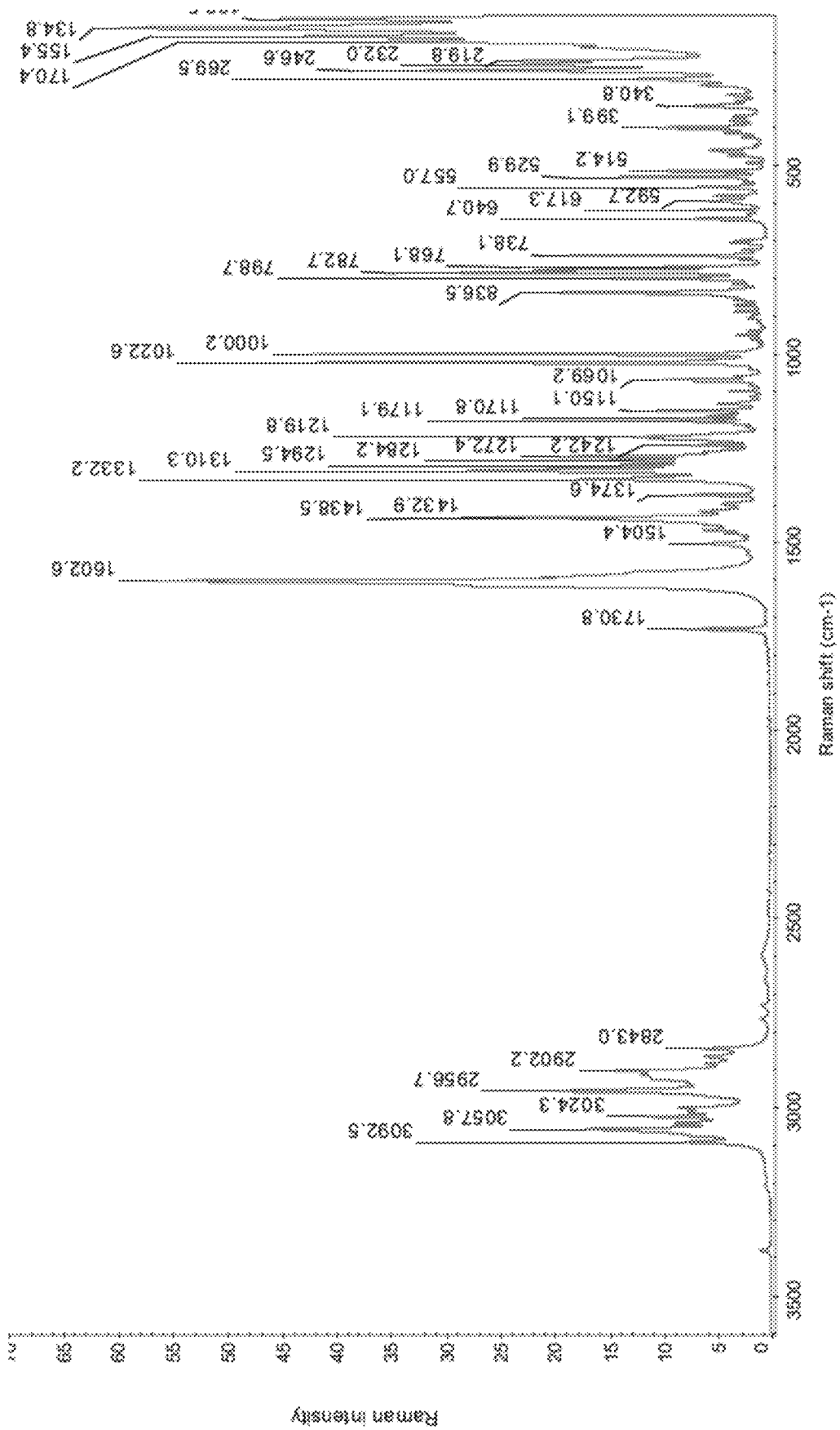
FIG. 25 shows the Raman spectrum for Form 1.
Figure 26:
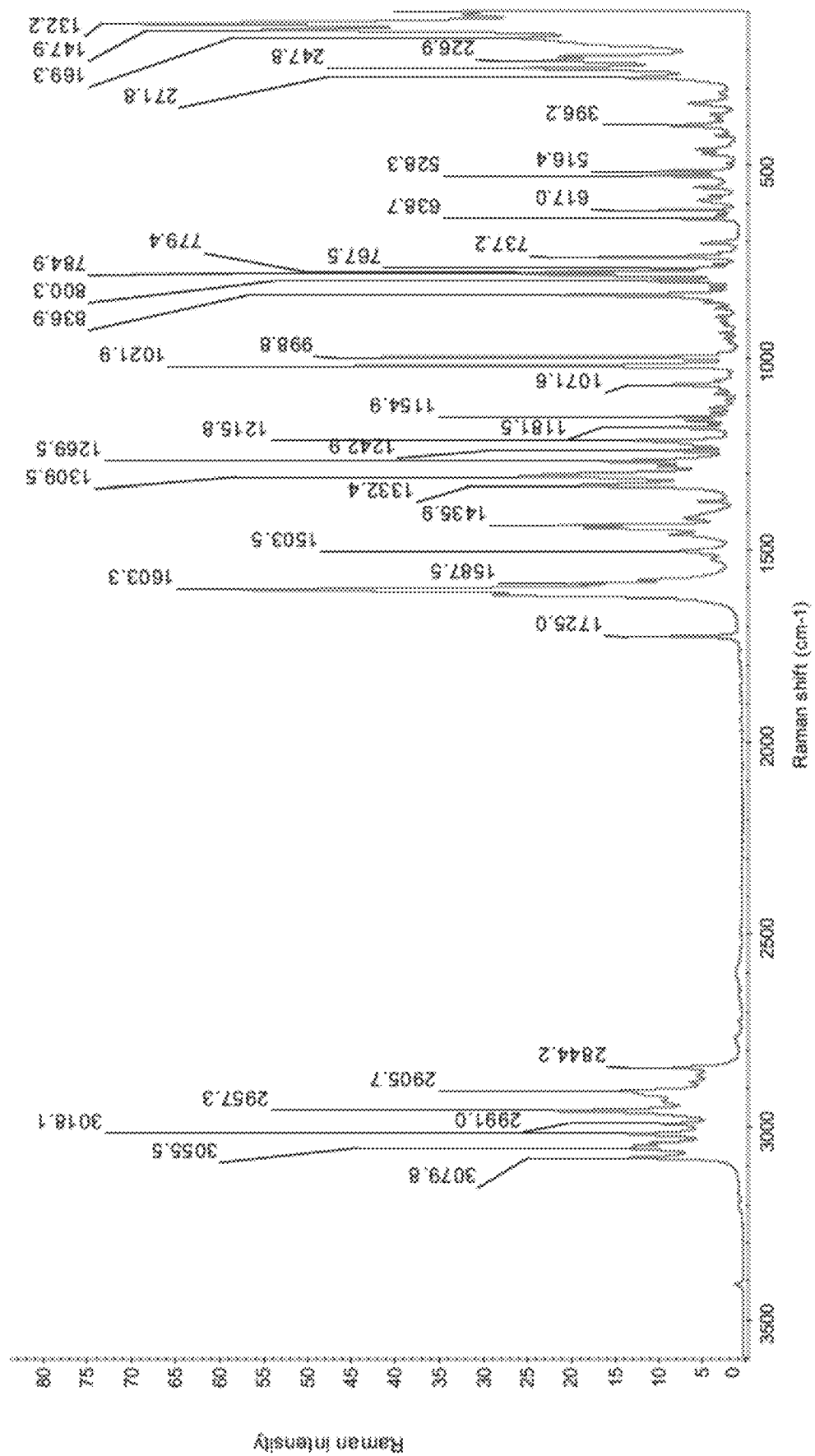
FIG. 26 shows the Raman spectrum for Form 2.

The Raman spectrum for Form 1 is displayed in FIG. 25.
The Raman spectrum for Form 2 is displayed in FIG. 26.

Example 13: Solid State Nuclear Magnetic Resonance (ssNMR) Spectroscopy

All spectra were acquired using a Bruker DRX500 spectrometer, equipped with a 11.7 Tesla magnet and a 4 mm diameter solid-state probe. The following parameters were employed:

| | |
|---|---|
| Observation nucleus | $^{13}C$ |
| Observation frequency | 125.77 MHz |
| Complex data points | 2716 zero-filled to 4096 |
| Spectral width | 34.0 kHz |
| Acquisition time | 40 ms |
| Number of dummy transients | 2 |
| Number of transients | 2048 |
| Relaxation delay | 11.0 s for Form 1 |
| | 20.0 s for Form 2 |
| | 12.0 s for Form 3 |
| | 11.0 s for Amorphous |
| Contact time | 5.0 ms for Form 1 |
| | 3.0 ms for Form 2 |
| | 2.0 ms for Form 3 |
| | 3.0 ms for Amorphous |
| $\pi/2$ proton pulse length | 2.9 µs |
| $^1H$ decoupling | TPPM-15 |
| Sample rotation rate | 14.0 kHz |
| Temperature | Ambient |

All spectra are referenced indirectly with respect to tetramethylsilane using the high frequency signal of adamantane. All samples were packed into 4 mm OD rotors constructed of zirconia, fitted with a Kel-F drive cap. A Gaussian convolution was applied to the free induction decay prior to Fourier transformation; GB=0.035 and LB=−10.0 Hz.

Characterization of Crystalline Form 1 of Compound I

The ssNMR spectrum for crystalline Form 1 of Compound I is displayed in FIG. 4. Resonances that are characteristic of Form 1 are listed below:

δc/ppm: 23.35, 36.40, 44.12, 45.70, 54.41, 65.40, 71.58, 110.97, 114.45, 121.00, 124.43, 126.78, 127.42, 131.27, 136.47, 138.94, 142.61, 148.68, 152.19, 172.07, 174.59

Characterization of Crystalline Form 2 of Compound I

Figure 7:
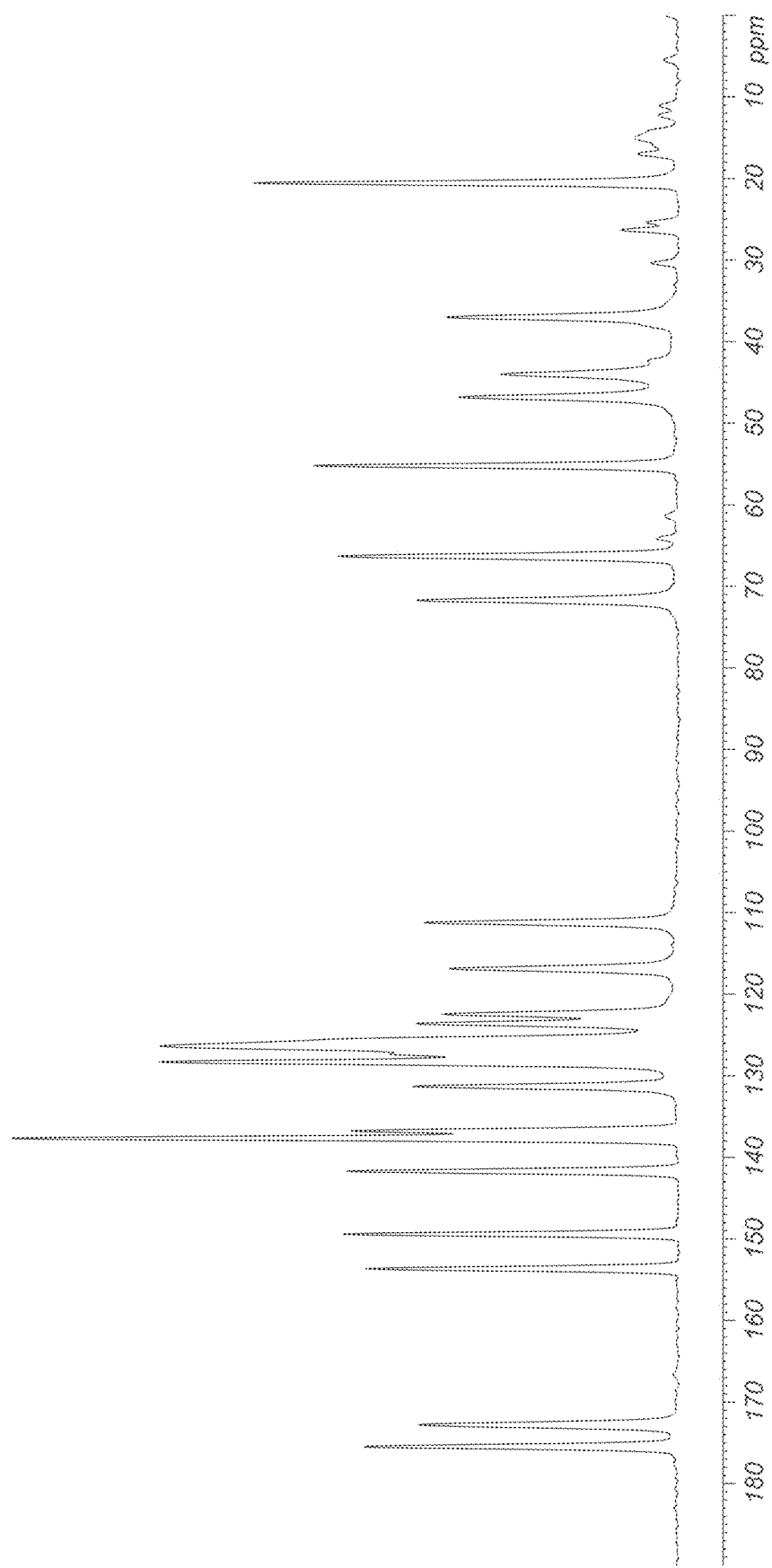
FIG. 7 shows the Solid State $^{13}$Carbon NMR Spectrum of Form 2.

The ssNMR spectrum for crystalline Form 2 of Compound I is displayed in FIG. 7. Resonances that are characteristic of Form 2 are listed below:

δc/ppm: 20.59, 37.04, 44.03, 46.84, 55.25, 66.34, 71.74, 111.25, 116.90, 122.48, 123.63, 126.39, 128.34, 131.33, 136.78, 137.69, 141.73, 149.44, 153.68, 172.82, 175.49

Figure 10:
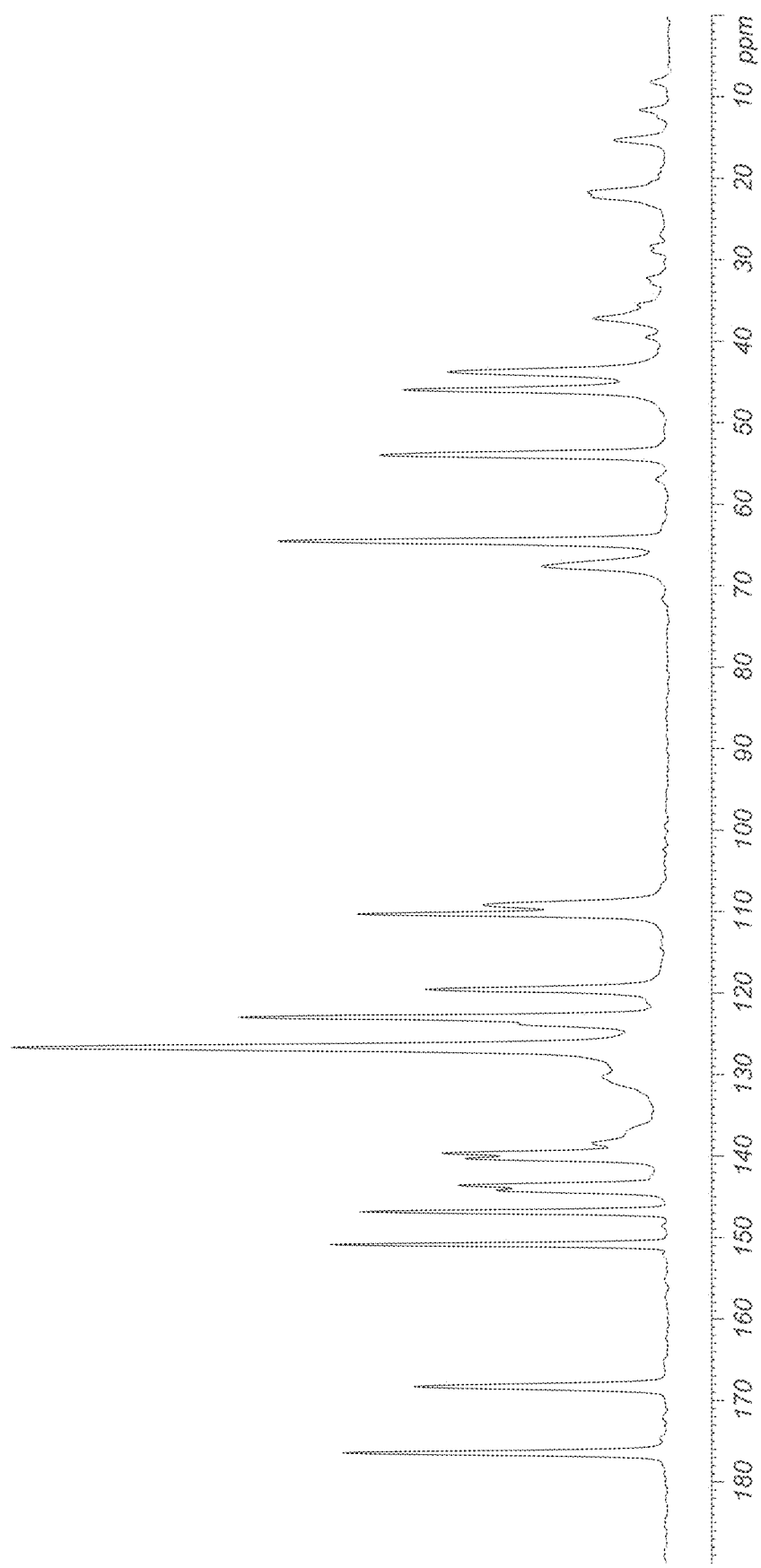
FIG. 10 shows the Solid State $^{13}$Carbon NMR Spectrum of Form 3.

Characterization of Crystalline Form 3 of Compound I
The ssNMR spectrum for crystalline Form 3 of Compound I is displayed in FIG. 10. Resonances that are characteristic of Form 3 are listed below:

δc/ppm: 21.72#, 22.23#, 43.81, 46.00, 54.01, 64.56, 67.67, 109.22, 110.33, 119.58, 122.99, 126.71, 130.28#, 138.46#, 139.68, 140.34, 143.63, 144.25, 146.87, 150.90, 168.32, 176.47 # broadened or split signals whose shape or chemical shift may vary.

Figure 14:
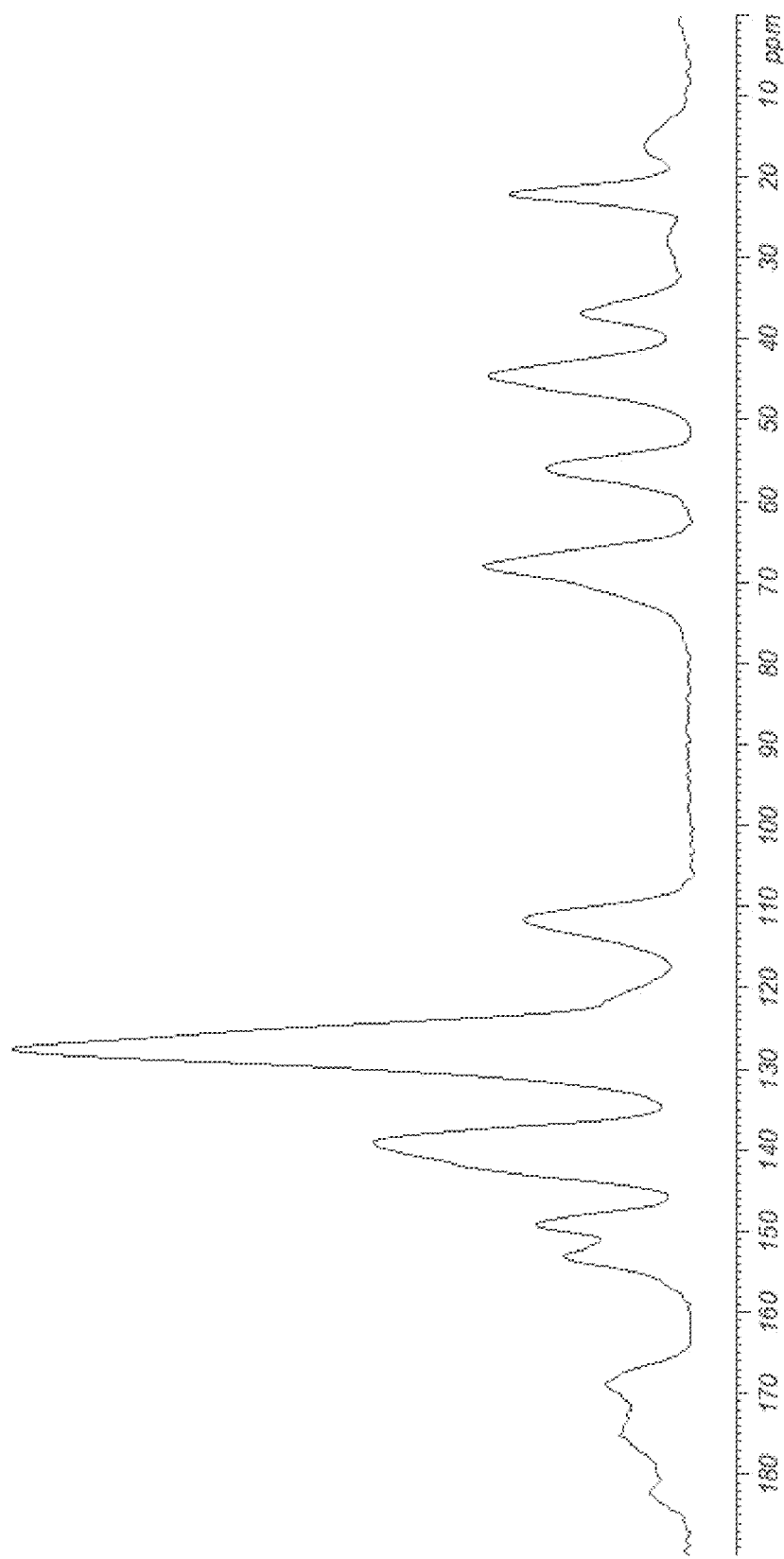
FIG. 14 shows the Solid State $^{13}$Carbon NMR Spectrum of Amorphous Form.

Characterization of Amorphous Form of Compound I
The ssNMR spectrum for amorphous form of Compound I is displayed in FIG. 14.

Example 14: Stability of Solid State Forms

The physical stability of Forms 1, 2, and 3 was investigated at 80° C./75% RH in order to determine if interconversion was observed. The samples were examined by FTIR after stressing 1 week in open glass vials.

No changes in the FTIR spectrums were observed for any of the forms, suggesting that these forms are relatively stable in the solid state.

Example 15: Solubility Studies

The solubility of the different polymorphs was determined at pH 7.4 in phosphate buffer at 25° C. Samples were analyzed as a function of time for each form to determine the equilibrium values. The residual solids from each sample were analyzed to verify that the form was unchanged during the experiment. The concentration (mg/mL) versus time data is listed below for each form:

| | 1 hr | 2 hr | 3 hr | 24 hr |
|---|---|---|---|---|
| Form 1 | 0.042 | 0.041 | 0.042 | 0.042 |
| Form 2 | 0.034 | 0.039 | 0.043 | 0.057* |
| Form 3 | 0.083 | 0.093 | 0.095 | 0.097 |
| Form 4 | 0.079 | 0.089 | 0.105 | 0.102 |

*additional time point confirmed equilibrium

The equilibrium solubility values at 24 hours show Forms 3 and 4 to be more than double the solubility for Form 1. The 24 hour result for Form 2 was more than 30% greater than Form 1.

It should be noted that analysis of the residual solids showed no polymorphic conversion during the course of the experiments. The data for Forms 3 and 4 are equivalent within experimental error.

Example 16: Single Crystal X-Ray Diffraction (SCXRD) of Crystalline Form 1 of Compound I Crystallization of Compound I from propyl acetate yielded a crystal—0.5*0.04*0.02 mm³ in size—which was sealed in a Lindemann-glass capillary. X-ray diffraction data were collected on a Bruker/AXS three circle diffractometer, equipped with a SMART APEX area-detector, a low temperature device (model LT 2) and a molybdenum-$K_\alpha$ rotating anode generator, operated at 50 kV/120 mA and adjusted to a fine-focus of 0.5×5 mm². Data frames were collected using the program package SMART V 5.628 (Bruker AXS, 2001), applying ω-scans with step widths of 0.3° and an exposure time of 60 seconds. Data processing with the program SAINT+Release 6.45 (Bruker AXS, 2003) yielded 6452 reflections ($\vartheta_{min}$=2.04, $\vartheta_{max}$=28.06; −8<h<8, −7<k<13, −22<l<22) of which 4753 reflections were unique ($R_{int}$=0.0829, $R_\sigma$=0.2353). Refinement of the cell parameters was performed using 720 reflections. The phase problem was solved with direct methods by the XS module of SHELXTL 6.14 (Bruker AXS, 2000).

The structure was refined by least-squares methods (minimization of $(F_o^2-F_c^2)^2$) using the XL module of SHELXTL 6.14 (Bruker AXS, 2000). The positions of all H atoms were experimentally determined from a difference Fourier synthesis map, $S_{goodness\ of\ fit}$=0.780, $R_{all\ data}$=0.2189

($R_{obs.\ data}$=0.0536 for 1479 reflections with $|F_{obs}|>4\sigma$, $wR2_{all\ data}$=0.1080, $wR2_{obs.\ data}$=0.0759). The largest unassigned peaks in the difference map correspond to −0.193 versus+0.162 electrons per Å$^3$. The average estimated standard deviation (e.s.d.) of a C—C bond is 0.005 Å, that of an O—C bond 0.004 Å, that of an N—C bond 0.004 Å and that of a C—H bond 0.03 Å. The average e.s.d. of C—C—C bond angles is 0.4 and that of C—C—C—C torsion angles 0.5°.

The crystal structure of Crystalline Form 1 of Compound I was determined at 293 K and a summary of the structural data can be found in Table 1 and Table 2.

TABLE 1

| Crystal Data of Compound I (Form 1) at 293 K | |
| --- | --- |
| Crystal System | triclinic |
| Space Group | P-1; Z = 2 |

TABLE 1-continued

| Crystal Data of Compound I (Form 1) at 293 K | |
| --- | --- |
| a (Å) | 6.521(6) |
| b (Å) | 10.548(9) |
| c (Å) | 17.453(15) |
| α (°) | 104.080(16) |
| β (°) | 92.430(16) |
| γ (°) | 101.081(17) |
| V (Å$^3$) | 1137.6(17) |
| Calculated Density (Mg/m$^3$) | 1.301 |
| Unique Reflections | 4753 |
| Model Quality | $R_{obs.\ data}$ = 5.36 % |

TABLE 2

Atomic coordinates and equivalent isotropic displacement parameters [Å] for Compound I (Form 1) at 293 K

| | x | Y | Z | U(eq)* |
| --- | --- | --- | --- | --- |
| O01 | 0.5030(4) | 0.4696(2) | −0.24147(13) | 0.0519(8) |
| O02 | 0.1244(4) | 0.3734(2) | −0.21202(13) | 0.0517(7) |
| O03 | 0.8430(4) | 0.7934(2) | 0.03104(13) | 0.0437(7) |
| O04 | 0.8283(4) | 1.0809(2) | 0.02552(15) | 0.0441(7) |
| O05 | 1.0255(4) | 1.1365(3) | 0.14238(14) | 0.0665(9) |
| N01 | 0.5633(5) | 0.8827(3) | 0.06678(19) | 0.0418(9) |
| C01 | 1.0831(7) | 0.5910(4) | −0.3552(2) | 0.0543(12) |
| C02 | 1.2317(7) | 0.6751(5) | 0.3842(3) | 0.0661(14) |
| C03 | 1.1721(8) | 0.7334(5) | −0.4423(3) | 0.0654(15) |
| C04 | 0.9651(7) | 0.7091(4) | −0.4737(2) | 0.0557(12) |
| C05 | 0.9012(14) | 0.7688(9) | −0.5392(4) | 0.092(2) |
| C06 | 0.8190(7) | 0.6242(4) | −0.4438(2) | 0.0516(11) |
| C07 | 0.8725(6) | 0.5657(4) | −0.3858(2) | 0.0435(10) |
| C08 | 0.7044(8) | 0.4798(5) | −0.3518(2) | 0.0552(13) |
| C09 | 0.6788(7) | 0.5492(4) | −0.2681(2) | 0.0478(12) |
| C10 | 0.4477(6) | 0.5258(4) | −0.1675(2) | 0.0403(10) |
| C11 | 0.2397(6) | 0.4736(3) | −0.1521(2) | 0.0438(10) |
| C12 | −0.0778(7) | 0.3071(5) | −0.1940(3) | 0.0548(12) |
| C13 | 0.1733(7) | 0.5270(4) | −0.0805(2) | 0.0531(12) |
| C14 | 0.3017(6) | 0.6301(4) | −0.0243(2) | 0.0515(12) |
| C15 | 0.5061(5) | 0.6793(3) | −0.0386(2) | 0.0379(10) |
| C16 | 0.5770(6) | 0.6257(4) | −0.1102(2) | 0.0400(10) |
| C17 | 0.6506(6) | 0.7874(4) | 0.0212(2) | 0.0388(10) |
| C18 | 0.6849(5) | 0.9914(3) | 0.1310(2) | 0.0361(9) |
| C19 | 0.7593(6) | 0.9353(5) | 0.1986(2) | 0.0432(11) |
| C20 | 0.5965(5) | 0.9512(3) | 0.2570(2) | 0.0402(10) |
| C21 | 0.5709(7) | 0.8992(5) | 0.3221(3) | 0.0529(12) |
| C22 | 0.4184(7) | 0.9324(5) | 0.3719(3) | 0.0613(13) |
| C23 | 0.2946(8) | 1.0159(5) | 0.3560(3) | 0.0607(14) |
| C24 | 0.3156(6) | 1.0695(4) | 0.2899(2) | 0.0468(11) |
| C25 | 0.4722(6) | 1.0356(3) | 0.2408(2) | 0.0378(10) |
| C26 | 0.5351(6) | 1.0837(4) | 0.1691(2) | 0.0405(10) |
| C27 | 0.8654(6) | 1.0758(4) | 0.1007(2) | 0.0429(10) |
| H1 | 0.448(4) | 0.886(3) | 0.0505(17) | 0.025(11) |
| H4 | 0.953(7) | 1.131(4) | 0.016(2) | 0.112(18) |
| H01 | 1.122(4) | 0.543(3) | −0.3064(17) | 0.050(10) |
| H02 | 1.390(6) | 0.700(3) | −0.357(2) | 0.089(14) |
| H03 | 1.276(5) | 0.791(3) | −0.4616(18) | 0.061(12) |
| H051 | 0.924(8) | 0.726(5) | −0.582(3) | 0.12(3) |
| H052 | 0.999(10) | 0.857(6) | −0.534(4) | 0.24(4) |
| H053 | 0.776(7) | 0.777(5) | −0.536(3) | 0.13(3) |
| H06 | 0.680(5) | 0.607(3) | −0.4665(17) | 0.041(11) |
| H081 | 0.745(5) | 0.392(3) | −0.3537(19) | 0.062(14) |
| H082 | 0.571(5) | 0.446(3) | −0.3879(18) | 0.064(12) |
| H091 | 0.647(5) | 0.645(3) | −0.2638(17) | 0.052(12) |
| H092 | 0.815(5) | 0.570(3) | −0.2255(19) | 0.073(12) |
| H121 | −0.175(6) | 0.376(4) | −0.183(2) | 0.086(15) |
| H122 | −0.130(5) | 0.245(3) | −0.244(2) | 0.079(14) |
| H123 | −0.054(6) | 0.267(4) | −0.136(3) | 0.131(18) |
| H13 | 0.035(5) | 0.500(3) | −0.073(2) | 0.076(14) |
| H14 | 0.256(4) | 0.664(3) | 0.0241(17) | 0.044(11) |

TABLE 2-continued

Atomic coordinates and equivalent isotropic displacement parameters [Å] for Compound I (Form 1) at 293 K

| | x | Y | Z | U(eq)* |
|---|---|---|---|---|
| H16 | 0.716(4) | 0.667(2) | −0.1171(14) | 0.025(9) |
| H191 | 0.750(4) | 0.844(3) | 0.1739(17) | 0.041(11) |
| H192 | 0.902(5) | 0.999(3) | 0.2276(15) | 0.043(9) |
| H21 | 0.651(5) | 0.842(3) | 0.3281(19) | 0.047(13) |
| H22 | 0.399(5) | 0.900(3) | 0.426(2) | 0.085(13) |
| H23 | 0.181(6) | 1.031(4) | 0.385(2) | 0.082(15) |
| H24 | 0.227(5) | 1.130(3) | 0.2714(17) | 0.047(11) |
| H261 | 0.611(5) | 1.188(3) | 0.1875(16) | 0.051(10) |
| H262 | 0.427(5) | 1.084(3) | 0.1328(17) | 0.051(12) |

*U(eq) is defined as one third of the trace of the orthogonalized Uij tensor.

Example 17: Single Crystal X-Ray Diffraction (SCXRD) of Crystalline Form 2 of Compound I Crystallization of Compound I from N-methyl-2-pyrrolidone/methanol yielded a crystal—0.6*0.2*0.2 mm³ in size—which was sealed in a Lindemann-glass capillary. X-ray diffraction data were collected on a Bruker/AXS three circle diffractometer, equipped with a SMART APEX area-detector, a low temperature device (model LT 2) and a copper-$K_\alpha$ microfocus generator, operated at 45 kV/650 µA and a focusing beam Montel multilayer optic with an image focus spot diameter of ~250 µm (Wiesmann et al., 2007). Data frames were collected using the program package SMART V 5.628 (Bruker AXS, 2001), applying ω-scans with step widths of 0.3° and an exposure time of 5 seconds. Data processing with the program SAINT+Release 6.45 (Bruker AXS, 2003) yielded 23571 reflections ($\vartheta_{min}$=2.80, $\vartheta_{max}$=69.16; −7<h<6, −28<k<26, −34<1<38) of which 4163 reflections were unique ($R_{int}$=0.0242, $R_\sigma$=0.0190). Refinement of the cell parameters was performed using the 99 local cell parameter determinations observed during data integration. An empirical absorption correction has been applied using the program SADABS, a module of SAINT 6.45 (Bruker AXS, 2003). The phase problem was solved with direct methods by the XS module of SHELXTL 6.14 (Bruker AXS, 2000).

The structure was refined by least-squares methods (minimization of $(F_o^2-F_c^2)^2$) using the XL module of SHELXTL 6.14 (Bruker AXS, 2000). The positions of all H atoms were experimentally determined from a difference Fourier synthesis map, $S_{goodness\ of\ fit}$=1.039, $R_{all\ data}$=0.0490 ($R_{obs.\ data}$=0.0379 for 3283 reflections with $|F_{obs}|$>4σ, $wR2_{all\ data}$=0.1041, $wR2_{obs.\ data}$=0.0971). The largest unassigned peaks in the difference map correspond to −0.179 versus +0.185 electrons per Å³. The average estimated standard deviation (e.s.d.) of a C—C bond is 0.002 Å, that of an O—C bond 0.002 Å, that of an N—C bond 0.002 Å and that of a C—H bond 0.02 Å. The average e.s.d. of C—C—C bond angles is 0.2 and that of C—C—C—C torsion angles 0.2°.

The crystal structure of Crystalline Form 2 of Compound I was determined at 293 K and a summary of the structural data can be found in Table 3 and Table 4.

TABLE 3

Crystal Data of Compound I (Form 2) at 293 K

| | |
|---|---|
| Crystal System | orthorhombic |
| Space Group | Pbca; Z = 8 |
| a (Å) | 6.2823(10) |
| b (Å) | 23.285(4) |
| c (Å) | 31.614(6) |
| α (°) | 90.00° |
| β (°) | 90.00° |
| γ (°) | 90.00° |
| V (Å³) | 4624.5(14) |
| Calculated Density (Mg/m³) | 1.280 |
| Unique Reflections | 4163 |
| Model Quality | $R_{obs.\ data}$ = 3.79 % |

TABLE 4

Atomic coordinates and equivalent isotropic displacement parameters [Å] for Compound I (Form 2) at 293 K

| | x | Y | z | U(eq)* |
|---|---|---|---|---|
| O01 | 0.64153(19) | 0.50661(5) | 0.18516(3) | 0.0611(3) |
| O02 | 0.28437(18) | 0.45533(5) | 0.19955(3) | 0.0633(3) |
| O03 | 0.90062(15) | 0.41927(4) | 0.04333(3) | 0.0463(3) |
| O04 | 0.80055(16) | 0.50310(4) | −0.02774(3) | 0.0502(3) |
| O05 | 0.9886(2) | 0.44424(5) | −0.06867(4) | 0.0775(4) |
| N01 | 0.5874(2) | 0.41538(5) | 0.00862(4) | 0.0430(3) |
| C01 | 1.1636(3) | 0.63689(10) | 0.18246(6) | 0.0685(5) |
| C02 | 1.2638(4) | 0.68761(11) | 0.17096(6) | 0.0805(6) |
| C03 | 1.1664(4) | 0.73952(10) | 0.17789(6) | 0.0800(6) |

TABLE 4-continued

Atomic coordinates and equivalent isotropic displacement parameters [Å] for Compound I (Form 2) at 293 K

|   | x | Y | z | U(eq)* |
|---|---|---|---|---|
| C04 | 0.9689(3) | 0.74237(8) | 0.19659(6) | 0.0720(5) |
| C05 | 0.8583(8) | 0.79928(13) | 0.20384(14) | 0.1180(11) |
| C06 | 0.8710(3) | 0.69112(8) | 0.20812(5) | 0.0636(5) |
| C07 | 0.9644(3) | 0.63853(7) | 0.20097(5) | 0.0578(4) |
| C08 | 0.8452(4) | 0.58411(10) | 0.21203(6) | 0.0732(6) |
| C09 | 0.7850(3) | 0.55127(9) | 0.17367(5) | 0.0629(5) |
| C10 | 0.5684(2) | 0.47210(6) | 0.15318(4) | 0.0460(3) |
| C11 | 0.3731(2) | 0.44413(6) | 0.16110(4) | 0.0472(4) |
| C12 | 0.1001(3) | 0.42334(10) | 0.21130(7) | 0.0692(5) |
| C13 | 0.2878(3) | 0.40883(7) | 0.13037(5) | 0.0517(4) |
| C14 | 0.3910(2) | 0.40118(7) | 0.09210(5) | 0.0493(4) |
| C15 | 0.5845(2) | 0.42789(6) | 0.08447(4) | 0.0416(3) |
| C16 | 0.6729(2) | 0.46302(6) | 0.11559(4) | 0.0444(3) |
| C17 | 0.7039(2) | 0.42086(5) | 0.04418(4) | 0.0404(3) |
| C18 | 0.6857(2) | 0.40508(6) | −0.03269(4) | 0.0422(3) |
| C19 | 0.7875(3) | 0.34474(7) | −0.03372(5) | 0.0502(4) |
| C20 | 0.6175(2) | 0.30717(6) | −0.05197(4) | 0.0481(4) |
| C21 | 0.6098(4) | 0.24762(8) | −0.05344(6) | 0.0662(5) |
| C22 | 0.4395(4) | 0.22158(9) | −0.07369(6) | 0.0783(6) |
| C23 | 0.2804(4) | 0.25389(9) | −0.09190(6) | 0.0736(6) |
| C24 | 0.2872(3) | 0.31333(8) | −0.09077(5) | 0.0579(4) |
| C25 | 0.4573(2) | 0.33957(6) | −0.07050(4) | 0.0459(3) |
| C26 | 0.5073(3) | 0.40272(7) | −0.06663(5) | 0.0471(4) |
| C27 | 0.8436(2) | 0.45215(6) | −0.04449(5) | 0.0479(4) |
| H1 | 0.453(3) | 0.4252(7) | 0.0094(5) | 0.054(5) |
| H4 | 0.906(3) | 0.5274(9) | −0.0346(6) | 0.087(6) |
| H01 | 1.231(3) | 0.5999(10) | 0.1763(6) | 0.084(6) |
| H02 | 1.396(4) | 0.6848(9) | 0.1581(7) | 0.097(7) |
| H03 | 1.243(4) | 0.7768(10) | 0.1684(6) | 0.100(7) |
| H051 | 0.899(7) | 0.8235(19) | 0.1837(13) | 0.20(2) |
| H052 | 0.835(7) | 0.8063(18) | 0.2320(14) | 0.208(19) |
| H053 | 0.704(11) | 0.798(2) | 0.1966(18) | 0.28(3) |
| H06 | 0.731(3) | 0.6930(8) | 0.2207(6) | 0.076(6) |
| H081 | 0.719(4) | 0.5932(11) | 0.2274(8) | 0.121(9) |
| H082 | 0.919(3) | 0.5607(10) | 0.2329(7) | 0.096(7) |
| H091 | 0.733(3) | 0.5726(9) | 0.1502(7) | 0.086(6) |
| H092 | 0.923(4) | 0.5349(9) | 0.1618(7) | 0.103(7) |
| H121 | −0.019(4) | 0.4312(9) | 0.1902(7) | 0.092(7) |
| H122 | 0.063(3) | 0.4362(9) | 0.2379(7) | 0.092(7) |
| H123 | 0.136(3) | 0.3791(10) | 0.2109(6) | 0.090(6) |
| H13 | 0.158(3) | 0.3900(7) | 0.1360(5) | 0.059(5) |
| H14 | 0.332(3) | 0.3756(7) | 0.0716(5) | 0.054(4) |
| H16 | 0.803(2) | 0.4808(6) | 0.1100(4) | 0.046(4) |
| H191 | 0.835(3) | 0.3324(7) | −0.0053(5) | 0.060(5) |
| H192 | 0.912(3) | 0.3445(7) | −0.0524(5) | 0.065(5) |
| H21 | 0.717(3) | 0.2274(8) | −0.0407(6) | 0.072(6) |
| H22 | 0.433(3) | 0.1802(9) | −0.0748(6) | 0.083(6) |
| H23 | 0.157(3) | 0.2352(9) | −0.1048(6) | 0.090(6) |
| H24 | 0.174(3) | 0.3357(8) | −0.1036(6) | 0.070(5) |
| H261 | 0.566(2) | 0.4176(6) | −0.0943(5) | 0.058(4) |
| H262 | 0.385(3) | 0.4262(7) | −0.0586(5) | 0.053(4) |

*U(eq) is defined as one third of the trace of the orthogonalized Uij tensor

The experimentally determined powder diffraction pattern agrees with the one calculated from the crystal structure.

The examples and embodiments described herein are for illustrative purposes only and various modifications or changes suggested to persons skilled in the art are to be included within the spirit and purview of this application and scope of the appended claims.

We claim:

1. A process for the preparation of a Crystalline Form 1 2-(4-methoxy-3-(3-methylphenethoxy)benzamido)-2,3-dihydro-1H-indene-2-carboxylic acid (Compound I):

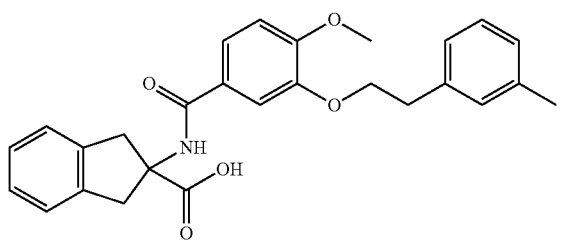

Compound 1 the process comprising the steps of:
(1) adding a mixture comprising a compound of Formula 2:

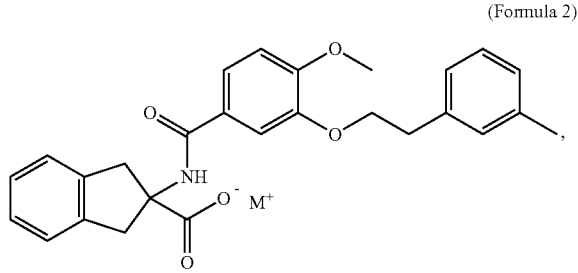

(Formula 2)

wherein M is Na+, K+, or Li+;
in a solvent onto a slurry of citric acid; and
(2) isolating Crystalline Form 1 Compound I by filtration;
wherein Crystalline Form 1 of Compound I is characterized as having: an X-ray powder diffraction (XRPD) pattern with peaks at 5.2±0.2° 2-Theta, 9.0±0.2° 2-Theta, 14.4±0.2° 2-Theta, and 17.7±0.2° 2-Theta, as measured using Cu (Ka) radiation.

2. The process of claim 1, wherein the solvent of step (1) is tetrahydrofuran, methanol, ethanol, ethylene glycol, acetonitrile, water, or a combination thereof; and wherein the mixture comprising the compound of Formula 2 is a solution.

3. The process of claim 1, wherein the slurry of citric acid comprises citric acid in a solvent selected from tetrahydrofuran, methanol, ethanol, ethylene glycol, acetonitrile, water, or a combination thereof; the slurry comprises at least 1.0 equivalent of citric acid relative to the amount of the compound of Formula 2; and wherein the concentration of the citric acid in the slurry is from about 0.5 M to about 1.5 M.

4. The process of claim 1, wherein the slurry of citric acid comprises about 1.32 equivalents of citric acid relative to the amount of the compound of Formula 2 in methanol at a concentration of about 1.0 M; and wherein the slurry of citric acid is heated to a temperature of about 40° C.

5. The process of claim 4, wherein the slurry of citric acid further comprises from 0% to about 5% w/w of seeds of Crystalline Form 1 of Compound I.

6. The process of claim 4, wherein the slurry of citric acid further comprises about 0.5%, about 1.0%, about 1.5%, about 2.0%, about 2.5%, about 3.0%, about 3.5%, about 4.0%, about 4.5%, or about 5% w/w of seeds of Crystalline Form 1 of Compound I.

7. The process of claim 1, wherein the mixture comprising the compound of Formula 2 is added onto the slurry of citric acid over a period of time from about 10 minutes to about 120 minutes; and wherein after addition of the mixture comprising the compound of Formula 2 is added onto the slurry of citric acid, the resulting mixture is maintained at a temperature of about 40° C. for about 3 hours.

8. The process of claim 1, wherein the Crystalline Form 1 of Compound I is isolated after step (2) is further dried under vacuum.

9. The process of claim 1, further comprising a cooling step wherein the mixture obtained after step (1) is cooled prior to the isolation of Crystalline Form 1 of Compound I in step (2).

10. The process of claim 9, wherein the mixture obtained after step (1) is cooled to about 10° C. over a period of time of about 3 hours.

11. The process of claim 1, wherein the mixture comprising a compound of Formula 2 is obtained by saponification of the ester moiety of the compound of Formula 1:

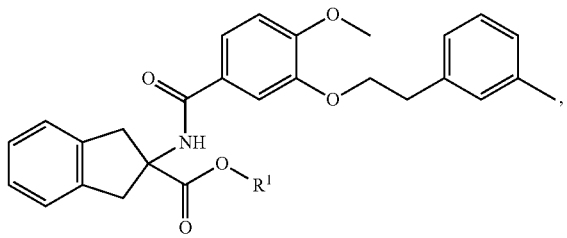

(Formula 1)

wherein $R^1$ is methyl or ethyl in a solvent.

12. The process of claim 11, wherein the solvents for the saponification comprises tetrahydrofuran, methanol, ethanol, ethylene glycol, acetonitrile, water, or a combination thereof; and wherein the saponification comprises a metal hydroxide base having the formula M—OH, wherein M—OH is NaOH, KOH, or LiOH, and $M^+$ is $Na^+$, $K^+$, or $Li^+$ respectively.

13. The process of claim 12, wherein the saponification comprises from about 1.1 equivalents to about 1.25 equivalents of the metal hydroxide base relative to the amount of the compound of Formula 1; wherein the temperature in the saponification step is about 60° C.; and wherein the saponification step occurs for from about 2 hours to about 4 hours.

14. The process of claim 1, wherein the compound of Formula 2 has the structure of Compound 2a:

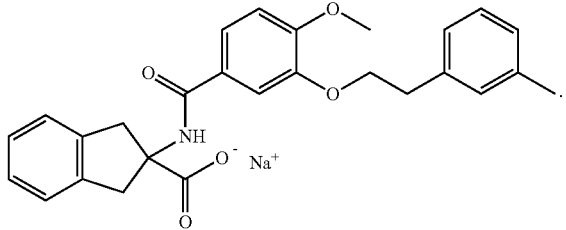

(Compound 2a)

* * * * *